US006991920B2

(12) United States Patent
Ketchum et al.

(10) Patent No.: US 6,991,920 B2
(45) Date of Patent: Jan. 31, 2006

(54) ISOLATED HUMAN TRANSPORTER PROTEINS, NUCLEIC ACID MOLECULES, ENCODING HUMAN TRANSPORTER PROTEINS, AND USES THEREOF

(75) Inventors: Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/298,192

(22) Filed: Nov. 18, 2002

(65) Prior Publication Data

US 2003/0077750 A1    Apr. 24, 2003

Related U.S. Application Data

(63) Continuation of application No. 09/684,390, filed on Oct. 10, 2000, now abandoned.

(60) Provisional application No. 60/230,702, filed on Sep. 7, 2000.

(51) Int. Cl.
*C12N 15/00*   (2006.01)
*C12N 15/85*   (2006.01)
*C12N 1/21*    (2006.01)
*C12N 15/63*   (2006.01)
*C07H 21/04*   (2006.01)

(52) U.S. Cl. .................. 435/69.1; 435/320.1; 435/325; 435/252.3; 435/254.2; 435/254.11; 536/23.5

(58) Field of Classification Search ................ 536/23.5; 435/320.1, 325, 252.3, 254.11, 254.2, 69.1; 530/350
See application file for complete search history.

(56) References Cited

U.S. PATENT DOCUMENTS 5,441,875 A    8/1995    Hediger

OTHER PUBLICATIONS

International Search Report Sep. 16, 2002.
Olives Bernadette et al.; "Molecular characterization of a new urea transporter in the human kidney." FEBS Letters, vol. 386, No. 2-3, 1996, pp. 156-160.
Shayakul Chairat et al. "Molecular cloning and characterization fo the vasopressin-regulated urea transporter of reat kidney collecting ducts." Journal of Clinical Investigation, vol. 98, No. 11, 1996, pp. 2580-2587.
Bagnasco Serena M et al. "Differentaial expression of indidvidual UT-A urea transporter isoforms in rat kidney." Jouranl of the American Society of Nephrollogy, vol. 11, No. 11, Nov. 2000, pp. 1980-1986.
Bagnasco Serena M et al. "Clonin and charaterization of the human urea transporter UT-A1 and mapping of the human S1c14a2 gene." American Journal of Physiology, vol. 281, No. 3 Part 2, Sep. 2001, pp. F400-F406.
Sands Jeff M. "Regulation of renal urea transporters." Journal of the American Society of Nephrology, vol. 10, No. 3, Mar. 1999, pp. 635-646.
Sands J.M.; "Regulation of urea transporter proteins in kidney and liver." The Mount Sinai Journal of Medicine, New York, vol. 67, No. 2, Mar. 2000, pp. 112-11.

*Primary Examiner*—Ruixiang Li
(74) *Attorney, Agent, or Firm*—Celera Genomics; Lin Sun-Hoffman

(57) ABSTRACT

The present invention provides amino acid sequences of peptides that are encoded by genes within the human genome, the transporter peptides of the present invention. The present invention specifically provides isolated peptide and nucleic acid molecules, methods of identifying orthologs and paralogs of the transporter peptides, and methods of identifying modulators of the transporter peptides.

10 Claims, 17 Drawing Sheets

```
   1 ATGTCTGACC CCCACAGCAG TCCTCTCCTG CCAGAGCCAC TTTCCAGCAG
  51 ATACAAACTC TACGAGGCAG AGTTTACCAG CCCGAGCTGG CCCTCGACAT
 101 CCCCGGATAC TCACCCAGCT CTGCCCCTCC TGGAAATGCC TGAAGAAAAG
 151 GATCTCCGGT CTTCCAATGA AGACAGTCAC ATTGTGAAGA TCGAAAAGCT
 201 CAATGAAAGG AGTAAAAGGA AAGACGACGG GGTGGCCCAT CGGGACTCAG
 251 CAGGCCAAAG GTGCATCTGC CTCTCCAAAG CAGTGGGCTA CCTCACGGGC
 301 GACATGAAGG AGTACAGGAT CTGGCTGAAA GACAAGCACC TTGCCCTCCA
 351 GTTCATAGAC TGGGTCCTGA GAGGGACCGC TCAGGTGATG TTCGTCAACA
 401 ATCCTCTCAG CGGCCTCATC ATCTTCATAG GGCTGCTGAT CCAGAATCCC
 451 TGGTGGACAA TCACTGGGGG CCTGGGGACA GTGGTCTCGA CCTTAACAGC
 501 TCTCGCCTTG GGCCAAGACA GGTCTGCCAT TGCCTCAGGA CTCCATGGGT
 551 ACAACGGGAT GCTGGTGGGA CTGCTGATGG CCGTGTTCTC GGAGAAGTTA
 601 GACTACTACT GGTGGCTTCT GTTTCCTGTG ACCTTACAG CCATGTCCTG
 651 CCCAGTTCTT TCTAGTGCCT TGAATTCCAT CTTCAGCAAG TGGGACCTCC
 701 CGGTCTTCAC TCTGCCCTTC AACATTGCAG TCACCTTGTA CCTTGCAGCC
 751 ACAGGCCACT ACAACCTCTT CTTCCCCACA ACACTGGTAG AGCCTGTGTC
 801 TTCAGTGCCC AATATCACCT GGACAGAGAT GGAAATGCCC CTGCTGTTAC
 851 AAGCCATCCC TGTTGGGGTC GGCCAGGTGT ATGGCTGTGA CAATCCCTGG
 901 ACAGGCGGCG TGTTCCTGGT GGCTCTGTTC ATCTCCTCGC CACTCATCTG
 951 CTTGCATGCA GCCATTGGCT CAATCGTGGG GCTGCTAGCA GCCCTGTCAG
1001 TGGCCACACC CTTCGAGACC ATCTACACAG GCCTCTGGAG CTACAACTGC
1051 GTCCTCTCCT GCATCGCCAT CGGAGGCATG TTCTATGCCC TCACCTGGCA
1101 GACTCACCTG CTGGCCCTCA TCTGTGCCCT GTTCTGTGCA TACATGGAAG
1151 CAGCCATCTC CAACATCATG TCAGTGGTGG GCGTGCCACC AGGCACCTGG
1201 GCCTTCTGCC TTGCCACCAT CATCTTCCTG CTCCTGACGA CAAACAACCC
1251 AGCCATCTTC AGACTCCCAC TCAGCAAAGT CACCTACCCC GAGGCCAACC
1301 GCATCTACTA CCTGACAGTG AAAAGCGGTG AAGAAGAGAA GGCCCCCAGC
1351 GGTGAATAG
```

FEATURES:
Start: 1
Stop: 1357

FIGURE 1A

HOMOLOGOUS PROTEINS:
Top BLAST Hits:

```
                                                                    Score      E
gi|4565898|gb|AAD23098.1|AF041788_1 (AF041788) urea transporter...   786    0.0
gi|4104093|gb|AAD01938.1| (AF031642) urea transporter UT4 [Ratt...   784    0.0
gi|1905970|gb|AAB50197.1| (U77971) urea transporter [Rattus nor...   783    0.0
gi|4565900|gb|AAD23099.1|AF042167_1 (AF042167) urea transporter...   724    0.0
gi|2499094|sp|Q28614|UT2_RABIT UREA TRANSPORTER, KIDNEY (VASOPR...   582    e-165
gi|6005876|ref|NP_009094.1| solute carrier family 14 (urea tran...   568    e-161
gi|2499095|sp|Q62668|UT2_RAT UREA TRANSPORTER, KIDNEY >gi|68188...   560    e-158
gi|7650504|gb|AAF66072.1|AF257331_1 (AF257331) urea transporter...   538    e-152
gi|2765238|emb|CAA73322.1| (Y12784) ADH-regulated urea transpor...   533    e-150
gi|1654084|emb|CAA67049.1| (X98399) urea transporter [Rattus no...   519    e-146
gi|1766024|gb|AAB39937.1| (U81518) urea transporter [Rattus nor...   517    e-145
```

EST:

```
                                                                    Score      E
gi|5819458|gb|AI987664.1|AI987664 um05b09.x1 Sugano mouse kidne...   410    e-112
gi|7316545|gb|AW611359.1|AW611359 un63f10.x1 Sugano mouse kidne...   238    4e-60
gi|7045376|gb|AW475270.1|AW475270 un63f10.y1 Sugano mouse kidne...   145    4e-32
```

EXPRESSION INFORMATION FOR MODULATORY USE:
library source:
Expression information from BLAST EST hits:
gi|5819458|gb|AI987664.1|AI987664 um05b09.x1 Sugano mouse kidney
gi|7316545|gb|AW611359.1|AW611359 un63f10.x1 Sugano mouse kidney
gi|7045376|gb|AW475270.1|AW475270 un63f10.y1 Sugano mouse kidney Expression information from cDNA library screening:
Human Thyroid
Human Testis
Human Placenta
Human Kidney
Human Small Intestine
Human Pancreas
Human Fetal brain
Human Heart

FIGURE 1B

```
  1  MSDPHSSPLL  PEPLSSRYKL  YEAEFTSPSW  PSTSPDTHPA  LPLLEMPEEK
 51  DLRSSNEDSH  IVKIEKLNER  SKRKDDGVAH  RDSAGQRCIC  LSKAVGYLTG
101  DMKEYRIWLK  DKHLALQFID  WVLRGTAQVM  FVNNPLSGLI  IFIGLLIQNP
151  WWTITGGLGT  VVSTLTALAL  GQDRSAIASG  LHGYNGMLVG  LLMAVFSEKL
201  DYYWWLLFPV  TFTAMSCPVL  SSALNSIFSK  WDLPVFTLPF  NIAVTLYLAA
251  TGHYNLFFPT  TLVEPVSSVP  NITWTEMEMP  LLLQAIPVGV  GQVYGCDNPW
301  TGGVFLVALF  ISSPLICLHA  AIGSIVGLLA  ALSVATPFET  IYTGLWSYNC
351  VLSCIAIGGM  FYALTWQTHL  LALICALFCA  YMEAAISNIM  SVVGVPPGTW
401  AFCLATIIFL  LLTTNNPAIF  RLPLSKVTYP  EANRIYYLTV  KSGEEEKAPS
451  GE
```

FEATURES:
Functional domains and key regions:

| InterPro | Results of FPrintScan against PRINTS | Results of HMMPfam against PFAM-A | Results of PPsearch against PROSITE | Results of ProfileScan against PROSITE profiles |
|---|---|---|---|---|
| IPR001117 Multicopper oxidase type 1 | | | PS00079 [344-364] | |

| IPR001117 | PS00079 | | MULTICOPPER_OXIDASE1 | Multicopper oxidase type 1 |
|---|---|---|---|---|

Membrane spanning structure and domains:
```
Helix  Begin  End   Score  Certainty
    1    127  147   1.347  Certain
    2    151  171   1.732  Certain
    3    177  197   1.280  Certain
    4    202  222   1.901  Certain
    5    233  253   1.475  Certain
    6    276  296   0.797  Putative
    7    300  320   2.046  Certain
    8    323  343   1.331  Certain
    9    348  368   1.718  Certain
   10    371  391   1.214  Certain
   11    395  415   2.115  Certain
```

FIGURE 2A

BLAST Alignment to Top Hit:
>gi|4565898|gb|AAD23098.1|AF041788_1 (AF041788) urea transporter
          UT-A3 [Rattus norvegicus]
          Length = 460

Score =  786 bits (2007), Expect = 0.0
 Identities = 372/452 (82%), Positives = 412/452 (90%)

```
Query: 1    MSDPHSSPLLPEPLSSRYKLYEAEFTSPSWPSTSPDTHPALPLLEMPEEKDLRSSNEDSH 60
            MSD + SPLLPEPLSSRYKLYE+ +SP+WPS+S DTHPALPLLEMPEEKDLRSS+EDSH
Sbjct: 9    MSDNNRSPLLPEPLSSRYKLYESELSSPTWPSSSQDTHPALPLLEMPEEKDLRSSDEDSH 68

Query: 61   IVKIEKLNERSKRKDDGVAHRDSAGQRCICLSKAVGYLTGDMKEYRIWLKDKHLALQFID 120
            IVKIEK NERSKR++   + R SAG+     L +AV YLTGDMKE + WLKDK L LQF+D
Sbjct: 69   IVKIEKPNERSKRRESELPRRASAGRGGFSLFQAVSYLTGDMKECKNWLKDKPLVLQFLD 128

Query: 121  WVLRGTAQVMFVNNPLSGLIIFIGLLIQNPWWTITGGLGTVVSTLTALALGQDRSAIASG 180
            WVLRG AQVMFVNNPLSGLIIFIGLLIQNPWWTI G LGTVVSTL ALAL QDRSAIASG
Sbjct: 129  WVLRGAAQVMFVNNPLSGLIIFIGLLIQNPWWTIAGALGTVVSTLAALALSQDRSAIASG 188

Query: 181  LHGYNGMLVGLLMAVFSEKLDYYWWLLFPVTFTAMSCPVLSSALNSIFSKWDLPVFTLPF 240
            LHGYNGMLVGLL+AVFSEKLDYYWWLLFPVTF +M+CPV+SSAL+++F+KWDLPVFTLPF
Sbjct: 189  LHGYNGMLVGLLVAVFSEKLDYYWWLLFPVTFASMACPVISSALSTVFAKWDLPVFTLPF 248

Query: 241  NIAVTLYLAATGHYNLFFPTTLVEPVSSVPNITWTEMEMPLLLQAIPVGVGQVYGCDNPW 300
            NIA+TLYLAATGHYNLFFPTTLV+P SS PNITW+E+EMPLLLQ IPVGVGQVYGCDNPW
Sbjct: 249  NIALTLYLAATGHYNLFFPTTLVKPASSAPNITWSEIEMPLLLQTIPVGVGQVYGCDNPW 308

Query: 301  TGGVFLVALFISSPLICLHAAIGSIVGLLAALSVATPFETIYTGLWSYNCVLSCIAIGGM 360
            TGGV LVALFISSPLICLHAAIGSIVGLLAAL+VATPFETIYTGLWSYNCVLSC+AIGGM
Sbjct: 309  TGGVILVALFISSPLICLHAAIGSIVGLLAALTVATPFETIYTGLWSYNCVLSCVAIGGM 368

Query: 361  FYALTWQTHLLALICALFCAYMEAAISNIMSVVGVPPGTWAFCLATIIFLLLTTNNPAIF 420
            FY LTWQTHLLAL+CALFCAY  AA+SN+M+VVGVPPGTWAFCL+T+ FLLLT+NNP I
Sbjct: 369  FYVLTWQTHLLALVCALFCAYTGAALSNMMAVVGVPPGTWAFCLSTLTFLLLTSNNPGIH 428

Query: 421  RLPLSKVTYPEANRIYYLTVKSGEEEKAPSGE 452
            +LPLSKVTYPEANRIY+LT K  +E+K P+G+
Sbjct: 429  KLPLSKVTYPEANRIYFLTAKRSDEQKPPNGD 460
```

Hmmer search results (Pfam):

| Model | Description | Score | E-value | N |
|---|---|---|---|---|
| CE00313 | E00313 urea_transporter | 971.7 | 1.8e-288 | 1 |

Parsed for domains:

| Model | Domain | seq-f | seq-t | hmm-f | hmm-t | score | E-value |
|---|---|---|---|---|---|---|---|
| CE00313 | 1/1 | 56 | 443 .. | 1 | 388 [] | 971.7 | 1.8e-288 |

FIGURE 2B

```
   1 GAGGAAAACT GAATAGGTTT GAAGCTTAGC AGAATGGATT TAATCCAAGC
  51 CCTGTAATCC TTAAGCTATG TACCTGGACA AGTCCCTAAC CTAAACAAAG
 101 TCCACCAAAT TTCCTTGGGT GAAAATGGGG CAAATAGTAG GCCCCTTTTG
 151 CAGCTGTTGT GAAGGTTACA TGAGAAAAGC ACATGAAAAG GTTTGGCATA
 201 CAGTACGCGC AAGAGAAGCT AATCCCCCCT CCTCCAACGT GATCCTTATT
 251 TATTGTAATA ATGGCCCCTA ATCTTTAGCT ACACCTATAT TGATCCCTTA
 301 TCTATATAAT CTAACGCACA TGTGTATTAT TATATTGTAT GTGTGTGCAC
 351 ATGTGATACA TGAGATACAC TCACAACCGC ATAGGTAATC ATACTCCAAA
 401 GAACACACAC GTATGCCACC CCAGGTGTAC CCTTCAATGT AGGGTCAAAC
 451 TTAAAGACGT ATAAAACACC CACATACACT CACTTTAGTC CGTTGGTACT
 501 GTATTAGGAC CTGGCCTATA CAGAATTGTG AAAACTGATC CGATCCCTCT
 551 GTTGTGCCAT GGTTAACAGT ACCCACGTAT GCCATAGATG TGTCCTGGCG
 601 CCATCTAGTG GGGGATCCAA CTTTCTGCTC CATAGTGCCT CCTTAGGCTG
 651 GCTCCAGCCA TTGCTCCAAC TCACCATTTT GTAAGCTGCC TCCATCATCC
 701 TAAAAAACGA CCATGCTGAA AGAGCTCCTC TGTATTTCTT GGCAGACCCT
 751 TTCCAGTTTT CATCCTGGGT GTTTCTGAAC AGGAACATAT CTCATTGAAG
 801 TATTTGCACC TCTACCTACA GACAAGGAAA AGGCTTGGAG CACCTCCATT
 851 CATTGTGCCA ACAGGACCTG AATGACCGTG AGTTGCCCTG CATCATTTAT
 901 AAGTCCATGT CTTCAGGATC TAGAAGGAAA ACTCTGTATG CTGTAATTAT
 951 ATGGCTTTCT GAATTCACTA AATTTAGGAA TATTTTATAT ATTTTTTTCA
1001 GGAGAAAATA TATTCTTTCT TTCAATGAGA ATATTGACCC ACAAAAAGAC
1051 ACCACCAGTC AATTGTTTCA AAGAGATGAG ATGGTACTGG TCATCCTTTA
1101 GCTATGAAGG AAGCCAAGCT GGTTATAGGG AATTGTTACT ACTATACCTA
1151 GATTAACCCA TGGGATTCAA TTTTCATTTT TTTAACTAGG TAGATTTTTA
1201 TATTCCCAAA GCCTTAATAA TAGTGGAGAA AATGGCAGGG CCCTTATGGG
1251 CTCTGGCCTA TATAGCTAAT TAGTTTTGGA AGGTCTTATT CCATTCAAAC
1301 GTTAAGGGGA CTGAGTACCT GGAAAAGGTG AGGGGGGGGG AAAAGGCCGG
1351 GTTAAACTTA TTGGTGGGTA ATAGCCCCAN NNNNNNNNNN NNNNNNNNNN
1401 NNNNNNNNNN NNNNNNNNNN NNNNNNNNNC TGTGTTATTC AATTGGTTGG
1451 ATGTAAGTCA GAGTTCAGCC CACACTCAAA TGGAGTGATC ACACAGTTAT
1501 ACAATGGTGA GAACACAAGG GGGTGGGGAT CAAAGGGAAT CATCTTAGAA
1551 TGTGTCCACC ACAGAGTTGA AGTTTATTTA CTGGCAAAGG ATATTCATTA
1601 ATATCTTATT CAATGAAAGA AAAGGTCACA AAACAGCAAG GACAATAGGA
1651 TCCCTGTTTT GTAAACTAAG ACCGATAGAA AATATATTTG CATGTATACA
1701 TAAATATTCA TGAAACACTC TTTAAGTGTT CCTGGGTTAA CAGTAGTTGT
1751 ATCTAGATGG TGGAATAACA GATGAGTTTT ATGTCCTGTT TCCTTATTTT
1801 TTTCTTTTTT TTCTGTAAAA GGAACATGTA TTGTTTATAA TTTTTAAAAG
1851 AGTAAATATT ATTACCTTTT CAAGAAGCGA TTTAAACCCT CAAGGCTTCT
1901 TTATTCTGAC CTCCATTCTC TTTACAGGAT TGTTTCTTGC TTACTACTTG
1951 TGGTCAACTA AGTAGAGATT CATAAGACCT TTATAGAACC ACTGACAACA
2001 CTGTGACCAA GGAAACTGTG AGTATGTTCT AGAACTTGCT TCTGTGTTTG
2051 TGTCTTCAAA ACAGCTGCTA TCACCAATAA TTAAACCATA AAAAACCGAA
2101 ATTATTTTTC CCTCTGGGGT GATTACAACC ACACGGGAGC TGTGATGAGA
2151 GGTGAGTCCT GTGAAGATCT CCTCCTTGAG TCTTCCCCAC TCCATTCTGG
2201 TTGCTTCCAG ACAAGTGGTA ACAATAATCA CATGCTCATC TCCTCTGAAA
2251 AATTTAAAAG GGATAGGTTC TATTTATATG TCAAAAATAG ATGAACAGAT
2301 CTGACACTGC TGAACATAAT TGCAAATTTG AAAAAAGGAG AGGGAATGGG
2351 TGAGAGAAAA GATAAAGCCA TTAATAGCCT CCATACTTCA TTAGTTTTCC
2401 TTCCTCATGC CACCAGGGGA GGCCCTGAGT TGGGGGTGCC ACTGATTTGG
2451 GGTTGGAATG ATTTCCTAGC AATATAAAAG TTTATTCTTT AAGGTCACTT
2501 GCTGATAAAA ACTACTGGTT TTTGCCAGGC CATCGATTTA TTGGGTTGTT
2551 TGACAAGGCC AGACCAGCTG TTCTATACTT ATATTAAGCC CAAAGAAAGC
2601 TGCTCAAGAT GGATGCCCTG GCATCAGTGN NNNNNNNNNN NNNNNNNNNN
2651 NNNNNNNNNN NNNNNNNNNN NNNNNNNNNC GCCTGAGTCT GTGGGAGCCC
2701 CCCTTCTTGC ATCAGGCATG ACCTGGAATA TGAGACCATG GAGTCAAAGG
2751 GAGAATTATT TTTGAGATTT AAGATTTAAT GCCTGCCCCC ACTGGATTTT
2801 GGACTTGCGT GGGGCCTGTA GCCCTTTGTT TTGGCAATT TCTCCCATTT
2851 GAAATGGGAG CATTTATCCA ATGCCTCCTG CACCCCACT GTATCTTGGA
2901 AGTAACTAAC TTGCTTTTTT TTTTTTTTT TTTTTGAGA CACAGTTTGC
2951 TCTGTCACCC AGGCTGGAGT ACATTGGCAC TATCTTGGCT CACTGCAACC
```

FIGURE 3A

```
3001  TCCACCTCCC AGGTTCAAGA GATTCTTCTG TCTCAGCCTC CCAGTAGCTA
3051  GGACTACAAG TGTGTGCCAC CACACCCTGC TAATTTTTGT ATTTTTAGTA
3101  GAGACAGGGT TTCACCACAT TGGCCAGGCT GGTCTCGAAC TTCTGACGTC
3151  AAGTGATCCA CCCGACTCGG CCTCTCAAAG TGCTGGGATT ACAGGCGTGG
3201  GCCGCCGCAC CCGGCCATTT GCTTTTGATT TTACTGGCTC ATAGGTGGAA
3251  GGGACTTGCC TTGCCTCAGA TGAAACTTTG GACTTTGACT TTCAAGTTAA
3301  TACTGGAATA AGTTAAGACT TTGGGGGACT GTTGCTAAGG CACAATTTTG
3351  TTTTGAAATG TATAAAGAAC ATAATATCTG GGAGGGGCCA GGGGCAGAAT
3401  GATATGGTTT GGCTCTGTGT CCACACCTGA ATATCATCTC AAATTGTAAT
3451  CCCAGTAATC CCCATATGTT GAGGGCAGGA CCCAGGGCAA GGTGACTGGA
3501  TCATGGGAGC GGTTTCCCCC ATGCTGTTCT CGTGATAGTG AGTGAATTCT
3551  CACAAGATCT GATGGTTTTA TAAGTGTTTG GCAAGTTCCT GCTCCACACC
3601  ATCTCTCTCT TCTGCCGCCA TTTGAGAAGG TCCAAGTTTG CTTCCCCTTC
3651  GCCTTCCACC ATGACTGTAA GTTTCCTGAG GCCTCCCCAG CAATGTGGAA
3701  GTGTGAGTCA ATTAAATTTC TTTTTTTTTT TTTTCTAATA AATCACCCAC
3751  TCTCAGGTAG TTCTTTATAG CAGTATGAGA ATGGACTATT GCAGTGGGGG
3801  AGCCAGGATT TGAATCCAGG TATTCTGTCT CCACTGTGCC ACCACTGTCT
3851  AATAACACTA AAATTAACTA CCTAGAGCCA CCTCGGGGCA GCTTGTGTAT
3901  ATAAGTATGT GTGCATGTGT GTATGTGTAG GGTGTATGT GTGTGTGTGT
3951  GTGTGTGTGA GAGAGAGAGA GAGAGAGAGG GAGAGAGAGA GACTACTACA
4001  TTGTGAAATA GTCCACCACA CAAGCCAGAG CAGAGGTCAC CATGCTCCTA
4051  AGAGGCCAGG AAGGCACCAT GGCCATGTTA GGGGTGGGTG TGTGAGCAGG
4101  ATGTGTGTGA GTAAAGGAGA TCAATATTCG TGCATGTGGG AACTGAATTG
4151  GAGGTAGCTG TGGGACCTCA GGAGGCCACC TGCCCAGAAC AGTGGCACAC
4201  ACTGCAGAGA AGCTGAAAAT TGTCTTGGGC ACAAGTGGAG CACCCCTGGG
4251  TAGAACCGAG GGAGATTGAG AACAGTTGCT ATCTTCAGAG CTTTTTAACT
4301  TCTCCCCCTA AGTAGCCTCA ACTGATGGGA GAATTGACAC ATTACCCCTA
4351  CGTAATAGGT GGGCACAGCC TGAAGCAGCC ACCTGCAGAC TCTACATTTC
4401  TTCCCTTTAT ATTTTATTTT AATAATATAA AGAGTTGCAT TTGACTATTT
4451  TATAAACCAT GTTTGCTTAA ATATACAACT ATTATTCTAT ATTAGTTCAT
4501  ATCAAGCTCA ATCAGCATTC CAGAAAACTG TGCTTCTCAG TGCCCTGGGC
4551  ATTGACTACT CTGGCTCAGA GTTTCATGCC CAGTTTCAGG AGCGAAGCAC
4601  TCAGACATGG AGCACCTCAG AAGGTTTTTG AGCAGTGGCA CGACCAAGTC
4651  ATGTTTTAAG ATAATTTACC CATCACCAGT GGCAAGGTGG AGAAAAACTG
4701  GGAGACTGA AGTGAGGGAA ATCAGCTAGA AGGTGACCTG CGTTGGGGAG
4751  GGCCTGGCTT AAAGGGAGAT AATGGGCTGA TCCAGACTGA GGGCTCTGAA
4801  GGAGAACTCG ATGGCTGAAT AATTGCAACT GATGGAATGC AAGAGGCAAT
4851  AAATAAATTG CCATTTATTC ATGGGATGAG AGGGCTCAAT ATGTGGAACA
4901  TTGAAGGGTC ACCCCACTTT AGAAGTGTCA CATAAGGACC GGGTGCAGTG
4951  GCTCACACCT GTAATCCTAG CACTTTGAAA GACCAAGGTG GCGGATTGC
5001  CTGAGCTCAG GAGTCTGAGA CCAGTCTGGG CAACATGATG AAACCCCGTC
5051  TCTACTAAAA TACAAAAAAT TGGCTGGGCA TGGTGGTGTG CGCCGGTAGT
5101  CCCAGCTACT AAGGAGGCTG AGGCAGGAGA ATTGCTTGAA CCCGGGAGGT
5151  GGGAGGTTGC AGGGAGCCGA GATTGCGCCA CTGCACTCTA GCCTGGGCAA
5201  CAGTGGAGAC TCCATCTAAA ACAAAGAAAA AGTGTCACA TAAGAAGGGT
5251  GTGACGATCT CCTATGAGAT TCTTCCAAAC ACAAGCTAAG GAGGAGCATC
5301  AAAAGAGGTC AAGTGGTCTG CTCTCTCCCC CACCTCATCT CACAGCCACT
5351  GCAGGCTCCT CAGAGCTTTT CTGCTGGAGG CCAGAATTCC CCTGCCAGGC
5401  TCTGGTTAGA TTCTCAGCTG CAGAACCCCA GCCCTGGCCC TGCAGCAGAA
5451  ACCAGAAAGA TAAAGCCCCT GGCCCACTGG CCACCAGCCA TCTCTAACCC
5501  CAGCCAGTCC TCAGAGGACC CAGAGGAGGT GGTGCTGCCT CTGACTCCTG
5551  CCCCACCCAG CCTGACCCGC TGGCCCCAGT GAGTCAGTCT CCTCTCAGCC
5601  CAGATCAGAC TTACTAACTT GGAGCTGCCA AGAAAACTCT GAGCCACCCC
5651  TAATAAAAGC CGGCACTCAG CCAGGCTCTT ATACAACCCA GCCCTGAGTA
5701  AGGCACCTCT CAGCCCAGCT ACTGGACTGT TTACCTGCCT TGTCTTCTTA
5751  GTGCCCAGGT GTCTCCTGGA TTCCTCCCCT CCCTGATCTC CCTGATGTGT
5801  GATCCACCAG TCCAGGGGCC TCATCTGTCC CCATTCTGGC AGCCTGACCA
5851  AACATCCACC TAGCCCCACA CACCTGATTT TCACCTTCA GAGTCTACCA
5901  ACTCAGGGAT GAGTGAAGCC AGTGCTCCCA GGGACCCAGC CTGACTCACT
5951  CAGCAAGGTC CTTTCAGAAT GATGCTGTCA CTGAGATCCT GGTGGCAAGA
```

FIGURE 3B

```
6001  TGGCAGAGAG TCTGGGGTTG TGTTTGGTGA GCCAGAGTGA AGGACAATCA
6051  AGCAGACTGC CCTAGAAAAA TGAAGGCTTA GGATCAACCT CTGAAGTGCT
6101  CTTAGGTGGG AAAAGGAGTC CCTGTATCCT GTGCAGGTAT AATGGACAGA
6151  ACTGGAAACA GCAAAGAGAA AAAGTCCCAG GGACTTGATG TCAGCTCCAC
6201  AGATACAAGG GTTTCTAGTA AGCAGGGCTG TTCTCAACAA GACCAACCTG
6251  CCTCATGGGA AAGGGGACCC CCAGCCAGGA GAAGCTAGGT ATCCAGAGGC
6301  GTTAAAGAAT GGATTCCTTC ATCATTTCAG AGAGGGACAT CCCTCTTGGT
6351  TCTAAGGTTG TAGAAATTTA TGGAAACTCT CCCTTGCATC AATTGCAAGG
6401  TCTTAGGCAA AATATATCAA TCCAACTAAT ATTCTGGAGA ACCTGCTAAT
6451  CACTTTTACT TCTCCAGAGC TGCTGTGGTC TCAATAACTG AGTTGGTTAG
6501  AAGATGAAGT AAGGCCAGGC ACAATGGCTC ACGTCTGTAA TCCCAGCACT
6551  TTGGGAGGCC CAGGCCAGTG GATTACCTGA GGTTAGGAGT TCAGGACCAG
6601  CCTGGCCAAC ATGGTGAAAC CCCGTATCTA CAAAAAATAC AAAAATTAGC
6651  CAGGCGTGGT GGCAGGCGCC TGTAATCCCA GCTACTCGGG AGGCTGAGAC
6701  AGGAGAATTG CTTGAACCTG GGAGGAGGAG GTTGTAGTGA GCCGAGATTG
6751  CACCATTGCA CTCCAAGCTG GGTGACAAGA GCGAAACTCT GTCTCAAAAA
6801  AAAAAAAAAA AAAAAAAAAA AAGAAGTAGT AAATGGGGCC ATTTGAGATT
6851  CATCCCCAGA TGACCAGGGG ACTGGTATAC TTAAGCCCAA GAGACTAGGG
6901  ATAGGGAGAG AGCTTTGACT CTGCACTAAT TCACACCAAC AACTCAAGAA
6951  ATCCCTTTGA ACATGGGCCC CTTACATCCC AGGGCAGCAG GAGCATACGA
7001  AATAGGCACA GCCCCTCTTC ACTGGGCATG GGCGTGTTTC TGCAATTCTA
7051  CTGGAGATGG ATGATCTTTA GGAGAAAATA ATCAGGAAAA GAATTTCAAA
7101  ATTAGTACAA TAGAGCAGGA GCCACAGTTT TTCTAACCAT TGGAAGAATT
7151  TGGGTCCAAA CCTAGACACT AAGGACTCCT GACAGTCTGG TTCTCACACC
7201  CTAGTTTTGT CTTTGATTGC CTGCTGACAT CTCTCCCATG CTGTAGCAGA
7251  GTCCATGCTG GGACTTGCTT GCCCAAACCA TGTATTTTCT CAGGCATTTC
7301  TCTGGAGTGT GCTCCTCTTT CTCACCTGCT TAGCCAAGTC CTGACATGGA
7351  AGCTGAGCCC AGTCTCCCCA GGGCTGGGAG GGCAGGGCAG CCGCTCTGTG
7401  CTCTCTGCAC CGCCCTCTTG CCCTCTGCCC TTGTGCCTCC TGCTCAGGAC
7451  ACAGTGCCTG CTCACTGCTT CTCCTGGGCA CTCGAATGTG AGCCCTTTGC
7501  AGGCAAGGAC TGGGCCTTCC AGCAATGATC CCTCCAGGGT AGCCCACAGG
7551  CGAACGGTAG ATATTCAACA AGGAGGGTTC TTACAAAGAG GATGGAGGAG
7601  CTGGTCTGTT TTGGGAGCCC CTTGCCAGAC ATTTGAGGCC TGGTTTTTGG
7651  AGAGACGTGG GACTGATCCA AACAGCCTCT CTGTCCATAT TTCTGAAGGA
7701  GAAGAGGAGG TGTGGGCAGC CAAGGAGAGT CTGAGTGCGC CAAGCAGATC
7751  ATTATGTGTT CTTGAAGCA GGTTTAATGG ACTGGCGCTG AGCTGAGCTG
7801  GGAACGGGCT GAGGCCCTCA GCCCGGACGT GGCTCGGGCA GGGATTTCAC
7851  ATCCAGTTCT AACAAGTGGC GACGCCTTAT GGAAACTTTT GAAAGCTGTT
7901  CCGTTTCACA CCAGCCAGCT TGTACTTCAT CTGGCTGCTC CCACCCTCTC
7951  TCCCTTCAAT TTGGAGCAC GAGAAGAGGG AAAAGTAAGA TCACTAAGCG
8001  CCTACTATGT GCCAGGAACC AAGTCAGCAA TTTCACTGTC CTGAGAAGCC
8051  TACGTTGCCC TTCGGAGACA TGGAGGCCCA CGCGGCCCCG AGTGGCAGAG
8101  CAGGGAGGCA GGAGCAGCCC CACCTCACAG CCTGTGCTCC TTCCGGATGC
8151  GGAGACTTGC TCTCCACAGG GCCATTGGTG CTGCATGTCT CGCCCCCTAC
8201  CCCAAAGCCA AAATTCCCCG CTGTAACAGA GTAAACATTC CCGTGGCAAA
8251  GGAACGCTGT ATTCCCTAGA GGAGGTGCAA GGCCCTGTTC CTGCAGAGGA
8301  TACATAGGCT TGAGAAACAC AACAGCGGGC TGAGGCCCTG ACCCAGGCG
8351  CTCAAGGGCC AGCCACTCGG CTGTGCATGG CCCAGCCAGG CAGTCAGAGT
8401  AATGGAGAGC GCAGTGGGGA ACTGGGTCTA ACCTTGACTC TGCAGCAAAC
8451  TGCTCATTTT CTGGGTCCTG CAAATGTCAC AATGAGGTGA GCTTGCTCTG
8501  GAAAATGCTG AGAGCAACAT ACACATGAGA ACAATTCCT ATTTTGCTTT
8551  TCAAGGACAT GATTTATCTG TAAATGGAAA TATTGTCTGC ATACAGAAGG
8601  GACTCAAAGG TGGAGTACCT TTTTGGAGAG TACCCTAGAA AGAACTTCCC
8651  TTGTGCAATA ATAATAATAA AGGGATTTTT AGGTGTAAGG CTTTCTGTTG
8701  GGTGGTATAA ATGCAGAAAT TAACAAGGTA ATGGCCCCTG TTCTTACAGG
8751  GATTATAAAG TAGACACATT TTTTTTTCAT CAAAAGAAAT ATAAAAATCT
8801  TTAAATTCTT ACGGTTAGGA ATAATTTCT GAGTATACCC ATTCTCAACT
8851  CCTACCTGTA TACTTCAGCC CCACCACTTA AAAGAACACT ATATTCCTT
8901  GATTATATGA TGTATATTAT TTTCATATTT TAACATTTCT AAAATCAGGA
8951  TGCATCTTGA AATTATGAAT GGAAGCATTT CTTCTTTCT TTATGATACA
```

FIGURE 3C

```
9001  TAAAATAGTG ATCAATCTTA CAGCTGATAA CATCTTAGAT TCCATGAAAT
9051  ATGTTTAGGA AAAACCTTTA TCATTACCAC TTTTCAGCTA GACTTTTAAT
9101  AGATTTCATA GCCACTGAAT TTAACACAAG GCCTTTCCGG AACATATCTA
9151  GTTCATCCAG TTGTATAGTG TCATGCAGAT TGTGTGTCTA GATATCTGAT
9201  TGCCCCTGCT TACTTTTCAT ATGGTTGGCT TGGAGGGAAA TTTTTACCAA
9251  GGGCCAGGGA TGCTGTATCA CCTCTTGGCC ACCAGAGGGA GAGAGCGCAT
9301  TGGAGAGGAA CAGGTTCTGG GGCTTGTCGG ATTTCACTGT CTCCTAAACC
9351  TTTCCAGCAT GCCCCCTCTA TGGCAGTGTG CCCACCCCTT ACTGAAACCC
9401  TACCTACAGG GTCAGAATAC AAGGAAAGGC CTCCATTCCG GAGTTATGGC
9451  AGCATCAGGG TTAGTTAGAT CTGAATGACA TTTGCAGACC TACACAAAAA
9501  TTCACAGTGG TCTAATGAGC TCCTCCTGGG AATGAGAACG GTGCTAGACA
9551  TGACAGGGGG TTCTGCCTGC AGAAAATGCA TGGCTGGTGG GTGGCCCCAC
9601  GCTGTTCTGA AACCACTGGA GATCCCTGAG ATCCACAGAG ATTTGTAAAG
9651  TTATGCAGAG AAGTGTTCCC TATCTATCAG TCACCTGTAA CCTTGCTCAC
9701  AGTCGCTTCC TCCCCCCCAC CTCTTCCTTC CATATTTATT TATTGAACCC
9751  TTACTACATG CCACACACTG TGCTAGGAGC TGGGGTCAAA GCAATAGACA
9801  GAACAGAGGA GGCCACCGTC CTCATGAAAC CTAAGTTCTG GTGGGAAGAT
9851  AGAAACCATA CAAATAAATA TACAAATCTG CTATAAGGAA AAATACCTGG
9901  TCCCATGAGA GTATGTGACA GGAGAACATG GTGGGTGGAT CTGCGAGGGT
9951  TTATTTAGCA AGTGATCATT GAGACAAAGC CTGGCAGAAG TGTAGGGGTT
10001 GACCAGGAAG AGTGAGGGAA AGGTCTTCAT GCCAATGAAC CAGCACTTGC
10051 AGAGGCCCTG AGGTGGAAAG TGTTCAACAC CTTACAAGTA CTAAAAGGAG
10101 GCCAGCATGG GGCCTGGAGT CATGGAGCCA GAAAGCAAGG GACTCACTAA
10151 AGCACAGTGG CAGCTCAGAG CCTTGCACAC CCTGTCAAAG AGGTAGTTTT
10201 CCATCTGAAA GCATTGATGG GCTTTAAGCA GGGATCCAAC ATGAGATTAA
10251 TATGGCAACT CTTCCCTGCG GGCATGGCT TTGAGGAGAA ACCTGGGAAA
10301 AAGTAGGGAT ATCCAAATGA AAGTCATTGA AGATGTGGTA AGAGGTGATG
10351 GTGGCTAACT GGTGACCATG AACGTGAAGG CATATTTTTT AGAGACAGAA
10401 TTGTTAAATT TAGAGAGTAA GAAGAAGGGA GCATTAAGTG TGACTCCTGA
10451 GTTTTCTGAA GGAATGGCTT GGAAGGGGAA GATGACTTTT CCTAGGTGGT
10501 CACCTGTGAG GGAGGATAGG ATTTGGGAAG GCAACATGAT GAGTTGTTTT
10551 GGCAAATTAA GGTACTTGGA ACGTCTATAT GTGAGTGTAA AGTAGACAAC
10601 TAAATCTGTT AATCCACTGC TCAAAACTGG GCTGGAAATG TGAGTTTTGA
10651 GGGTCATCGG CAGGGAGATG GAATACGAAG CCATGCTGAG GGCTGACGTC
10701 ACCTGGGTAG GAGCACCAGG GCTGAGAAGA GGGCCCGGAA CAGGGGTCTG
10751 CAAAATGCTC CTGTTACACG AAGAAGGCC GCCAAAAGAC AGTGTGAAGG
10801 AGCAACCAGA GAGGGGAGCA GATATAACGG CCAAAGAGTG TGTCAAAGAG
10851 GGTGATCAAC TCTCAGAACA CCACTGAGCA GCCTGGTGGG ATGGGGACTG
10901 AAAGTGGACT TGCCATGGAG GCCTTAGAGA CCACAGCAAA GGCAGCCATA
10951 GCAGAAAGCA GACTGAGCTG GACTAAAGAG AGAAAAGGGA AGCACCTAGT
11001 GTTCACCTGA GGACAGCAAT CCAACTTACA GTGAAAGCAA TCTACTCGGT
11051 TATTACCCTT GTTCTCTAGC CATGTTCAGT TGTTTGGTGA AAGCATGGAA
11101 AAGTTAGGCA TTTGGGTTTA TCCCGGCTGG AATTTCACCA TACAAGCATG
11151 AGGGAGGGAG ACAGGTGCAA GAGAGTTGGA GGAAGTAACA TAAGGGGCCA
11201 TGAAGTTAAG TTGGTCAAGG AGGGAAGGGA AGACAGGTGG TTGTGGGAGC
11251 TGAAGGGCTG TCAGAGGGGT CACCTGAGCA GGTGAGCCAA ATGTGCAAGA
11301 GGAAGTGGCC AGAGGAGAGA TCTGACTTTT GAGATTTCCA GTGTGTGTGA
11351 TATTAAGCCC ATGCTGGGAC TGTGGAAATC AGTTGCTGAA AAGGGGAGAT
11401 GAAAAGGTTC ACTGGAGATG AGAAGGACAA GGATCTGAGA AGCCAGAGAA
11451 CAGGATGATG AGTTATCTGC CTGGACATCG AAGCTGCTTA AAGTTACTGG
11501 AGGGGGATGA AGATGATTAG TAGGAGCACT TCAAGTCTTC TCTGAATGAC
11551 AGAGTGACCA GAGAGTCAGT AACGCAGCAG TGGGCAGTTG GAGAGGATGG
11601 TATGGCCATT TGAGATAAGC CTCAAAGAAG AAGGGTTTCT GCCCAAGCAA
11651 GGTGAGTGGT GCTCAGAAGA AATTGTGGAG AGTAAGAATT CCTCTCATTA
11701 GGAGGAGGAG AGGTAATAGC CTAGCGAAAT GGAACTAATG CAAAATTAGA
11751 TAGGGGACTT TATCCCCTTT TGAAGGGAAT CCTGCAATCC TTGAGCGGTG
11801 TCTGGAATGA TGAGTATACG GAATGGTAGT ACCCATGTTA GGGATCTGTG
11851 ATCCCTGTCC TAAGAGAGAC GGTCCTACAC TGAAGGGATG CAGCATGGAG
11901 CACGGAGCAA TGGGGAAAGC TCTAGGTCAT ACTGAGAGGA GACCGCATGC
11951 AGGTCCAAAA CCACCTCTCA AATAAATAAA TAAAAGATA TAACTGAGCT
```

FIGURE 3D

```
12001  GGAGGAGGCT AGAGAAGAAA TGCACAAATG GCTGTATGGG AAGGAGAGAG
12051  TACAGCACTA CCAAGGGGAA GCCAGACAAA ACCAGGAAAC TGAGGACCTC
12101  AGGCAAAGGA TGTTCCAAAA GCAAGTCATG GCATAAGCCC TGACCCTGGT
12151  GGTACGGGGA CAGGAGCCCC ATGTGGAAGG GAAGCTCCTT CAGCTGGGAT
12201  GCACACAGCT CATGGAAGAA TAGACCAGTG CTTCCTACTG TTCCTAGGGA
12251  AGGGAAAGAG GGAAGGAGCT GGAAATGGTA GAGGGAAGAG AAGGAAGACT
12301  GGAGATCAGT TGTAAGCAAT GTAGCCTCCA TAGAAATTCA GGAAGAGTTT
12351  CTCTTAGACA CCCCCCACCT CCAATCAGTA CTGGATCTGT GTGTACGTAT
12401  CAAGGGGAAC ATACGTGTAC CACTAACTAC CACAATAGGA CGGCACAGCA
12451  GGCAATATGA AAGGCAGAGA AAAAACACTC AGTGATCAAG AGAAAAAGAG
12501  AGACTTCCAT TCTGACTCAG TGGTCAGGGA TATCTTCATC GGCCAAATGG
12551  ACATTCTTCT GGACGCGGAA GAATGGGAGG ATTTTGAAAG GTAATGAGGT
12601  AGAGAAATGT CCTCAACTCT ACAGCACAAG CTGTAGATCC CACGTGTGTC
12651  ACTGTCCAAC CCCCAGGACA GACCTGAGGT CTGAGTCCAG CCTCAGCCAA
12701  GTCCCTCTGG GCCCGTCCT GACTCACTAG CTCTTTCCCT TTCCTTCCGT
12751  CTAGTCCATC GATAGAAGAG TGGCTGTGAC CCGAAGGAAT GTCTGACCCC
12801  CACAGCAGTC CTCTCCTGCC AGAGCCACTT TCCAGCAGAT ACAAACTCTA
12851  CGAGGCAGAG TTTACCAGCC CGAGCTGGCC CTCGACATCC CCGGATACTC
12901  ACCCAGCTCT GCCCCTCCTG GAAATGCCTG AAGAAAAGGT GAGAAGTGTC
12951  CCTCCTAGGA TGTTTCCTGG GAGGGAGGGG ATGGGAAAAG TGGGGGCAAA
13001  AGATGCCGCT TTCCCACCTT CCCAGTGAAC TTAGCACACT GAGGAAGTGC
13051  CACTGTCAGT ACATGGTGAC ACCCATGGTG GGTCCTACCT GGCCTTAGAT
13101  AATGTGGCTC TTCATGAGAC ATGATTTTAA GGACAAGTAC AGAATACAGA
13151  CACTCACTCA CCAGTCTTTC AATCAGTCTC TAAAATCTTT CCCCTTAAAC
13201  CTGCTCCCTT GAACTACCCT ACTGTCTCCA AGGGAAGGC CTTTGTTGAA
13251  ATGCAGGCCA TTAGCATCCT CGGTGGTAGC ACAGAGGTAG ACTGGCTGGC
13301  CACTGCTGCA GTAGAGAGGG ACTCAAGACT GCTGGGATGG CCTTCCAGAG
13351  CTGTCCTGAC TTGCGATGAG GAGGTCCCAT ATCTTTACTC ATCACTACTT
13401  TGAAATTACA GAAGGTATTG GATCTGCTGT GCATACATGT GTATCTTAAT
13451  TTTTAGTAAG ATTATAACTG CATTTCAGTA TAATTGGCTT GGTTTGCCGT
13501  CCTATTTATC TGATCTTTGC ATTTACAAAC ATTATTCTGA AAAGAAGCTC
13551  ATGGGCTTCA TTAAACTGCC AAAAGAGATC CATGGCACAA AGGTGAAGAA
13601  ATCCTGCTGT GAAGAAGGTG CATGGTCCTG GAAGAACAG GCTTGTACGG
13651  GGCACTCTAT GCAGCCGCAG ACAATGGGCA TGTGTTCCAC CCTTTGTCTC
13701  ATGATCCTTT ATTTTTATCA AAAACCTGC CACCCTCCTC TATCCCCAAA
13751  TGTCCCTGCT CTCAGAAAGC TGTATCATTT GATGTCTGGT TGGTTTCTCC
13801  TAAAAGGATC TCCGGTCTTC CAATGAAGAC AGTCACATTG TGAAGATCGA
13851  AAAGCTCAAT GAAAGGAGTA AAAGGAAAGA CGACGGGGTG GCCCATCGGG
13901  ACTCAGCAGG CCAAAGGTGC ATCTGCCTCT CCAAAGCAGT GGGCTACCTC
13951  ACGGGCGACA TGAAGGAGTA CAGGATCTGG CTGAAAGGTA GGAAAATACC
14001  CTGGGGAGAG GCAGCCAGAC CAGGCCAGGC CAGAGAGACA ACCCTCTCTC
14051  CGGTTTGGTC CAAAGCTTCT CCCTCACTCA TTCACCCTCA CCCTGGGTGG
14101  ATCTGCCCAG GACTGGACCT CACCCAGGGC TGGAGTCCAC AGCTGGGGGA
14151  ACTTCAGCCC TAAGCTGACT CCAAGGGGAT ATGATATACC CTACTGGCCT
14201  GGAATTCTCA TGGTTTCAGA ATTAAATGCA TTGATCTTAG TTCTTTGCAA
14251  ATTGCTCGTT CCTATGTGAA ATAGATATAG GACAACCATA TTAGCAACAT
14301  ATAAGCCATT TCCCAAGCTA GCTGAATGAT CATTCCTTCA CTCGATTCAC
14351  TTGTTGCACA GCCATTTATT ATGTGCCTGC TATGTGCCAA GAAAATATTG
14401  GTATCATCCT TCCCAAAGCT TCAGGATTCT TTCCTTTTAA CTTCTCGAAC
14451  TAAACACTGA AAGGAATGCC ACACCCTTCA CTCCCACTAG CCCCGACACC
14501  TGCACCAGTT GTCATGGAAA CCAAACCAGC AAATGAGGCA GAATGTACGC
14551  CCCTCTCCTA TACCTGGCCT CCTCCAGGCC CTGACTCAGT ACTGATTTTC
14601  ACAGCTGGGC TACAACAATT TCTTCCCTAG TGTCTTTTCT TCAGGCTACT
14651  TTCTTTGCTG CTCAGATACC AGCCCTTAAC TGAGTCATCC AGCACTACAG
14701  AAAAAAGAAT TTCCTGCCCC CACCCCCCCA CCTTCCCCAC CCTTTCTTTT
14751  GGACCAATAA ATTTCCCTTG GAATGCTCCC GGGGCTTCTT TTCCAACCAA
14801  GCCAGTGGCT GGAACAGCGT TAAATTGTTC TCAGCATGGT GCCTCTGTCT
14851  ATATGGCAAA AACTACCACC CACTGCAGAA TGATTGCTGG GCTACTGAGA
14901  GATTTGGGCT GGGCACCAGC CTCCCCTCTA CCCCCACCCC TCCACCCCGA
14951  CCCCTGGCCT GGCTGAATGG GAAGGGTCCT GGCTTGCACA TTCCTGTTTG
```

FIGURE 3E

```
15001  CCTTGGTTGC CATGCCAACC AGCAGTTCAG CAGAGCAGCC CAAGCTGGAC
15051  CTGCTGATGG CTCGCTCTCT GTCTCTTTCA GACAAGCACC TTGCCCTCCA
15101  GTTCATAGAC TGGGTCCTGA GAGGGACCGC TCAGGTGATG TTCGTCAACA
15151  ATCCTCTCAG CGGCCTCATC ATCTTCATAG GGCTGCTGAT CCAGAATCCC
15201  TGGTGGACAA TCACTGGGGG CCTGGGGACA GTGGTCTCGA CCTTAACAGC
15251  TCTCGCCTTG GGCCAAGACA GGTGGGTCCC TCTCTATAGG GATTTTAGCA
15301  AGATGTGTGG AACAGAAAGT AGAGAGGTGT TTACTTGAGT AATCAGTCAA
15351  CCTTACCCTC CCAGCCAGCC AAAGTCTCCT GAGTATCAAC TTTAAGCAGG
15401  TCACTGACAG TCCTTGCAGA ATTACACTGC TCCTGCTCAC AGCATGTGAC
15451  AGTGTCAACA TTCATTTTGA CTGTGGAGAC TTCTGCAAAA CACTGCCTCA
15501  GAGGGAGGTG CAGAGGAACA GCTAAGCTGT TCTTTCCTTC ACAGAGCCTA
15551  CCATTTTAGT TGAAAGGAAA CAAGAATTNN NNNNNNNNNN NNNNNNNNNN
15601  NNNNNNNNNN NNNNNNNNNN NNNNNNNNGT GCTGGAAAGC GTATTCCCTT
15651  CCTGCATCTG CAGGGGAGCC CTAAGCTTCC AGAAGCTTCT GCCATGCAAG
15701  GAACAGCCAA CACATGGTAA GGTTTAGCAC GCCCACATTA TTCATTCAAC
15751  AAATACTAGC TGAGCACCCT CCATGCACAG ATACTCTTGA CATTGCTGGG
15801  TTACTGGGCC ACAGCAACGG ACACACAGAC ACACTTCAGC CCTCATAGAA
15851  CTAAGGCAGG TGCAGAGGGA CTGACCACAA GCACACACAG GTCACTCCTT
15901  GGCAGGGGCC TTGCATCACA AGCTGCCTAT GCCCCTCCCT CACCCACAGC
15951  CTATGCCCCT CACCCGGCAG AGCAATTAGA AAGGTCAAGG ACAGTGTTTA
16001  TTACGATCAG GAGGAGAATT GTAGGTGCAT ACACCAGCTT CTCCTCTGAA
16051  AAAGAAGGAG TGGCTAGACT CATGCTTGGA TACTACCACA CTTCTGGGCT
16101  GCTCCTCACC AAGGGGCACC TGGGAACCCA AAGCTAAACC AGCTTATTCA
16151  CTCTGTTGCA GACATGCAGA GAGAAAGTAC ACAGATTCCA GCTACAGAGA
16201  ATTTTTTGTT TTTGAGACAG GGTCTTGCTT TGTCACCCAG GCTGGACTGG
16251  AGGGCAATGG TGAGATCTTG GCTCACTGCA GCCTCAACTT CCTGGGCTCA
16301  AGTGATCCTC CCACCTTAGC CTTCCAAGTA GCTGGGACTA CAGGCATGCA
16351  CTATCACGCC TGGCTAATTT TTGTATTTTA GCAGAGATGG GGTTTCACCA
16401  TGTTGCCCAG GCTGGTTGAA CTCCTGGGTG CAAGTCATCT TCCCACCTTG
16451  GACTCCCAAA GTGCAGGGAT TACAGGCATG AGCCACTGAG CCTGGCCAAC
16501  TACAGAGAAC TTTACACAAT GTAATCATAA CACTCTTTCT CCTTCCCTCT
16551  CTTCTCTCTC CCTCACTCCC ACACACAACT TCCTTGTGTC ACACCTCAGG
16601  TTTCTATTAT ATTCCCTCTA TATTTAGCAG TCTAAGTCTC CCCTGATAAA
16651  GAAGAGCTTA ACCACAGACA AAGTGCATAA TTTTAATTGT CGATCAGCAA
16701  GACAAGGGTG TGTGTGTGTG TGTTTGTGTG TGTGTGTGTG TGTGTTATCA
16751  GGAAAGGTGC TGGCAGCTAT GTGACTGCCC AATATTCATT GAGCGAACTG
16801  ACTTTTTTCT AAGCATTATT ATTAAAGGAA TCATCTAAAT TAAGCATATC
16851  CTCAGAGCAC CAGGAGGGAG GGGCCCAGTA ACACCACCAA CTTCAAATGC
16901  AAAATCAGTC TGTTTCACCG CCAGGTCTGC CATTGCCTCA GGACTCCATG
16951  GGTACAACGG GATGCTGGTG GGACTGCTGA TGGCCGTGTT CTCGGAGAAG
17001  TTAGACTACT ACTGGTGGCT TCTGTTTCCT GTGACCTTCA CAGCCATGTC
17051  CTGGTGAGGC ACCTCATTTT TTCTGCTCAC AGCTCCATGG GGCCCCCAAG
17101  ACACTTGTGT CTTATACTGG CCAGAGACAG GACATACACA TGTGGACCCC
17151  AGCCCCTTCA TAGCCAAGTT AGCTTGTCTG ACACCATGAA AGCCCATGAG
17201  TTCTCTTGTA ACACAAGGGG GTCATTTGGA GATATGGAAT AAGGAGGATT
17251  CTTTTGTTTT TTGTTTGTGT GACACAGAGT CTTGCTCTGT CGTCCAGGCT
17301  GGAGTGCAGT GGCGCAATCT CGGCTCACTG CAAGCTCCAC CTCCTGGGTT
17351  CACACCATTC TCCTGCCTCA GCCACACAAG TAGCTGGGAC TACAGGCACC
17401  CGCCACCACG CCCAGCTAAT TTTTTGTATT TTTAGTAGAG ACAGGGTTTC
17451  ACTGTGTTAG CCAGGATGGT CTCGATCTCC TGACCTCGTG ATCCACCTGC
17501  CTCGGCCTCC CAAAGTGCTG GGATTACAGG CGTGAGCCAC CATGCCCGGC
17551  CAGGAGGATT CTTTAAACCA ACAAAAGACA ACATTTTTTT TATTGCAATG
17601  GTAATCTTCC TGAACGACAT TCTTAGTAAT AAAAGTCAGC ATTTCCTAAG
17651  TTATTCCTAC ATGCTTGACA CAGTGCTAAG CAGGGCTTAT GCAGTGCTAA
17701  GTATGGCTAC ATTTGCCATC AGTTTATGGA AGGGAAGACC AAGGCATGCA
17751  GAGATTAAGT CACTTGCCCC AAGTTGTACT TTGTGGTAGT TTTTGATGCT
17801  GGCATTCCAA ATCCAATCTG CACTATTAAA CCCCAGGTTG CATGGGAATT
17851  GTCTATTATG TGACGTAACC AAGACCTAAA AGCTGAAAAC CTGCTTGTGA
17901  TAGAAGCAGA GAGCTTTCTT GGAACAGAAT ATTTATATGT AAAGCATAGA
17951  ACCTTTGAAC TGGAAGTATC GGTTGAGATC TTGCTGGGCA ATCACCCTCA
```

FIGURE 3F

```
18001  TATTCTAGAT GAAATAAGAA GGTCACCATG AAAGGGAGTT AGGAACAAAT
18051  ATTCACCTAG CGAAGGGTGT GCTGGGCCAT TCACACAATG ATTCTTAGTT
18101  CACGTAAATT TACAGCAGGT CTATCAAGCA TCTTGGGGGT CTCTGCAGTG
18151  TGCTCACTGT CATGGGGAAC CTTTGTCCCC CCGAACCCTT GACTTCACAT
18201  GGTGTATACC ACCCCTGTTC TCAACTTTCC TTCAAACAGG GGTGATTTTA
18251  TTCTTATTGT CAGCCAATAA ATCAGACAGG AGGATTTACT TTTTAACTTT
18301  CTAAGAGGTA AAGGTCTTTC CTTGGGTTTC AAAGTCTGGG AGTCCTAAAG
18351  CCAGGCTGTT AAGTTTAGCT TACCTCCTCC TTTATATACT TTATTAGAAG
18401  TGCTTGCCAA AAAANNNNNN NNNNNNNNNN NNNNNNNNNN NNNNNNNNNN
18451  NNNNNNNNNN NNNNAAAGAC CAAGAAATTG GGTTTGGCCA AAAAGCCCCA
18501  AGTAAAAGAA AGGAAGGAGT GGCCCAGGAA GGGGAAGGGG CCAGGGTACC
18551  TCGGAATGAA GAGGTCCAGG ACCCAGGGTA CACCCCTGTA GACCCCCAGG
18601  TAAAGCCTTT TGGAATTTCT AATATCCAGG CTGGTGATAG AAAAGCAGTT
18651  AAGAAGAGTT TTTAGGCCAG AAGAATGTGA TGGGGATATG GTTTAAAATC
18701  TAAACCAAAA TCACTTCTGT TTGCAGGATG GGAGACCGGA TTTTAACTGG
18751  AAGTAAGAGT GGATGCTGGA AGCATCTGCT ACAATAATCC ACAATTGTCT
18801  GCTACAAAAC CCCACAGAGA TGACAGTGTT TAGATTAGAG TGATATCCAT
18851  GAACATGGTA AGAAGTGAGT GGGTCTGGGG TATATTTTAA AGAAGATAGA
18901  GGCAATATAA CTTGTTGGGA GGTTGTGGAA AACCAAGGAG AGGAAAAAAA
18951  AAAAGAAAAT TGAATACACT CCTTTAATTT GCCTAAGTAC CTAGGTTGAT
19001  ACAAAAGACC AAGAGAAGAA CTGGTCGGTG GCAGGAGACA GGATACAAAT
19051  CAAGAATTCT GTTTGGACAC ATTATACTAT AGACTTCCAA GTAGAGATGT
19101  TGTAAAGGCA ATTGGATGTA CAAATCTGAA ACAGTGATAT GATCAAGATT
19151  TGGGAGGTGG AAACACACAG AAGCTTTCAT CTATGGTACT AAAGGCTATC
19201  ACCCAACAGA GAAGATTTTT TAGAAGAGAG AGAAAATATT CAAGACAGAG
19251  TCCCATAGGC TCTTCCAACA TTTAGAAGTC TGGCAAGAGA GGGGAAAAAC
19301  CATCAAAAGA GACTAAGAAG GAACAGGCAA AAAGAAAACT AAGAAAATCC
19351  AGTGTCATGG TAGCCCAGAC AAAGTATTTC AAGATGGTGG GCAGGTCCAA
19401  CTGTCAAAGC AATAGGGAAT GACCATGGAC TTAGCAAGAT AGATGCCATT
19451  GGTGAAATGG ACAAGAGCCA TTTCCATGGT GTAATGAGGG CACACACCTG
19501  ACTGAAGTGG GTTTGGGAAA GACTAGGAAG AGAAAGATTG GGGATAGCAC
19551  AGAAAGCCAA CCATTTCGAG GGCTACTGCC CGAAGGGGAG CAGAGAAACG
19601  GAGCCACAGC TGGAGTGGCC ATCAGGTTAA AGGGGGAAGA TGTTTAAAGG
19651  TAGAAGATAC TAGAGCATGT TATATCCTGA TGAGAATGAT CCAAAGAAAA
19701  AGAAGAGATT GAAGCTGCAG GAGAGAAATG AGAAAATTAC AGGAATGAAG
19751  TCCCTGAGGC AGATTAGATC CAAAGAACAG GGAAAAGAAC TGGCCTGATG
19801  AAGGAGCAGG GATGCTTCCA TTATGTGAAA AAGACAGAGA GGCAGATTTT
19851  GTGGGAAGAA AGCAGACAGG GTGTGGATTT TATGGCTGGG AAAACAAGCC
19901  TTTCTCATCT TGTCACTTCT ATTTTCTTAA TGAAGTAAAG CCAGGTGGTT
19951  GGTGGAGGCT AAAGGGAAGC AGACAGTAAA GATTTGAGAA GAAAGGTGAA
20001  AATGTGAAAT ACTTGTCTCA GCAAGTCGGA GAGTTAACTG GTGAGGGATG
20051  TGTAGGAGGG TTTTCAGGAA GTCTTAAACG CCTTTTTGAA ATTCATGGTC
20101  ATTCATTAAA AGCAGACAAT TTAAACACAT CATGCAACTT CAGGTTTTGC
20151  CCAGCAGGTC ACTGAGTGTG GATGATGTGG GGTATTTGGT GTCTAGGGTG
20201  GCTGGTGCCT TCCAGAGGAA ACTGAAGCTA AGGGAGATTA ATTACCTAAC
20251  ATTGTTCCTT CAGCCTGTAT GCATAGGAGT GAGTCAGGAT TTGCACTAAG
20301  CTTCATCTGT CTCCAACACC CATTCTCCTT CCAAGGAAAA GATGAAGAAG
20351  ACAGAGGGTA CAAACAACTG AAGGTTCTAT TTTCCCCTGG CAGTTTCCAG
20401  AGTAGCTCTA AGTATTTTTG CTGAAACTAG ACCTGCAAAT TACCCATATG
20451  CCATTGCAGC CTCCTCCTAG AAGGTCAGTC TTCTAAAATG TTATCAGAGC
20501  CTTGAACAAT AGTCATTGTA CACCTTGGTG ATTCAAAGGC AATACATTAC
20551  ATTTTGTTTA GTTTCTTGG TTTAAAAAAC AAGGAAATAT TCCACTATT
20601  TTATAAAGTG TTTTACTCAA AATAAGTTAC GATATTTTA AAATTTGTTT
20651  CTCAGAGGTG TAAGCTTATG AAGCAGATGA CAATAAATTG GCAAAAAAAA
20701  AAGAAAAAGG TAAGAGCTGA AATTGAATAC CTATTCTAT TCCCTATCCC
20751  AGATCATTGG AACACTGGAG TCTCAAGGGG GCCAGGAATG CTGTGCCTAG
20801  GAGAGGGGC AGTGGATGAT ACAGTGGCCA GAGCTGCTGA GACAATGTAG
20851  ACCTCAGGAT GTCACAGGGA TTAACCCTCT GTCTCTTGCA TCTTCAGCCC
20901  AGTTCTTTCT AGTGCCTTGA ATTCCATCTT CAGCAAGTGG GACCTCCCGG
20951  TCTTCACTCT GCCCTTCAAC ATTGCAGTCA CCTTGTACCT TGCAGCCACA
```

FIGURE 3G

```
21001  GGCCACTACA ACCTCTTCTT CCCCACAACA CTGGTAGAGC CTGTGTCTTC
21051  AGTGCCCAAT ATCACCTGGA CAGAGATGGA AATGCCCCTG GTAAGTTACC
21101  CAGCGGTGAT GAGTTGAGAC CCCCATATTC CACTGCAGAC CTTCTCGCCA
21151  ACCAATTTGT GGACTATGCC ATGCTCTCAA CTTCTCTAGA AACATCTATA
21201  CCAGATGATG GGCCTCAGCA GGGTATCAGA AAGGGTTGCT GCCACATCCA
21251  TAGATCCTTT CAACAGTACT TATTGAGCAT GTAACATGGC CTGGACACTT
21301  TTTCAGATAC TGATAATACA AGACAATGAC ATCCTGCTCT TAGGAAGCCT
21351  ACATTCTATA CGGGGAAACA GATAACATGC AAGTGAACAG ATAAGCGTTG
21401  ACAGTACAGA ACTGTGGTGG TTGAGTGAAA GATATTAGAT AAAATGTATA
21451  GTCAGATAAA GGGGCAAGAT ACTAAAATAA ACATTTAAAA TTGGGATTTT
21501  AAAGGCATTA GCATAGAAGA CAGAGGGTTA ATTTTTATAT ACTCTCTCTC
21551  TTAGTGGTTC TCAGGCAGGG ATAATTTTGC CCCTTGGAGA CATTAGGCAA
21601  TGTCTGGAGA CATTTTTATT GTCAAGACTA GAGAGGTCCC CAGCACGCTG
21651  CTCCCAGGCC ACTTCCCTCT TTCTCTTTGA ACAACAGAG AAAGGCCTTC
21701  CTTTTCCTTT TTGTTTAATC AGCTTATTGT TGCTATATAA GAATTATGAG
21751  GAGTGTGAAG AAGGCCTGGT GCTTAGTAAA TTTCATGGC ACACCTGACT
21801  GCCCTTCACA CCAGGGTGTC AGCTGCGGCC TGGGAGCAGC GTGCTGGGAG
21851  GGAAGGCCGC CCTGGGGCAC AGCTCACCAG GCTGAAATAT AGATCCCAGC
21901  GGAGGAAGCT TCATTCTAAA CCCAGGCTCC ATTCCAAGGC CACTCATTCC
21951  CTCATTCCTC TCATTCTTGA CCGCTTGGGC TTAAAATCTG CGTTCCCGGA
22001  TGGAAAGGTG GACGTGAACT CCCCTCAGCA TCCGCATTC CTCAGATGTT
22051  GGCAATCATG GGATATTTAT TAAATAGACT TCCAGCCTGT TCCCAACATT
22101  TAAGCTGAGT TCCCTGGTCT GGTACAAAGT GTTTTCTGGG TTTCTATAAA
22151  TAAATATGAT TGAGTACCCC TCCCTTGCCA TTCCTTTCGC AAGATTATAA
22201  ACTCTGGTCC AAACAGCATT TGGTTATTAA AAGACCATTC ATTCAGAGAC
22251  AAGAGTGAGC AAAGTTTAAG AGCCCTCTAG GCTCTTCAAA TACTACTCCC
22301  TGAAGAAATC ATACTTATTC CAGAATTAAA TCAAATTGTC AAAAAGTACA
22351  AAATTTGGTC CAAAGGGAGA AACTAAATTA TTCCCAACAT CTACAGCAAC
22401  GTCTACAGTA GATCATCTAT AACTAATCTC CCATCGCACA CTAGACTCAC
22451  CTGAGGACCT GCCATGCCCC ATATCAATTA AATCAGAATG TCTAGGGAAG
22501  AGCTGGGCAT CAGTATTTGT TTAAAGATTC CAGGGGATT CCACTGTACA
22551  GCAAAGTTTG GAACCACTG ACCTAATCAA TTCCTATTTG TTAAGCACCT
22601  ATGGTGTACC TGGGCATAAA GGGCCCTGTC CTCACAGAGG TCATGTGACC
22651  TGGCAATGGT GAAAAGAACT ACAGAGTCTT AAAGCTGGAA GATCATCTGC
22701  CAAGCCAGCC TCTTGTTACA GACGAGGATG TGACATGCTC ACAGTCACAC
22751  AGTGAACTGT GCAGAGCCCT GATGGAAGCT AGAGCCCTCT ACTCCCAGGC
22801  CAGTGCTCTG CCTGCCCTGC CATTCTCCCT CCTTTCTTTT TCTGCCCTCA
22851  AAGGACTCCA AAAATATCGA CAATTCAGCC TGGCCACAGA AAAGCCATCT
22901  GTCACCACTG CCAAACAAAT TATCCCCAAT TCCAGCACCA AGTTACTCTC
22951  AGGCTCAGGG ATGTCTGGGC TTCAGGCCAT TCTCCAGATG TGCCACATAC
23001  TACCTTTCTA CAATGCTATG CGGTCTTCGA GAGCAGGGGG CATGCCTACT
23051  GCTCCTTTCC AAAGGCTCAC AACCCCCCAG GGTAGCAGTG AATGGGCAGG
23101  GGCCGCCAAA GAGGACGTGT CAGCAGTGGC TTGACAAAGA GACAGCAAGG
23151  GTGACAAAGA CCTCAGACCT GAGCTAGGGG TCAAGCTCAG AGCCTCTAGC
23201  CTGCACTTGA CCAACAACAG GCTGGGTGAC TTTTAGTCAA ATCATACATC
23251  AAAATGCCT ACTGTATTTT CAATATTCCT AGAATATTTG TATGGATTTC
23301  AGAAGGTCTA GAGGAAATCC CCGAGAGCCC TGAAACTCCC AGCGGCATTC
23351  TAGGGAGGAG GTGCATTCTG GTCCCCTCAA AGCAGAAGCC GTATGTTCCT
23401  CAGAAGCATC CATGCCCAGC CCATGTTGGG GGCCCTGGCT TTGCATGAGG
23451  GATGCTCACA TGCCTGCTGG GTGGTAGAGT GAGGAGCTGT TTGTTCCAGC
23501  TCATGCCTCC CATGTTCTCT CACATGCTGG AGGGTACAGT CATCCTCCCG
23551  TTCCACTCCA TTACTCCCCC GAGGAATGGC TCAAATCTGG CCCTGAGTCT
23601  GGTTTTTGCA TTATTGTCCA TGCTCCAGTG ACCTGTATTC TGTTAACTTT
23651  GCAGCTGTTA CAAGCCATCC CTGTTGGGGT CGGCCAGGTG TATGGCTGTG
23701  ACAATCCCTG GACAGGCGGC GTGTTCCTGG TGGCTCTGTT CATCTCCTCG
23751  CCACTCATCT GCTTGCATGC AGCCATTGGC TCAATCGTGG GGCTGCTAGC
23801  AGGTAGGACA GAGCTCCCTC TCTTCAGGTC CTCAGGATAA TTCACTCAAG
23851  GTCACTTTTC CCCTACATAC AGCAAATCTT CCAGACATTC TCTTCCCTGC
23901  AGTTTTAAAT ACTTTCAGGG AGACAGGCAC GGTGACTTAT GCCTGTAATC
23951  CCAGCACTTT GGGAGGCCGA GGCACATAGA TGACCTGAAC TCAGGGTGAA
```

FIGURE 3H

```
24001  AACCCATCTC TACTAAAGAA AAAAAAGTAC AAAAATTAGC TGGGTGTGGT
24051  GGTGGGCACC CATAATCCCA GCTACTTGGG GAGCTGAGGC AGGAGAATCG
24101  CTTGAACCCA GGAGGTGGAG GTTGCAATGA GCCAAGATCG TACCACCTCA
24151  CTCCAGCCTG GGAAATAGAG TGAGACTCCG TCTTAAAAAA AAAAAAAATA
24201  CATGTGGAGA GATGCAAGGG GGTAAGAACC AAGTTGGCCT GCAAACTGAG
24251  CCCCTGGAGC TGAGGATGCT GGAGAGACAC AGGGGTAGGG GCGGGAGCAG
24301  TAACCAAGAC CAACTGTGAT AAAATAAATG GCCCAGCACT GCTGAAATTT
24351  TTGGTAAGAT ACAAAGAAAA TTGTTCTCAA ACATTGGATT GCCACTTAAC
24401  AAATGTGCTT TAATATTGCT ACCTGTGTAT ACGTATGTAT ACACATTTAA
24451  ATAGGTATTT GCTCTTTCTG ACAACAAAGT CAGAGATTGG GGTAGGAGCA
24501  TTGGGAGTAG GAACCTGTTT TAGACTTCTT CTAATATTTT TCAAAGATTT
24551  TTTTGGAAGC AAAACTTTAA AAAGTATTTT TTATTTGGAA ATAGTTTTAA
24601  ACTCATCAAA AAATGGTAAA AATAAAAATA TGAGGCATCT GTAAATTCTT
24651  TCCCCAGATG TACCCACTGT TCACATCTTA CTCCTTCTGC TGTATCATTC
24701  CTCTATCTAC ATATATCCAT AAATGTATAG GATATTTTT CCAGAGCACT
24751  TGAAACAACT TTTAAAAATA TTTGTTTAAC TCTTCAAACC GTTTTGGAAA
24801  CTTTCTTGCT AAGACTGCAT TTGCTGTAGT CAAAGCAGTA AGAAGGGGCC
24851  TAGAATCCCA CCTCCTTGCC TCTTCTCACC CAGGAGGACC TCCAAGTGAA
24901  GCCTGTGGCT TTGACAACTG GTTTGGAAAC CACTGTTCTC TTTTCATTGA
24951  AGGTCTCCTA AGACCGGATG CCATTTGTAG AGGCTCTTTT GATGGGCAGG
25001  TTTGGAGATG TGGGGTGAAC AACAGCATGG AGGCCACTCT GAGACCTGGC
25051  ACCAGTCCCA GGGTGGTCTT TGTTCTGTGG CCCAGAATCA GACAGAAATA
25101  CCACACCTTG TCCCATAGCC CTGTCAGTGG CCACACCCTT CGAGACCATC
25151  TACACAGGCC TCTGGAGCTA CAACTGCGTC CTCTCCTGCA TCGCCATCGG
25201  AGGCATGTTC TATGCCCTCA CCTGGCAGAC TCACCTGCTG GCCCTCATCT
25251  GTGGTAGGTG TTCAGAAAAG CTGACAACCA GGTTACTCTG GCTATTCCTT
25301  CCCCCCTTGT TTATGTGAAA CCCATGGGGA CCACTAATCA ATACTGTTCA
25351  GCAGTGACAG AAAGGCCAAT GGCTTGCGTC CTAATGCCAG TGCTGCCCTT
25401  AACAGCTGGG GATTTCAGGT CCCTTTTCTG TCAAATGGGA TCACAACCAC
25451  CGAATGGTAT TATACTTACA CAGTGTTGTA AAGTTTATAA GGAAATCACA
25501  TATGCATTTC CTTGTGTGCT AATGACAGCA TTCCTGCTCT CTATAACTCT
25551  TCATTCAACA ACTGTTTATA CAACACCATC AAGTGCCAGG ACCTAGTCTA
25601  GGTATAGAAG ATACCATGGT GACTACATCC TCATGAAGCC ACAGCCTAGC
25651  AGGAGAGAAG TAATTGCACA AATAATTACT AAGGCTGCAG CGTCCACAAA
25701  GGTTGTTGGA ATGATCCAGT GAGGTGATGT ACCAGGAGCA CTAAAAATCA
25751  TAACCACATT ATGGAAGCTC GATTTCCATA AACAGAGAAT ATGCTGCCAG
25801  AAGGGAAATC AGCCATAGTC CTTCTCATAC ACCTGTATCC CAGCACCATA
25851  CCCTGTTTATA TAAATATACA AACTCACTTA ATCCCCCCAA GAATACCACC
25901  AGGCATAGCC TGCCTGGCCC ATTTTACAGA TGAGGAAATG AGGCTCAGAG
25951  GGGCTAATTA ACTTGCCCTA GAAGATAGCT ATTAATGGCA AAAGGGAGAG
26001  TCAATCCCAG CCCCAGCTTG CCACCAGCTC TCCTCTCCTG GTATTGTTCT
26051  CTGGAAGCAG GACAGGACAT TAATAAATAA AACTAGAGTC AAGGAAACAG
26101  AAGACTAGCG TCTGGAACAG CTTCTCTTTT GTTTTTTCCC ACTTATGCTT
26151  GGAGACTGAG AATGACTTCC ATATCCCTTG TATCCCCTCA GCAGCCAACA
26201  TGAGGCTGGG CATGGAGACA GTGGACCTAG TAAATATTTG TCAAGTTAAA
26251  AGTGCCTGTT ATTTTGAGGT TCAGACTGTA ACTGCCTTTG GCCTTCAGAG
26301  AAGTGGCAGA TTCCTGTGGC TGGAATCATC TGGGAAGCCT ACAGGGGGAG
26351  GCTAGGGTTT ATCTCAACAC TTCTAGTAGG ATCTGAGTTG ACAAAGAGAG
26401  AGGGAAGAGG TGTTCCGGAC AGAGAAGGAG AAAGAGCAAA GCTGCAGGCA
26451  GAAGGAGTTT GTCCAGAGGC ACCAGCTACA TGGACGAGCT TTCCTGACTG
26501  TCCTCAGGAC CCAGCTCCCA TGGGGAACC CAGCTGCCTG GCTCCTGGGG
26551  ACTGGTTCAG GGGTCTAGTA AGGTTCAGCC CTGGTGAGAC TTGGTGAACA
26601  TCAAGCAGCA TCACAGCTGC TCACAGTCTT GAATAGGAGG GACCTTGGCA
26651  GGAGCTCGTA TAGTCTGACC ACTCTTCCCC TACAACAATC ATCCAGCCTG
26701  TACTAGCTCT TCGCTACCAT CAGCGTAGAC TAGCATATGA TGTGTATTGA
26751  CCCCTGACTC CATGCAAGGC CACTATGGAA GCAGGGAGGG GACAAAAGGA
26801  AATATATGTT TTAATCTCTG CCCGAGAAT GAACACTCTG GTGGGAGACT
26851  GGCCTCACCT GTCTACAGAG ATAACAAATG CCAGGCAAGC ATGCCAGCTG
26901  TCAGGGCATG GTGCAGAATC TGAGGCTGCA GGAGAGAGGG TGGGGCTCCT
26951  GTTCTTTGGT CTGGGGCTCC CTGGTCTGCA ATGGCAGTGG CTTAAGGGGA
```

FIGURE 3I

```
27001  AGGCCCTGGG AAGCTCACTC TGGTGATCCT TGTTCCTCCA CAGCCCTGTT
27051  CTGTGCATAC ATGAAGCAG CCATCTCCAA CATCATGTCA GTNNNNNNNN
27101  NNNNNNNNNN NNNNNNNNNN NNNNNNNNNN NNNNNNNNNN NNTATACTAT
27151  ATATATATAT ATATTTATAC ATATACAAAG ATATATATAG ATCAGGGTCA
27201  GCAAACTTTT TCTGTAAAGA GCCAGATAGT AAATATTTTC TGCTGGGAGG
27251  CCATATATTC TCTTTGGCAA AGTCTTTAAC CCCTGTCATT TATAGCATAA
27301  AAGTAGCCAT AGACAACGTG TAAATGAATG AGTATGGCTA TGTGTCAATA
27351  AAACTTTATT AAACAAGCAG TGAGCTAGAT TTGGTCCACA AGCTGTATTT
27401  TGCAGATCCC TGATAGAGAC AGTCTACATA CTAATGCTTA CAAACTGGTG
27451  GGCGGTGCAC AGGCCCAAAC AGACACCACC AAGTCCCTTG CGACATAGCA
27501  AAGGGGTTTT ACATGCTGGT GACAGCATGA AGACCCTCAG GAAATGGAGG
27551  ATACCCAGAA AAGTGACAGT AGCATGACTG GAATCAGGAG GACCTGCTCT
27601  GGGGCTGCTG GAGAACTAGG ATACCCAGTG ATGTGCACTA AGGGGTGCAG
27651  TTTTAAACCA AGACCCGCCT TCTACATTGT CTGGGAACTA TTTCTAAGGT
27701  TCACTCTTCT CCAACCTCTC ACTCTGTTGT TCTCTCATCT GCCAGAAAGC
27751  ACACCACTCT TGGACAAAGA AAAACTGATG ACCCTTCAGT GCTGGAGTTT
27801  TCCAGGCAGG AAGGACAGGG AGGTTCAGAG AATCCCAACG TTTGAAGGGA
27851  GTGTGAAGAT CAGGTGGTCC GATCCCATGA TGCATGAAAA CCTCTATAAT
27901  ATTAGGATAA GGGCTTCAGT TCTCTGCCGG GTTTCCAGAA CAGATTCAAT
27951  TACCCAAAAT GGAGGCAAGG CTCCCAAAGT ATTTTAACAA CAGATAACCA
28001  GAACCAGAGA CCCCACTCAT TGCACTAGAA AATCCCCTCC TGTCTTCATT
28051  AAGCTCTTTG AGGCTGTCCA CCCAAAGCAT TGGGTCTGAT TGGGGACTGT
28101  CTTTTAGCCA TGCTTACTGG ATCCCCAGGA GAGGAAAACT ATTTGGATAT
28151  AAAAAATTAT TTCAGCTGAT TTGGACAAGA TTATCGCTTT CTTTTCCCAC
28201  CAACTCCCCC CATCTCCCCC ACCCCTGCCA ACTCTTCACC TCATCTCACG
28251  AGACTGGAGA GCTCCTGGAG TGATCTTGTC CCACCTTCCC CAGGGCTTCC
28301  CCACCTCATC TACCTGCTGA ATGGGTAGGT AAAAAATCTC TAAACTTACA
28351  GATTCACAGC ACCAACATGA GGTTGCATGG GGCAGGCCA TGATGAGAGA
28401  AGAAGAAGGG TTTGGGGACC CATATTCTGG CAGTTTTTCT ACCATCACCC
28451  CAAACTACAA GCAACAGCTC TTGGCTGTAC AAATGAGAGT GTCTATGTTG
28501  AACATAAATA TGCAATCATT AAAGATGTGT CAGTTTGGAG AGAAAGGGAC
28551  TTTAGAGGAG GCTGTGTCTC AAACTCTTTT CCTATCTCAC CCATCTTCCA
28601  CTCTCCCTCT CCCAGTCTCT GCCCTCCCCA ACACTTTCTC CCATCTTTAT
28651  CTCCTCTCAT ACAACACTGA TGAATTCTAT CAGCCATGAC AGTCTTGTCC
28701  TGCTGCACTT TAAAATGGCA GATCTTAAAT CATCTTTCCA GTTTCTTCCA
28751  TAATTGACAT AGTCAAGTTT TCTGCTTCAT CTTGAGTCGA GCTTGAGCAT
28801  TTGCTAAGAT ATAATCAATT TTCTTTAGCT TTAAATGTTT GTGGCCATAG
28851  AGTTACTTAT AATGTTCTCA TAGAACAATT TCAGTCTCTC CTGTATGCAT
28901  GGTTTTATCC CCTTCTCATT TCTACTCTTA CATAATTTTG TTATCTCTTT
28951  TCTTTAATCA GGTTTGCAAG GAGTTCATTA ATTTTACTGA CTTTTTCAAA
29001  GAAGCGATTT TGGATTTATT TGTCCTTTCT ACTTGTTTTG GTTTGTTTTC
29051  TATTGATTTA TTTTTCCTGT TTCTTAAGG TTTAAATGTT ATTTTCTAAT
29101  GTTTAAAAAT TGATGTAGAA TTCCTTCATT TTAGGTCTTT CTAACAACAA
29151  AGCCATTTAC AGCTATTAAT TTTCTCCTGA GTACAGCTTT AGCTGGATAC
29201  TATAGGTTTT AGAATAAAGG AGTCTACATT TATCATTTTT AAAATAGTTT
29251  GTAATTTTAA TTTTTATTCC TCTTTGGTTG TTTGAGGATT ATTTAATAAT
29301  GGGTTTCTTA ATTTCTAGCA TTTAGGAATC TTTTGATTTT TTTAACTTTG
29351  TATATCTAGT TTTATTGGAT TATGAGCAGA AAACATGGCC TGTAAAAATC
29401  TTTATTTTAA AATTGTGTGA ATTTTTCTTC ATTGTCAAGT ACCTGATTGA
29451  TTTTGGACAT ATAAAATTAA ATTTTACTTT GAAAGAAATA CATATTAAAT
29501  TGATTTGTTA ATTGTATTAT TCAATTCTC TATGTTCTTA TTTTTTTGTA
29551  TATGGGTCT TAATTCTGAA AAGGGTTTGT TAAAAATCAA CTATAATTGT
29601  ACTGTTTCAT TAATCTTTGC ATTTCTAAAA CATTTACCTC ATATAATTAG
29651  TTACCACATT GTTGATGCC TATTAATTTA TGACAATCTT TTTCTTCAAA
29701  AATTTTGCCT ATTATTATAA GTTACCCTCT TTATTCTAGT TAATGCTTTT
29751  TTTTTTTTT TTTTTTTTT TTTGAGATGG AGTCTCACTC TATCGCCCAG
29801  GCTGGAGTGC AGTGGCACCA TGCTGGGCTC ACTGCAAGCT CCGCCTACCC
29851  GGGTTCACGC CATTCCTTCC TGCCTCAGCC TCCAGATTAG CTGGGACTAC
29901  AGGCACCCGC CACCACGACC AGCTAATTTT TTGTATTTTT TTGGGTCTCA
29951  CTTTGTTGCC AAGGCTGGTC TGGGCTCAAG TGATCCTCCC ACCTTGGCCT
```

FIGURE 3J

```
30001  CCCAAAGTGC TGGTATTACA GGCATGAGCC ACTGCATCCA GCCCTAAATT
30051  CTTTGACCAA CTACTGTGAC ATTGCAAATC CAGGAATATC AATGCCTTCA
30101  CTGGAGGGAG GATCTCCATC CTCAACGCCT GTCACATCCT TCTCCCCCAG
30151  AGTCCCCAGC CCAACACAGG AAACTAGGAA ACTTCTTCAG TCCCCAATGC
30201  TTTTGTTTCC AGGTGGGCGT GCCACCAGGC ACCTGGGCCT TCTGCCTTGC
30251  CACCATCATC TTCCTGCTCC TGACGACAAA CAACCCAGCC ATCTTCAGAC
30301  TCCCACTCAG CAAAGTCACC TACCCCGAGG CCAACCGCAT CTACTACCTG
30351  ACAGTGAAAA GCGGTGAAGA AGAGAAGGCC CCCAGCGGTG AATAGCCATG
30401  TTCGGGGAAG AAACGCTCTT TGCCTGACCT GATGTCCTCT CCCTGTGTTC
30451  TCTGCTCTGG TTCAATCAGT TGCAGCACTC ACCTTCTTTG CCTCTCCTTG
30501  CACCTGTGTA GAACCAAGCA CACCTGTAAC TTTCTTTCCC TGAAGCTGAT
30551  TTTCATTCTC TGCCAGAATC TCCATAACTA TCTATTGTGC GACATTAAGG
30601  GATGTTGGTA TTACAGTAAA ATTTCCGGAG TTAGCAATAA GGTGTGTGTC
30651  TTAAATGTTG TTGACTTAAA ACAAAAACAG TAGTCTTTTG GAAAGGTAAT
30701  TAACAGGTGA TCTTCTTGGC ATCTTAAACT AAATAATAGA TGCTATAAAA
30751  TTAAACTTGT TGAGTGGTTC CTAGGCAGAC ACAGAGTAGG GGGGTAAGTC
30801  AGGGGACACA GGCTAGGAAG GGAAGGCTCT CTAGTGGCTG AGCTAGAGAC
30851  TAATGACCAC AAAGAGAGGA ATTTCACACT GATGGGATTT TAAAGTCAAA
30901  ACAGGGACGA TTGGGGCAGG GAATTATCTA AATAAGGAGT CTTAACCATT
30951  CAGTGGTCTT TGTAAGGGGC AAGGCGATAT TCCATAGCAG GGAGGAATTA
31001  ATAAATTAGA ATCCTATATA TGACTTTATT ATGGAGGATA AGCATTTCTT
31051  AATTTAGGGC AAACCAGCAT CTCTTTAAAA TTAATTTTTT AAATTTTAAG
31101  TTCTGGGATA CATGTGCAAA CATGCCGGT
```

FIGURE 3K

FEATURES:

| | |
|---|---|
| Start: | 12789 |
| Exon: | 12789-12938 |
| Intron: | 12939-13806 |
| Exon: | 13807-13987 |
| Intron: | 13988-15081 |
| Exon: | 15082-15271 |
| Intron: | 15272-16924 |
| Exon: | 16925-17053 |
| Intron: | 17054-20897 |
| Exon: | 20898-21090 |
| Intron: | 21091-23654 |
| Exon: | 23655-23802 |
| Intron: | 23803-25118 |
| Exon: | 25119-25253 |
| Intron: | 25254-27043 |
| Exon: | 27044-27090 |
| Intron: | 27091-30212 |
| Exon: | 30213-30395 |
| Stop: | 30393 |

MAP POSITION:
BLAST match to HTG
LOCUS AC023421 162534 bp DNA HTG 08-APR-2000
Homo sapiens chromosome 18 clone RP11-116O18

FIGURE 3L

ALLELIC VARIANTS (SNPs):

| Position | Major | Minor | Context |
|---|---|---|---|
| 8,221 | c | t | gccattggtgctgcatgtctcgcccctaccccaaagccaaaattccccg[c/t]tgtaacagagtaaacattcccgtggcaaaggaacgctgtattccctagag |
| 11,751 | t | a | ggaggaggagaggtaatagcctagcgaaatggaactaatgcaaaattaga[t/a]aggggactttatcccttttgaagggaatcctgcaatccttgagcggtgt |
| 11,944 | c | t | catggagcacggagcaatggggaaagctctaggtcatactgagaggagac[c/t]gcatgcaggtccaaaaccacctctcaaataaataaataaaaagatataac |
| 16,706 | g | - | accacagacaaagtgcataattttaattgtcgatcagcaagacaa[g/-]ggtgtgtgtgtgtgtgtttgtgtgtgtgtgtgtgtgttatcaggaaag |
| 17,269 | g | t | gggtcatttggagatatggaataaggaggattctttttgttttttgtttgt[g/t]tgacacagagtcttgctctgtcgtccaggctggagtgcagtggcgcaatc |
| 17,548 | g | a | tgcctcggcctcccaaagtgctgggattacaggcgtgagccaccatgccc[g/a]gccaggaggattctttaaaccaacaaaagacaacattttttttattgcaa |
| 19,904 | c | g | ggaagaaagcagacagggtgtggatttttatggctgggaaaacaagcctt[c/g]tcatcttgtcacttctatttttcttaatgaagtaaagccaggtggttggtg |
| 24,723 | a | g | acatcttactccttctgctgtatcattcctctatctacatatatccataa[a/g]tgtataggatattttttccagagcacttgaaacaacttttaaaaatattt |
| 27,527 | g | a | caccaagtcccttgcgacatagcaaaggggttttacatgctggtgacagc[g/a]tgaagaccctcaggaaatggaggatacccagaaaagtgacagtagcatga |
| 28,024 | a | c | ccaaagtattttaacaacagataaccagaaccagagaccccactcattgc[a/c]ctagaaatcccctcctgtcttcattaagctctttgaggctgtccaccca |
| 28,335 | a | g | cttccccagggcttccccacctcatctacctgctgaatgggtaggtaaaa[a/g]atctctaaacttacagattcacagcaccaacatgaggttgcatgggggca |
| 28,789 | g | a | cagtttcttccataattgacatagtcaagtttttctgcttcatcttgagtc[g/a]agcttgagcatttgctaagatataatcaattttctcttagctttaaatgtt |
| 28,987 | c | t | tttgttatctcttttctttaatcaggtttgcaaggagttcattaatttta[c/t]tgactttttcaaagaagcgatttttggatttatttgtcctttctacttgtt |
| 29,500 | t | c | attttggacatataaaattaaatttttactttgaaagaaatacatattaaa[t/c]tgatttgttaattgtattattcaatttctctatgttcttattttttgta |

| Position | Allele 1 | Allele 2 | |
|---|---|---|---|
| 8,221 | c | t | Intron |
| 11,751 | t | a | Intron |
| 11,944 | c | t | Intron |
| 16,706 | g | - | Intron |
| 17,269 | g | t | Intron |
| 17,548 | g | a | Intron |
| 19,904 | c | g | Intron |
| 24,723 | a | g | Intron |
| 27,527 | g | a | Intron |
| 28,024 | a | c | Intron |
| 28,335 | a | g | Intron |
| 28,789 | g | a | Intron |
| 28,987 | c | t | Intron |
| 29,500 | t | c | Intron |

FIGURE 3M

SEQUENCE LISTING

<160> NUMBER OF SEQ ID NOS: 18

<210> SEQ ID NO 1
<211> LENGTH: 1359
<212> TYPE: DNA
<213> ORGANISM: Homo sapiens

<400> SEQUENCE: 1

```
atgtctgacc cccacagcag tcctctcctg ccagagccac tttccagcag atacaaactc      60
tacgaggcag agtttaccag cccgagctgg ccctcgacat ccccggatac tcacccagct     120 ctgccctcc tggaaatgcc tgaagaaaag gatctccggt cttccaatga agacagtcac      180
attgtgaaga tcgaaaagct caatgaaagg agtaaaagga aagacgacgg ggtggcccat     240
cgggactcag caggccaaag gtgcatctgc ctctccaaag cagtgggcta cctcacgggc     300
gacatgaagg agtacaggat ctggctgaaa gacaagcacc ttgccctcca gttcatagac     360
tgggtcctga gagggaccgc tcaggtgatg ttcgtcaaca atcctctcag cggcctcatc     420
atcttcatag ggctgctgat ccagaatccc tggtggacaa tcactggggg cctggggaca     480
gtggtctcga ccttaacagc tctcgccttg ggccaagaca ggtctgccat tgcctcagga     540
ctccatgggt acaacgggat gctggtggga ctgctgatgg ccgtgttctc ggagaagtta     600
gactactact ggtggcttct gtttcctgtg accttcacag ccatgtcctg cccagttctt     660
tctagtgcct tgaattccat cttcagcaag tgggacctcc cggtcttcac tctgccctc      720 aacattgcag tcaccttgta ccttgcagcc acaggccact acaacctctt cttccccaca     780
```

```
acactggtag agcctgtgtc ttcagtgccc aatatcacct ggacagagat ggaaatgccc    840
ctgctgttac aagccatccc tgttggggtc ggccaggtgt atggctgtga caatccctgg    900
acaggcggcg tgttcctggt ggctctgttc atctcctcgc cactcatctg cttgcatgca    960
gccattggct caatcgtggg gctgctagca gccctgtcag tggccacacc cttcgagacc   1020
atctacacag gcctctggag ctacaactgc gtcctctcct gcatcgccat cggaggcatg   1080
ttctatgccc tcacctggca gactcacctg ctggccctca tctgtgccct gttctgtgca   1140
tacatggaag cagccatctc caacatcatg tcagtggtgg gcgtgccacc aggcacctgg   1200
gccttctgcc ttgccaccat catcttcctg ctcctgacga caaacaaccc agccatcttc   1260
agactcccac tcagcaaagt cacctacccc gaggccaacc gcatctacta cctgacagtg   1320
aaaagcggtg aagaagagaa ggcccccagc ggtgaatag                          1359
```

<210> SEQ ID NO 2
<211> LENGTH: 452
<212> TYPE: PRT
<213> ORGANISM: Homo sapiens

<400> SEQUENCE: 2

```
Met Ser Asp Pro His Ser Ser Pro Leu Leu Pro Glu Pro Leu Ser Ser
  1               5                  10                  15

Arg Tyr Lys Leu Tyr Glu Ala Glu Phe Thr Ser Pro Ser Trp Pro Ser
             20                  25                  30

Thr Ser Pro Asp Thr His Pro Ala Leu Pro Leu Leu Glu Met Pro Glu
         35                  40                  45

Glu Lys Asp Leu Arg Ser Ser Asn Glu Asp Ser His Ile Val Lys Ile
     50                  55                  60

Glu Lys Leu Asn Glu Arg Ser Lys Arg Lys Asp Asp Gly Val Ala His
 65                  70                  75                  80

Arg Asp Ser Ala Gly Gln Arg Cys Ile Cys Leu Ser Lys Ala Val Gly
                 85                  90                  95

Tyr Leu Thr Gly Asp Met Lys Glu Tyr Arg Ile Trp Leu Lys Asp Lys
            100                 105                 110

His Leu Ala Leu Gln Phe Ile Asp Trp Val Leu Arg Gly Thr Ala Gln
        115                 120                 125

Val Met Phe Val Asn Asn Pro Leu Ser Gly Leu Ile Ile Phe Ile Gly
    130                 135                 140

Leu Leu Ile Gln Asn Pro Trp Trp Thr Ile Thr Gly Gly Leu Gly Thr
145                 150                 155                 160

Val Val Ser Thr Leu Thr Ala Leu Ala Leu Gly Gln Asp Arg Ser Ala
                165                 170                 175

Ile Ala Ser Gly Leu His Gly Tyr Asn Gly Met Leu Val Gly Leu Leu
            180                 185                 190

Met Ala Val Phe Ser Glu Lys Leu Asp Tyr Tyr Trp Trp Leu Leu Phe
        195                 200                 205

Pro Val Thr Phe Thr Ala Met Ser Cys Pro Val Leu Ser Ser Ala Leu
    210                 215                 220

Asn Ser Ile Phe Ser Lys Trp Asp Leu Pro Val Phe Thr Leu Pro Phe
225                 230                 235                 240

Asn Ile Ala Val Thr Leu Tyr Leu Ala Ala Thr Gly His Tyr Asn Leu
                245                 250                 255

Phe Phe Pro Thr Thr Leu Val Glu Pro Val Ser Ser Val Pro Asn Ile
            260                 265                 270
```

```
Thr Trp Thr Glu Met Glu Met Pro Leu Leu Leu Gln Ala Ile Pro Val
        275                 280                 285
Gly Val Gly Gln Val Tyr Gly Cys Asp Asn Pro Trp Thr Gly Gly Val
        290                 295                 300
Phe Leu Val Ala Leu Phe Ile Ser Ser Pro Leu Ile Cys Leu His Ala
305                 310                 315                 320
Ala Ile Gly Ser Ile Val Gly Leu Leu Ala Ala Leu Ser Val Ala Thr
                325                 330                 335
Pro Phe Glu Thr Ile Tyr Thr Gly Leu Trp Ser Tyr Asn Cys Val Leu
            340                 345                 350
Ser Cys Ile Ala Ile Gly Gly Met Phe Tyr Ala Leu Thr Trp Gln Thr
                355                 360                 365
His Leu Leu Ala Leu Ile Cys Ala Leu Phe Cys Ala Tyr Met Glu Ala
        370                 375                 380
Ala Ile Ser Asn Ile Met Ser Val Val Gly Val Pro Pro Gly Thr Trp
385                 390                 395                 400
Ala Phe Cys Leu Ala Thr Ile Ile Phe Leu Leu Leu Thr Thr Asn Asn
                405                 410                 415
Pro Ala Ile Phe Arg Leu Pro Leu Ser Lys Val Thr Tyr Pro Glu Ala
            420                 425                 430
Asn Arg Ile Tyr Tyr Leu Thr Val Lys Ser Gly Glu Glu Glu Lys Ala
        435                 440                 445
Pro Ser Gly Glu
    450

<210> SEQ ID NO 3
<211> LENGTH: 31129
<212> TYPE: DNA
<213> ORGANISM: Homo sapiens
<220> FEATURE:
<221> NAME/KEY: misc_feature
<222> LOCATION: (1)...(31129)
<223> OTHER INFORMATION: n = A,T,C or G

<400> SEQUENCE: 3
gaggaaaact gaataggttt gaagcttagc agaatggatt taatccaagc cctgtaatcc      60
ttaagctatg tacctggaca agtccctaac ctaaacaaag tccaccaaat ttccttgggt     120
gaaaatgggg caaatagtag gccccttttg cagctgttgt gaaggttaca tgagaaaagc     180
acatgaaaag gtttggcata cagtacgcgc aagagaagct aatccccccct cctccaacgt    240 gatccttatt tattgtaata atggccccta atctttagct acacctatat tgatcccta     300 tctatataat ctaacgcaca tgtgtattat tatattgtat gtgtgtgcac atgtgataca     360
tgagatacac tcacaaccgc ataggtaatc atactccaaa gaacacacac gtatgccacc    420
ccaggtgtac ccttcaatgt agggtcaaac ttaaagacgt ataaaacacc cacatacact    480
cactttagtc cgttggtact gtattaggac ctggcctata cagaattgtg aaaactgatc    540
cgatccctct gttgtgccat ggttaacagt acccacgtat gccatagatg tgtcctggcg    600
ccatctagtg ggggatccaa ctttctgctc catagtgcct ccttaggctg gctccagcca    660
ttgctccaac tcaccatttt gtaagctgcc tccatcatcc taaaaaacga ccatgctgaa    720
agagctcctc tgtatttctt ggcagaccct ttccagtttt catcctgggt gtttctgaac    780
aggaacatat ctcattgaag tatttgcacc tctacctaca gacaaggaaa aggcttggag    840
cacctccatt cattgtgcca acaggacctg aatgaccgtg agttgccctg catcatttat    900
aagtccatgt cttcaggatc tagaaggaaa actctgtatg ctgtaattat atggctttct    960
```

```
gaattcacta aatttaggaa tattttatat attttttttca ggagaaaata tattctttct   1020
ttcaatgaga atattgaccc acaaaaagac accaccagtc aattgtttca aagagatgag   1080
atggtactgg tcatccttta gctatgaagg aagccaagct ggttataggg aattgttact   1140
actataccta gattaaccca tgggattcaa ttttcatttt tttaactagg tagatttta   1200 tattcccaaa gccttaataa tagtggagaa atggcaggg cccttatggg ctctggccta   1260
tatagctaat tagttttgga aggtcttatt ccattcaaac gttaagggga ctgagtacct   1320
ggaaaaggtg aggggggggg aaaaggccgg gttaaactta ttggtgggta atagcccccan   1380 nnnnnnnnnn nnnnnnnnnn nnnnnnnnnn nnnnnnnnnn nnnnnnnnnc tgtgttattc   1440
aattggttgg atgtaagtca gagttcagcc cacactcaaa tggagtgatc acacagttat   1500
acaatggtga gaacacaagg gggtggggat caaagggaat catcttagaa tgtgtccacc   1560
acagagttga agtttattta ctggcaaagg atattcatta atatcttatt caatgaaaga   1620
aaaggtcaca aaacagcaag gacaatagga tccctgtttt gtaaactaag accgatagaa   1680
aatatatttg catgtataca taaatattca tgaaacactc tttaagtgtt cctgggttaa   1740
cagtagttgt atctagatgg tggaataaca gatgagtttt atgtcctgtt tccttatttt   1800
tttctttttt ttctgtaaaa ggaacatgta ttgtttataa tttttaaaag agtaaatatt   1860
attacctttt caagaagcga tttaaaccct caaggcttct ttattctgac ctccattctc   1920
tttacaggat tgtttcttgc ttactacttg tggtcaacta agtagagatt cataagacct   1980
ttatagaacc actgacaaca ctgtgaccaa ggaaactgtg agtatgttct agaacttgct   2040
tctgtgtttg tgtcttcaaa acagctgcta tcaccaataa ttaaaccata aaaaaccgaa   2100 attattttc cctctggggt gattacaacc acacgggagc tgtgatgaga ggtgagtcct   2160
gtgaagatct cctccttgag tcttcccac tccattctgg ttgcttccag acaagtggta   2220
acaataatca catgctcatc tcctctgaaa aatttaaaag ggataggttc tatttatatg   2280
tcaaaaatag atgaacagat ctgacactgc tgaacataat tgcaaatttg aaaaaggag   2340 agggaatggg tgagagaaaa gataaagcca ttaatagcct ccatacttca ttagttttcc   2400
ttcctcatgc caccagggga ggccctgagt tgggggtgcc actgatttgg ggttggaatg   2460
atttcctagc aatataaaag tttattcttt aaggtcactt gctgataaaa actactggtt   2520
tttgccaggc catcgattta ttgggttgtt tgacaaggcc agaccagctg ttctatactt   2580
atattaagcc caaagaaagc tgctcaagat ggatgccctg gcatcagtgn nnnnnnnnn   2640 nnnnnnnnnn nnnnnnnnnn nnnnnnnnnn nnnnnnnnc gcctgagtct gtgggagccc   2700
cccttcttgc atcaggcatg acctggaata tgagaccatg gagtcaaagg gagaattatt   2760
tttgagattt aagatttaat gcctgccccc actggatttt ggacttgcgt ggggcctgta   2820
gccctttgtt ttggccaatt tctcccattt gaaatgggag catttatcca atgcctcctg   2880
cacccccact gtatcttgga agtaactaac ttgctttttt tttttttttt tttttgaga   2940 cacagtttgc tctgtcaccc aggctggagt acattggcac tatcttggct cactgcaacc   3000
tccacctccc aggttcaaga gattcttctg tctcagcctc ccagtagcta ggactacaag   3060
tgtgtgccac cacaccctgc taattttgt attttagta gagacagggt ttcaccacat   3120
tggccaggct ggtctcgaac ttctgacgtc aagtgatcca cccgactcgg cctctcaaag   3180
tgctgggatt acaggcgtgg gccgccgcac ccggccattt gcttttgatt ttactggctc   3240
ataggtggaa gggacttgcc ttgcctcaga tgaaactttg gactttgact ttcaagttaa   3300
```

```
tactggaata agttaagact ttgggggact gttgctaagg cacaattttg ttttgaaatg      3360
tataaagaac ataatatctg ggaggggcca ggggcagaat gatatggttt ggctctgtgt      3420
ccacacctga atatcatctc aaattgtaat cccagtaatc cccatatgtt gagggcagga      3480
cccagggcaa ggtgactgga tcatgggagc ggtttccccc atgctgttct cgtgatagtg      3540
agtgaattct cacaagatct gatggtttta taagtgtttg gcaagttcct gctccacacc      3600
atctctctct tctgccgcca tttgagaagg tccaagtttc cttcccttc gccttccacc       3660
atgactgtaa gtttcctgag gcctccccag caatgtggaa gtgtgagtca attaaatttc      3720
tttttttttt ttttctaata aatcacccac tctcaggtag ttctttatag cagtatgaga      3780
atggactatt gcagtggggg agccaggatt tgaatccagg tattctgtct ccactgtgcc      3840
accactgtct aataacacta aaattaacta cctagagcca cctcgggca gcttgtgtat       3900
ataagtatgt gtgcatgtgt gtatgtgtag gggtgtatgt gtgtgtgtgt gtgtgtgtga      3960
gagagagaga gagagagagg gagagagaga gactactaca ttgtgaaata gtccaccaca      4020
caagccagag cagaggtcac catgctccta agaggccagg aaggcaccat ggccatgtta      4080
ggggtgggtg tgtgagcagg atgtgtgtga gtaaaggaga tcaatattcg tgcatgtggg      4140
aactgaattg gaggtagctg tgggacctca ggaggccacc tgcccagaac agtggcacac      4200
actgcagaga agctgaaaat tgtcttgggc acaagtggag caccctggg tagaaccgag       4260
ggagattgag aacagttgct atcttcagag ctttttaact tctcccccta agtagcctca      4320
actgatggga gaattgacac attaccccta cgtaataggt gggcacagcc tgaagcagcc      4380
acctgcagac tctacatttc ttccctttat attttatttt aataatataa agagttgcat      4440
ttgactattt tataaaccat gtttgcttaa atatacaact attattctat attagttcat      4500
atcaagctca atcagcattc cagaaaactg tgcttctcag tgccctgggc attgactact      4560
ctggctcaga gtttcatgcc cagtttcagg agcgaagcac tcagacatgg agcacctcag      4620
aaggttttg agcagtggca cgaccaagtc atgttttaag ataatttacc catcaccagt       4680
ggcaaggtgg agaaaaactg gggagactga agtgagggaa atcagctaga aggtgacctg      4740
cgttggggag ggcctggctt aaagggagat aatgggctga tccagactga gggctctgaa      4800
ggagaactcg atggctgaat aattgcaact gatggaatgc aagaggcaat aaataaattg      4860
ccatttattc atgggatgag agggctcaat atgtggaaca ttgaagggtc accccacttt      4920
agaagtgtca cataaggacc gggtgcagtg gctcacacct gtaatcctag cactttgaaa      4980
gaccaaggtg ggcggattgc ctgagctcag gagtctgaga ccagtctggg caacatgatg      5040
aaacccgtc tctactaaaa tacaaaaaat tggctgggca tggtggtgtg cgccggtagt       5100
cccagctact aaggaggctg aggcaggaga attgcttgaa cccgggaggt gggaggttgc      5160
agggagccga gattgcgcca ctgcactcta gcctgggcaa cagtggagac tccatctaaa      5220
acaaagaaaa aagtgtcaca taagaagggt gtgacgatct cctatgagat tcttccaaac      5280
acaagctaag gaggagcatc aaaagaggtc aagtggtctg ctctctcccc cacctcatct      5340
cacagccact gcaggctcct cagagctttt ctgctggagg ccagaattcc cctgccaggc      5400
tctggttaga ttctcagctg cagaacccca gccctggccc tgcagcagaa accagaaaga      5460
taaagcccct ggcccactgg ccaccagcca tctctaaccc cagccagtcc tcagaggacc      5520
cagaggaggt ggtgctgcct ctgactcctg ccccacccag cctgacccgc tggccccagt      5580
gagtcagtct cctctcagcc cagatcagac ttactaactt ggagctgcca agaaaactct      5640
gagccacccc taataaaagc cggcactcag ccaggctctt atacaaccca gccctgagta      5700
```

```
aggcacctct cagcccagct actggactgt ttacctgcct tgtcttctta gtgcccaggt    5760
gtctcctgga ttcctcccct ccctgatctc cctgatgtgt gatccaccag tccagggggcc   5820 tcatctgtcc ccattctggc agcctgacca aacatccacc tagccccaca cacctgattt    5880
ttcaccttca gagtctacca actcagggat gagtgaagcc agtgctccca gggacccagc    5940
ctgactcact cagcaaggtc ctttcagaat gatgctgtca ctgagatcct ggtggcaaga    6000
tggcagagag tctggggttg tgtttggtga gccagagtga aggacaatca agcagactgc    6060
cctagaaaaa tgaaggctta ggatcaacct ctgaagtgct cttaggtggg aaaaggagtc    6120
cctgtatcct gtgcaggtat aatggacaga actggaaaca gcaaagagaa aaagtcccag    6180
ggacttgatg tcagctccac agatacaagg gtttctagta agcagggctg ttctcaacaa    6240
gaccaacctg cctcatggga aggggaccc ccagccagga gaagctaggt atccagaggc     6300
gttaaagaat ggattccttc atcatttcag agagggacat ccctcttggt tctaaggttg    6360
tagaaattta tggaaactct cccttgcatc aattgcaagg tcttaggcaa aatatatcaa    6420
tccaactaat attctggaga acctgctaat cacttttact tctccagagc tgctgtggtc    6480
tcaataactg agttggttag aagatgaagt aaggccaggc acaatggctc acgtctgtaa    6540
tcccagcact ttgggaggcc caggccagtg gattacctga ggttaggagt tcaggaccag    6600
cctggccaac atggtgaaac cccgtatcta caaaaaatac aaaaattagc caggcgtggt    6660
ggcaggcgcc tgtaatccca gctactcggg aggctgagac aggagaattg cttgaacctg    6720
ggaggaggag gttgtagtga gccgagattg caccattgca ctccaagctg ggtgacaaga    6780
gcgaaactct gtctcaaaaa aaaaaaaaa aaaaaaaaa aagaagtagt aaatgggggcc     6840 atttgagatt catccccaga tgaccagggg actggtatac ttaagcccaa gagactaggg    6900
atagggagag agctttgact ctgcactaat tcacaccaac aactcaagaa atccctttga    6960
acatgggccc cttacatccc agggcagcag gagcatacga aataggcaca gcccctcttc    7020
actgggcatg ggcgtgtttc tgcaattcta ctggagatgg atgatcttta ggagaaaata    7080
atcaggaaaa gaatttcaaa attagtacaa tagagcagga gccacagttt ttctaaccat    7140
tggaagaatt tgggtccaaa cctagacact aaggactcct gacagtctgg ttctcacacc    7200
ctagttttgt ctttgattgc ctgctgacat ctctcccatg ctgtagcaga gtccatgctg    7260
ggacttgctt gcccaaacca tgtatttttct caggcatttc tctggagtgt gctcctctttt  7320 ctcacctgct tagccaagtc ctgacatgga agctgagccc agtctcccca gggctgggag    7380
ggcagggcag ccgctctgtg ctctctgcac cgccctcttg ccctctgccc ttgtgcctcc    7440
tgctcaggac acagtgcctg ctcactgctt tcctgggca ctcgaatgtg agccctttgc     7500
aggcaaggac tgggccttcc agcaatgatc cctccaggggt agcccacagg cgaacggtag   7560
atattcaaca aggagggttc ttacaaagag gatggaggag ctggtctgtt ttgggagccc    7620
cttgccagac atttgaggcc tggttttttgg agagacgtgg gactgatcca aacagcctct   7680
ctgtccatat ttctgaagga gaagaggagg tgtgggcagc caaggagagt ctgagtgcgc    7740
caagcagatc attatgtgtt cttggaagca ggtttaatgg actggcgctg agctgagctg    7800
ggaacgggct gaggccctca gcccggacgt ggctcgggca gggatttcac atccagttct    7860
aacaagtggc gacgccttat ggaaactttt gaaagctgtt ccgtttcaca ccagccagct    7920
tgtacttcat ctggctgctc ccaccctctc tccttcaat ttgggagcac gagaagaggg     7980
aaaagtaaga tcactaagcg cctactatgt gccaggaacc aagtcagcaa tttcactgtc    8040
```

```
ctgagaagcc tacgttgccc ttcggagaca tggaggccca cgcggccccg agtggcagag      8100
cagggaggca ggagcagccc cacctcacag cctgtgctcc ttccggatgc ggagacttgc      8160
tctccacagg gccattggtg ctgcatgtct cgccccctac cccaaagcca aaattccccg      8220
ctgtaacaga gtaaacattc ccgtggcaaa ggaacgctgt attccctaga ggaggtgcaa      8280
ggccctgttc ctgcagagga tacataggct tgagaaacac aacagcgggc tgaggccctg      8340
gacccaggcg ctcaagggcc agccactcgg ctgtgcatgg cccagccagg cagtcagagt      8400
aatggagagc gcagtgggga actgggtcta accttgactc tgcagcaaac tgctcatttt      8460
ctgggtcctg caaatgtcac aatgaggtga gcttgctctg gaaaatgctg agagcaacat      8520
acacatgaga aacaattcct attttgcttt tcaaggacat gatttatctg taaatggaaa      8580
tattgtctgc atacagaagg gactcaaagg tggagtacct ttttggagag taccctagaa      8640
agaacttccc ttgtgcaata ataataataa agggattttt aggtgtaagg ctttctgttg      8700
ggtggtataa atgcagaaat taacaaggta atggcccctg ttcttacagg gattataaag      8760
tagacacatt ttttttttcat caaagaaat ataaaaatct ttaaattctt acggttagga      8820
aataatttct gagtataccc attctcaact cctacctgta tacttcagcc ccaccactta      8880
aaagaacact atatttcctt gattatatga tgtatattat tttcatattt taacatttct      8940
aaaatcagga tgcatcttga aattatgaat ggaagcattt tcttctttct ttatgataca      9000
taaaatagtg atcaatctta cagctgataa catcttagat tccatgaaat atgtttagga      9060 aaaacccttta tcattaccac ttttcagcta gacttttaat agatttcata gccactgaat      9120
ttaacacaag gccttttccgg aacatatcta gttcatccag ttgtatagtg tcatgcagat      9180
tgtgtgtcta gatatctgat tgcccctgct tacttttcat atggttggct tggagggaaa      9240
tttttaccaa gggccaggga tgctgtatca cctcttggcc accagaggga gagagcgcat      9300
tggagaggaa caggttctgg ggcttgtcgg atttcactgt ctcctaaacc tttccagcat      9360
gccccctcta tggcagtgtg cccaccccctt actgaaaccc tacctacagg gtcagaatac      9420
aaggaaaggc ctccattccg gagttatggc agcatcaggg ttagttagat ctgaatgaca      9480
tttgcagacc tacacaaaaa ttcacagtgg tctaatgagc tcctcctggg aatgagaacg      9540
gtgctagaca tgacaggggg ttctgcctgc agaaaatgca tggctggtgg gtggccccac      9600
gctgttctga aaccactgga gatccctgag atccacagag atttgtaaag ttatgcagag      9660
aagtgttccc tatctatcag tcacctgtaa ccttgctcac agtcgcttcc tcccccccac      9720
ctcttccttc catatttatt tattgaaccc ttactacatg ccacacactg tgctaggagc      9780
tggggtcaaa gcaatagaca gaacagagga ggccaccgtc ctcatgaaac ctaagttctg      9840
gtgggaagat agaaaccata caaataaata tacaaatctg ctataaggaa aaatacctgg      9900
tcccatgaga gtatgtgaca ggagaacatg gtgggtggat ctgcgagggt ttatttagca      9960
agtgatcatt gagacaaagc ctggcagaag tgtaggggtt gaccaggaag agtgagggaa     10020
aggtcttcat gccaatgaac cagcacttgc agaggccctg aggtggaaag tgttcaacac     10080
cttacaagta ctaaaaggag gccagcatgg ggcctggagt catggagcca gaaagcaagg     10140
gactcactaa agcacagtgg cagctcagag ccttgcacac cctgtcaaag aggtagtttt     10200
ccatctgaaa gcattgatgg gctttaagca gggatccaac atgagattaa tatgcaact     10260 cttccctgcg gggcatggct ttgaggagaa acctgggaaa agtagggat atccaaatga     10320 aagtcattga agatgtggta agaggtgatg gtggctaact ggtgaccatg aacgtgaagg     10380 catattttt agagacagaa ttgttaaatt tagagagtaa gaagaaggga gcattaagtg     10440
```

```
tgactcctga gttttctgaa ggaatggctt ggaagggggaa gatgactttt cctaggtggt    10500
cacctgtgag ggaggatagg atttgggaag gcaacatgat gagttgtttt ggcaaattaa    10560
ggtacttgga acgtctatat gtgagtgtaa agtagacaac taaatctgtt aatccactgc    10620
tcaaaactgg gctggaaatg tgagttttga gggtcatcgg cagggagatg gaatacgaag    10680
ccatgctgag ggctgacgtc acctgggtag gagcaccagg gctgagaaga gggcccggaa    10740
cagggtctg caaaatgctc ctgttacacg aagaagagcc gccaaaagag agtgtgaagg    10800
agcaaccaga gagggagca gatataacgg ccaaagagtg tgtcaaagag ggtgatcaac    10860
tctcagaaca ccactgagca gcctggtggg atggggactg aaagtggact tgccatggag    10920
gccttagaga ccacagcaaa ggcagccata gcagaaagca gactgagctg gactaaagag    10980
agaaaaggga agcacctagt gttcacctga ggacagcaat ccaacttaca gtgaaagcaa    11040
tctactcggt tattcccctt gttctctagc catgttcagt tgtttggtga aagcatggaa    11100
aagttaggca tttgggttta tcccggctgg aatttcacca tacaagcatg agggagggag    11160
acaggtgcaa gagagttgga ggaagtaaca taagggggcca tgaagttaag ttggtcaagg    11220
agggaaggga agacaggtgg ttgtgggagc tgaagggctg tcagaggggt cacctgagca    11280
ggtgagccaa atgtgcaaga ggaagtggcc agagggagaga tctgactttt gagatttcca    11340
gtgtgtgtga tattaagccc atgctgggac tgtggaaatc agttgctgaa aaggggagat    11400
gaaaaggttc actggagatg agaaggacaa ggatctgaga agccagagaa caggatgatg    11460
agttatctgc ctggacatcg aagctgctta aagttactgg agggggatga agatgattag    11520
taggagcact tcaagtcttc tctgaatgac agagtgacca gagagtcagt aacgcagcag    11580
tgggcagttg gagaggatgg tatggccatt tgagataagc ctcaaagaag aagggtttct    11640
gcccaagcaa ggtgagtggt gctcagaaga aattgtggag agtaagaatt cctctcatta    11700
ggaggaggag aggtaatagc ctagcgaaat ggaactaatg caaaattaga taggggactt    11760
tatccccttt tgaagggaat cctgcaatcc ttgagcggtg tctggaatga tgagtatacg    11820
gaatggtagt acccatgtta gggatctgtg atccctgtcc taagagagac ggtcctacac    11880
tgaagggatg cagcatggag cacggagcaa tggggaaagc tctaggtcat actgagagga    11940
gaccgcatgc aggtccaaaa ccacctctca aataaataaa taaaaagata taactgagct    12000
ggaggaggct agagaagaaa tgcacaaatg gctgtatggg aaggagagag tacagcacta    12060
ccaaggggaa gccagacaaa accaggaaac tgaggacctc aggcaaagga tgttccaaaa    12120
gcaagtcatg gcataagccc tgaccctggt ggtacgggga caggagcccc atgtggaagg    12180
gaagctcctt cagctgggat gcacacagct catggaagaa tagaccagtg cttcctactg    12240
ttcctaggga agggaaagag ggaaggagct ggaaatggta gagggaagag aaggaagact    12300
ggagatcagt tgtaagcaat gtagcctcca tagaaattca ggaagagttt ctcttagaca    12360
ccccccacct ccaatcagta ctggatctgt gtgtacgtat caagggggaac atacgtgtac    12420
cactaactac cacaatagga cggcacagca ggcaatatga aaggcagaga aaaacactc    12480
agtgatcaag agaaaaagag agacttccat tctgactcag tggtcaggga tatcttcatc    12540
ggccaaatgg acattcttct ggacgcggaa gaatgggagg attttgaaag gtaatgaggt    12600
agagaaatgt cctcaactct acagcacaag ctgtagatcc cacgtgtgtc actgtccaac    12660
ccccaggaca gacctgaggt ctgagtccag cctcagccaa gtccctctgg gccccgtcct    12720
gactcactag ctctttccct ttccttccgt ctagtccatc gatagaagag tggctgtgac    12780
```

```
ccgaaggaat gtctgacccc cacagcagtc ctctcctgcc agagccactt tccagcagat    12840
acaaactcta cgaggcagag tttaccagcc cgagctggcc ctcgacatcc ccggatactc    12900
acccagctct gcccctcctg gaaatgcctg aagaaaaggt gagaagtgtc cctcctagga    12960
tgtttcctgg gagggagggg atgggaaaag tgggggcaaa agatgccgct ttcccacctt    13020
cccagtgaac ttagcacact gaggaagtgc cactgtcagt acatggtgac acccatggtg    13080
ggtcctacct ggccttagat aatgtggctc ttcatgagac atgattttaa ggacaagtac    13140
agaatacaga cactcactca ccagtctttc aatcagtctc taaaatcttt cccttaaac    13200 ctgctccctt gaactaccct actgtctcca agggaaggc ctttgttgaa atgcaggcca    13260
ttagcatcct cggtggtagc acagaggtag actggctggc cactgctgca gtagagaggg    13320
actcaagact gctgggatgg ccttccagag ctgtcctgac ttgcgatgag gaggtcccat    13380
atctttactc atcactactt tgaaattaca gaaggtattg gatctgctgt gcatacatgt    13440
gtatcttaat ttttagtaag attataactg catttcagta taattggctt ggtttgccgt    13500
cctatttatc tgatctttgc atttacaaac attattctga aaagaagctc atgggcttca    13560
ttaaactgcc aaaagagatc catggcacaa aggtgaagaa atcctgctgt gaagaaggtg    13620
catggtcctg ggaagaacag gcttgtacgg ggcactctat gcagccgcag acaatgggca    13680
tgtgttccac cctttgtctc atgatccttt atttttatca aaaacctgc caccctcctc    13740 tatccccaaa tgtccctgct ctcagaaagc tgtatcattt gatgtctggt tggtttctcc    13800
taaaaggatc tccggtcttc caatgaagac agtcacattg tgaagatcga aaagctcaat    13860
gaaaggagta aaggaaaga cgacggggtg gcccatcggg actcagcagg ccaaaggtgc    13920
atctgcctct ccaaagcagt gggctacctc acgggcgaca tgaaggagta caggatctgg    13980
ctgaaaggta ggaaaatacc ctggggagag gcagccagac caggccaggc cagagagaca    14040
accctctctc cggtttggtc caaagcttct ccctcactca ttcaccctca ccctgggtgg    14100
atctgcccag gactggacct cacccagggc tggagtccac agctggggga acttcagccc    14160
taagctgact ccaaggggat atgatatacc ctactggcct ggaattctca tggtttcaga    14220
attaaatgca ttgatcttag ttctttgcaa attgctcgtt cctatgtgaa atagatatag    14280
gacaaccata ttagcaacat ataagccatt tcccaagcta gctgaatgat cattccttca    14340
ctcgattcac ttgttgcaca gccatttatt atgtgcctgc tatgtgccaa gaaaatattg    14400
gtatcatcct tcccaaagct tcaggattct ttccttttaa cttctcgaac taaacactga    14460
aaggaatgcc acacccttca ctcccactag ccccgacacc tgcaccagtt gtcatggaaa    14520
ccaaaccagc aaatgaggca gaatgtacgc ccctctccta tacctggcct cctccaggcc    14580
ctgactcagt actgattttc acagctgggc tacaacaatt tcttccctag tgtcttttct    14640
tcaggctact ttcttgctg ctcagatacc agcccttaac tgagtcatcc agcactacag    14700
aaaaaagaat ttcctgcccc caccccccca ccttccccac ccttcttttt ggaccaataa    14760
atttcccttg gaatgctccc ggggcttctt ttccaaccaa gccagtggct ggaacagcgt    14820
taaattgttc tcagcatggt gcctctgtct atatggcaaa aactaccacc cactgcagaa    14880
tgattgctgg gctactgaga gatttgggct gggcaccagc ctcccctcta cccccacccc    14940
tccaccccga ccctggcct ggctgaatgg gaagggtcct ggcttgcaca ttcctgtttg    15000
ccttggttgc catgccaacc agcagttcag cagagcagcc caagctggac ctgctgatgg    15060
ctcgctctct gtctctttca gacaagcacc ttgccctcca gttcatagac tgggtcctga    15120
gagggaccgc tcaggtgatg ttcgtcaaca atcctctcag cggcctcatc atcttcatag    15180
```

```
ggctgctgat ccagaatccc tggtggacaa tcactggggg cctggggaca gtggtctcga   15240
ccttaacagc tctcgccttg ggccaagaca ggtgggtccc tctctatagg gattttagca   15300
agatgtgtgg aacagaaagt agagaggtgt ttacttgagt aatcagtcaa ccttaccctc   15360
ccagccagcc aaagtctcct gagtatcaac tttaagcagg tcactgacag tccttgcaga   15420
attacactgc tcctgctcac agcatgtgac agtgtcaaca ttcattttga ctgtggagac   15480
ttctgcaaaa cactgcctca gagggaggtg cagaggaaca gctaagctgt tctttccttc   15540
acagagccta ccattttagt tgaaaggaaa caagaattnn nnnnnnnnnn nnnnnnnnnn   15600
nnnnnnnnnn nnnnnnnnnn nnnnnnnngt gctggaaagc gtattccctt cctgcatctg   15660
caggggagcc ctaagcttcc agaagcttct gccatgcaag gaacagccaa cacatggtaa   15720
ggtttagcac gcccacatta ttcattcaac aaatactagc tgagcaccct ccatgcacag   15780
atactcttga cattgctggg ttactgggcc acagcaacgg acacacagac acacttcagc   15840
cctcatagaa ctaaggcagg tgcagaggga ctgaccacaa gcacacacag gtcactcctt   15900
ggcaggggcc ttgcatcaca agctgcctat gcccctccct cacccacagc ctatgcccct   15960
cacccggcag agcaattaga aaggtcaagg acagtgttta ttacgatcag gaggagaatt   16020
gtaggtgcat acaccagctt ctcctctgaa aaagaaggag tggctagact catgcttgga   16080
tactaccaca cttctgggct gctcctcacc aagggcacc tgggaaccca agctaaacc     16140
agcttattca ctctgttgca gacatgcaga gagaaagtac acagattcca gctacagaga   16200
atttttgtt tttgagacag ggtcttgctt tgtcacccag gctggactgg agggcaatgg   16260
tgagatcttg gctcactgca gcctcaactt cctgggctca agtgatcctc ccaccttagc   16320
cttccaagta gctgggacta caggcatgca ctatcacgcc tggctaattt ttgtattta   16380
gcagagatgg ggtttcacca tgttgcccag gctggttgaa ctcctgggtg caagtcatct   16440
tcccaccttg gactcccaaa gtgcagggat tacaggcatg agccactgag cctggccaac   16500
tacagagaac tttacacaat gtaatcataa cactctttct ccttccctct cttctctctc   16560
cctcactccc acacacaact tccttgtgtc acacctcagg tttctattat attccctcta   16620
tatttagcag tctaagtctc cctgataaa gaagagctta accacagaca aagtgcataa     16680
ttttaattgt cgatcagcaa gacaagggtg tgtgtgtg tgtttgtgtg tgtgtgtgtg      16740
tgtgttatca ggaaaggtgc tggcagctat gtgactgccc aatattcatt gagcgaactg   16800
acttttttct aagcattatt attaaaggaa tcatctaaat taagcatatc ctcagagcac   16860
caggagggag gggcccagta acaccaccaa cttcaaatgc aaaatcagtc tgtttcaccg   16920
ccaggtctgc cattgcctca ggactccatg ggtacaacgg gatgctggtg ggactgctga   16980
tggccgtgtt ctcggagaag ttagactact actggtggct tctgtttcct gtgaccttca   17040
cagccatgtc ctggtgaggc acctcatttt ttctgctcac agctccatgg ggcccccaag   17100
acttgtgt cttatactgg ccagagacag gacatacaca tgtgggaccc agccccttca     17160
tagccaagtt agcttgtctg acaccatgaa agcccatgag ttctcttgta acacaagggg   17220
gtcatttgga gatatggaat aaggaggatt cttttgtttt ttgtttgtgt gacacagagt   17280
cttgctctgt cgtccaggct ggagtgcagt ggcgcaatct cggctcactg caagctccac   17340
ctcctgggtt cacaccattc tcctgcctca gccacacaag tagctgggac tacaggcacc   17400
cgccaccacg cccagctaat ttttttgtatt tttagtagag acagggtttc actgtgttag   17460
ccaggatggt ctcgatctcc tgacctcgtg atccacctgc ctcggcctcc caaagtgctg   17520
```

-continued

```
ggattacagg cgtgagccac catgcccggc caggaggatt ctttaaacca acaaaagaca    17580
acattttttt tattgcaatg gtaatcttcc tgaacgacat tcttagtaat aaaagtcagc    17640
atttcctaag ttattcctac atgcttgaca cagtgctaag cagggcttat gcagtgctaa    17700
gtatggctac atttgccatc agtttatgga agggaagacc aaggcatgca gagattaagt    17760
cacttgcccc aagttgtact ttgtggtagt ttttgatgct ggcattccaa atccaatctg    17820
cactattaaa ccccaggttg catgggaatt gtctattatg tgacgtaacc aagacctaaa    17880
agctgaaaac ctgcttgtga tagaagcaga gagctttctt ggaacagaat atttatatgt    17940
aaagcataga acctttgaac tggaagtatc ggttgagatc ttgctgggca atcaccctca    18000
tattctagat gaaataagaa ggtcaccatg aaagggagtt aggaacaaat attcacctag    18060
cgaagggtgt gctgggccat tcacacaatg attcttagtt cacgtaaatt tacagcaggt    18120
ctatcaagca tcttggggt ctctgcagtg tgctcactgt catggggaac ctttgtcccc     18180
ccgaacccct gacttcacat ggtgtatacc acccctgttc tcaactttcc ttcaaacagg    18240
ggtgatttta ttcttattgt cagccaataa atcagacagg aggatttact ttttaacttt    18300
ctaagaggta aaggtctttc cttgggtttc aaagtctggg agtcctaaag ccaggctgtt    18360
aagtttagct tacctcctcc tttatatact ttattagaag tgcttgccaa aaaannnnnn    18420
nnnnnnnnnn nnnnnnnnnn nnnnnnnnnn nnnnnnnnnn nnnaaagac caagaaattg     18480
ggtttggcca aaaagcccca agtaaaagaa aggaaggagt ggcccaggaa ggggaagggg    18540
ccagggtacc tcggaatgaa gaggtccagg acccagggta caccctgta gaccccagg      18600
taaagccttt tggaatttct aatatccagg ctggtgatag aaaagcagtt aagaagagtt    18660
tttaggccag aagaatgtga tgggatatg gtttaaaatc taaaccaaaa tcacttctgt     18720
ttgcaggatg ggagaccgga ttttaactgg aagtaagagt ggatgctgga agcatctgct    18780
acaataatcc acaattgtct gctacaaaac cccacagaga tgacagtgtt tagattagag    18840
tgatatccat gaacatggta agaagtgagt gggtctgggg tatattttaa agaagataga    18900
ggcaatataa cttgttggga ggttgtggaa accaaggag aggaaaaaaa aaagaaaat     18960
tgaatacact cctttaattt gcctaagtac ctaggttgat acaaaagacc aagagaagaa    19020
ctggtcggtg gcaggagaca ggatacaaat caagaattct gtttggacac attatactat    19080
agacttccaa gtagagatgt tgtaaaggca attggatgta caaatctgaa acagtgatat    19140
gatcaagatt tgggaggtgg aaacacacag aagctttcat ctatggtact aaaggctatc    19200
acccaacaga gaagattttt tagaagagag agaaaatatt caagacagag tcccataggc    19260
tcttccaaca tttagaagtc tggcaagaga ggggaaaaac catcaaaaga gactaagaag    19320
gaacaggcaa aaagaaaact aagaaaatcc agtgtcatgg tagcccagac aaagtatttc    19380
aagatggtgg gcaggtccaa ctgtcaaagc aatagggaat gaccatggac ttagcaagat    19440
agatgccatt ggtgaaatgg acaagagcca tttccatggt gtaatgaggg cacacacctg    19500
actgaagtgg gtttgggaaa gactaggaag agaagattg gggatagcac agaaagccaa     19560
ccatttcgag ggctactgcc cgaagggag cagagaaacg gagccacagc tggagtggcc     19620
atcaggttaa aggggaaga tgtttaaagg tagaagatac tagagcatgt tatatcctga     19680
tgagaatgat ccaagaaaa agaagagatt gaagctgcag gagagaaatg agaaaattac    19740
aggaatgaag tccctgaggc agattagatc caaagaacag ggaaaagaac tggcctgatg    19800
aaggagcagg gatgcttcca ttatgtgaaa aagacagaga ggcagatttt gtgggaagaa    19860
agcagacagg gtgtggattt tatggctggg aaaacaagcc tttctcatct tgtcacttct    19920
```

```
attttcttaa tgaagtaaag ccaggtggtt ggtggaggct aaagggaagc agacagtaaa   19980
gatttgagaa gaaaggtgaa aatgtgaaat acttgtctca gcaagtcgga gagttaactg   20040
gtgagggatg tgtaggaggg ttttcaggaa gtcttaaacg ccttttttgaa attcatggtc   20100 attcattaaa agcagacaat ttaaacacat catgcaactt caggttttgc ccagcaggtc   20160
actgagtgtg gatgatgtgg ggtatttggt gtctagggtg gctggtgcct tccagaggaa   20220
actgaagcta agggagatta attacctaac attgttcctt cagcctgtat gcataggagt   20280
gagtcaggat ttgcactaag cttcatctgt ctccaacacc cattctcctt ccaaggaaaa   20340
gatgaagaag acagagggta caaacaactg aaggttctat tttcccctgg cagtttccag   20400
agtagctcta agtattttg ctgaaactag acctgcaaat tacccatatg ccattgcagc    20460
ctcctcctag aaggtcagtc ttctaaaatg ttatcagagc cttgaacaat agtcattgta   20520
caccttggtg attcaaaggc aatacattac attttgttta gttttcttgg tttaaaaaac   20580
aaggaaatat ttccactatt ttataaagtg ttttactcaa aataagttac gatattttta   20640
aaatttgttt ctcagaggtg taagcttatg aagcagatga caataaattg gcaaaaaaaa   20700
aagaaaaagg taagagctga aattgaatac cttattctat tccctatccc agatcattgg   20760
aacactggag tctcaagggg gccaggaatg ctgtgcctag gagaggaggc agtggatgat   20820
acagtggcca gagctgctga gacaatgtag acctcaggat gtcacaggga ttaaccctct   20880
gtctcttgca tcttcagccc agttctttct agtgccttga attccatctt cagcaagtgg   20940
gacctcccgg tcttcactct gcccttcaac attgcagtca ccttgtacct tgcagccaca   21000
ggccactaca acctcttctt ccccacaaca ctggtagagc ctgtgtcttc agtgcccaat   21060
atcacctgga cagagatgga aatgcccctg gtaagttacc cagcggtgat gagttgagac   21120
ccccatattc cactgcagac cttctcgcca accaatttgt ggactatgcc atgctctcaa   21180
cttctctaga aacatctata ccagatgatg ggcctcagca gggtatcaga aagggttgct   21240 gcccacatcca tagatccttt caacagtact tattgagcat gtaacatggc ctggacactt   21300
tttcagatac tgataataca agacaatgac atcctgctct taggaagcct acattctata   21360
cggggaaaca gataacatgc aagtgaacag ataagcgttg acagtacaga actgtggtgg   21420
ttgagtgaaa gatattagat aaaatgtata gtcagataaa ggggcaagat actaaaataa   21480
acatttaaaa ttgggatttt aaaggcatta gcatagaaga cagagggtta atttttatat   21540
actctctctc ttagtggttc tcaggcaggg ataattttgc cccttggaga cattaggcaa   21600
tgtctggaga catttttatt gtcaagacta gagaggtccc cagcacgctg ctcccaggcc   21660
acttccctct ttctctttga aacaacagag aaaggcttc cttttccttt ttgtttaatc    21720
agcttattgt tgctatataa gaattatgag gagtgtgaag aaggcctggt gcttagtaaa   21780
tttccatggc acacctgact gcccttcaca ccagggtgtc agctgcggcc tgggagcagc   21840
gtgctgggag ggaaggccgc cctggggcac agctcaccag gctgaaatat agatcccagc   21900
ggaggaagct tcattctaaa cccaggctcc attccaaggc cactcattcc ctcattcctc   21960
tcattcttga ccgcttgggc ttaaaatctg cgttcccgga tggaaggtg gacgtgaact    22020 cccctcagca tcccgcattc ctcagatgtt ggcaatcatg ggatatttat taaatagact   22080
tccagcctgt tcccaacatt taagctgagt tccctggtct ggtacaaagt gttttctggg   22140
tttctataaa taaatatgat tgagtacccc tccttgcca ttcctttcgc aagattataa    22200
actctggtcc aaacagcatt tggttattaa aagaccattc attcagagac aagagtgagc   22260
```

```
aaagtttaag agccctctag gctcttcaaa tactactccc tgaagaaatc atacttattc    22320
cagaattaaa tcaaattgtc aaaaagtaca aaatttggtc caaagggaga aactaaatta    22380
ttcccaacat ctacagcaac gtctacagta gatcatctat aactaatctc ccatcgcaca    22440
ctagactcac ctgaggacct gccatgcccc atatcaatta aatcagaatg tctagggaag    22500
agctgggcat cagtatttgt ttaaagattc cagggggatt ccactgtaca gcaaagtttg    22560
ggaaccactg acctaatcaa ttcctatttg ttaagcacct atggtgtacc tgggcataaa    22620
gggccctgtc ctcacagagg tcatgtgacc tggcaatggt gaaaagaact acagagtctt    22680
aaagctggaa gatcatctgc caagccagcc tcttgttaca gacgaggatg tgacatgctc    22740
acagtcacac agtgaactgt gcagagccct gatggaagct agagccctct actcccaggc    22800
cagtgctctg cctgccctgc cattctccct cctttctttt tctgccctca aaggactcca    22860
aaaatatcga caattcagcc tggccacaga aaagccatct gtcagcactg ccaaacaaat    22920
tatccccaat tccagcacca agttactctc aggctcaggg atgtctgggc ttcaggccat    22980
tctccagatg tgccacatac tacctttcta caatgctatg cggtcttcga gagcagggag    23040
catgcctact gctccctttcc aaaggctcac aaccccccag ggtagcagtg aatgggcagg    23100
ggccgccaaa gaggacgtgt cagcagtggc ttgacaaaga gacagcaagg gtgacaaaga    23160
cctcagacct gagctagggg tcaagctcag agcctctagc ctgcacttga ccaacaacag    23220
gctgggtgac ttttagtcaa atcatacatc aaaatggcct actgtatttt caatattcct    23280
agaatatttg tatggatttc agaaggtcta gaggaaatcc ccgagagccc tgaaactccc    23340
agcggcattc tagggaggag gtgcattctg gtcccctcaa agcagaagcc gtatgttcct    23400
cagaagcatc catgcccagc ccatgttggg ggccctggct ttgcatgagg gatgctcaca    23460
tgcctgctgg gtggtagagt gaggagctgt ttgttccagc tcatgcctcc catgttctct    23520
cacatgctgg agggtacagt catcctcccg ttccactcca ttactccccc gaggaatggc    23580
tcaaatctgg ccctgagtct ggttttttgca ttattgtcca tgctccagtg acctgtattc    23640
tgttaacttt gcagctgtta caagccatcc ctgttgggt cggccaggtg tatggctgtg    23700
acaatccctg gacaggcggc gtgttcctgg tggctctgtt catctcctcg ccactcatct    23760
gcttgcatgc agccattggc tcaatcgtgg ggctgctagc aggtaggaca gagctccctc    23820
tcttcaggtc ctcaggataa ttcactcaag gtcacttttc ccctacatac agcaaatctt    23880
ccagacattc tcttccctgc agtttttaaat actttcaggg agacaggcac ggtgacttat    23940
gcctgtaatc ccagcacttt gggaggccga ggcacataga tgacctgaac tcagggtgaa    24000
aacccatctc tactaaagaa aaaaagtac aaaaattagc tgggtgtggt ggtgggcacc    24060
cataatccca gctacttggg gagctgaggc aggagaatcg cttgaaccca ggaggtggag    24120
gttgcaatga gccaagatcg taccacctca ctccagcctg ggaaatagag tgagactccg    24180
tcttaaaaaa aaaaaaaata catgtggaga gatgcaaggg ggtaagaacc aagttggcct    24240
gcaaactgag cccctggagc tgaggatgct ggagagacac aggggtaggg gcgggagcag    24300
taaccaagac caactgtgat aaaataaatg gcccagcact gctgaaattt ttggtaagat    24360
acaaagaaaa ttgttctcaa acattggatt gccacttaac aaatgtgctt taatattgct    24420
acctgtgtat acgtatgtat acacatttaa ataggtattt gctctttctg acaacaaagt    24480
cagagattgg ggtaggagca ttgggagtag gaacctgttt tagacttctt ctaatatttt    24540
tcaaagattt ttttggaagc aaaactttaa aaagtatttt ttatttggaa atagtttaa    24600 actcatcaaa aaatggtaaa aataaaaata tgaggcatct gtaaattctt tccccagatg    24660
```

-continued

```
tacccactgt tcacatctta ctccttctgc tgtatcattc ctctatctac atatatccat   24720
aaatgtatag ggatatttt ccagagcact tgaaacaact tttaaaaata tttgtttaac    24780
tcttcaaacc gttttggaaa ctttcttgct aagactgcat ttgctgtagt caaagcagta   24840
agaaggggcc tagaatccca cctccttgcc tcttctcacc caggaggacc tccaagtgaa   24900
gcctgtggct ttgacaactg gtttggaaac cactgttctc ttttcattga aggtctccta   24960
agaccggatg ccatttgtag aggctctttt gatgggcagg tttggagatg tggggtgaac   25020
aacagcatgg aggccactct gagacctggc accagtccca gggtggtctt tgttctgtgg   25080
cccagaatca gacagaaata ccacaccttg tcccatagcc ctgtcagtgg ccacacccctt  25140 cgagaccatc tacacaggcc tctggagcta caactgcgtc ctctcctgca tcgccatcgg   25200
aggcatgttc tatgccctca cctggcagac tcacctgctg gccctcatct gtggtaggtg   25260
ttcagaaaag ctgacaacca ggttactctg gctattcctt ccccccttgt ttatgtgaaa   25320
cccatgggga ccactaatca atactgttca gcagtgacag aaaggccaat ggcttgcgtc   25380
ctaatgccag tgctgccctt aacagctggg gatttcaggt ccctttttctg tcaaatggga  25440 tcacaaccac cgaatggtat tatacttaca cagtgttgta aagtttataa ggaaatcaca   25500
tatgcatttc cttgtgtgct aatgacagca ttcctgctct ctataactct tcattcaaca   25560
actgtttata caacaccatc aagtgccagg acctagtcta ggtatagaag ataccatggt   25620
gactacatcc tcatgaagcc acagcctagc aggagagaag taattgcaca ataattact    25680 aaggctgcag cgtccacaaa ggttgttgga atgatccagt gaggtgatgt accaggagca   25740
ctaaaaatca taaccacatt atggaagctc gatttccata aacagagaat atgctgccag   25800
aagggaaatc agccatagtc cttctcatac acctgtatcc cagcaccata ccctgttata   25860
taaatataca aactcactta atccccccaa gaataccacc aggcatagcc tgcctggccc   25920
attttacaga tgaggaaatg aggctcagag gggctaatta acttgcccta gaagatagct   25980
attaatggca aagggagag tcaatcccag ccccagcttg ccaccagctc tcctctcctg    26040
gtattgttct ctggaagcag gacaggacat taataaataa aactagagtc aaggaaacag   26100
aagactagcg tctggaacag cttctctttt gtttttttccc acttatgctt ggagactgag   26160
aatgacttcc atatccctttg tatccctca gcagccaaca tgaggctggg catggagaca   26220
gtggacctag taaatatttg tcaagttaaa agtgcctgtt attttgaggt tcagactgta   26280
actgcctttg gccttcagag aagtggcaga ttcctgtggc tggaatcatc tgggaagcct   26340
acagggggag gctagggttt atctcaacac ttctagtagg atctgagttg acaaagagag   26400
agggaagagg tgttccggac agagaaggag aaagagcaaa gctgcaggca gaaggagttt   26460
gtccagaggc accagctaca tggacgagct ttcctgactg tcctcaggac ccagctccca   26520
tgggggaacc cagctgcctg gctcctgggg actggttcag gggtctagta aggttcagcc   26580
ctggtgagac ttggtgaaca tcaagcagca tcacagctgc tcacagtctt gaataggagg   26640
gaccttggca ggagctcgta tagtctgacc actcttcccc tacaacaatc atccagcctg   26700
tactagctct tcgctaccat cagcgtagac tagcatatga tgtgtattga cccctgactc   26760
catgcaaggc cactatggaa gcagggaggg gacaaaagga aatatatgtt ttaatctctg   26820
cccgaagaat gaacagtctg gtgggagact ggcctcacct gtctacagag ataacaaatg   26880
ccaggcaagc atgccagctg tcagggcatg gtgcagaatc tgaggctgca ggagagaggg   26940
tggggctcct gttcctttggt ctgggctccc ctggtctgca atggcagtgg cttaagggga  27000
```

-continued

```
aggccctggg aagctcactc tggtgatcct tgttcctcca cagccctgtt ctgtgcatac    27060
atggaagcag ccatctccaa catcatgtca gtnnnnnnnn nnnnnnnnnn nnnnnnnnnn    27120
nnnnnnnnnn nnnnnnnnnn nntatactat atatatatat atatttatac atatacaaag    27180
atatatatag atcagggtca gcaaactttt tctgtaaaga gccagatagt aaatattttc    27240
tgctgggagg ccatatattc tctttggcaa agtctttaac ccctgtcatt tatagcataa    27300
aagtagccat agacaacgtg taaatgaatg agtatggcta tgtgtcaata aaactttatt    27360
aaacaagcag tgagctagat ttggtccaca agctgtattt tgcagatccc tgatagagac    27420
agtctacata ctaatgctta caaactggtg ggcggtgcac aggcccaaac agacaccacc    27480
aagtcccttg cgacatagca aaggggtttt acatgctggt gacagcatga agaccctcag    27540
gaaatggagg atacccagaa aagtgacagt agcatgactg gaatcaggag gacctgctct    27600
ggggctgctg gagaactagg atacccagtg atgtgcacta aggggtgcag ttttaaacca    27660
agacccgcct tctacattgt ctgggaacta tttctaaggt tcactcttct ccaacctctc    27720
actctgttgt tctctcatct gccagaaagc acaccactct tggacaaaga aaaactgatg    27780
acccttcagt gctggagttt tccaggcagg aaggacaggg aggttcagag aatcccaacg    27840
tttgaaggga gtgtgaagat caggtggtcc gatcccatga tgcatgaaaa cctctataat    27900
attaggataa gggcttcagt tctctgccgg gtttccagaa cagattcaat tacccaaaat    27960
ggaggcaagg ctcccaaagt attttaacaa cagataacca gaaccagaga ccccactcat    28020
tgcactagaa aatcccctcc tgtcttcatt aagctctttg aggctgtcca cccaaagcat    28080
tgggtctgat tggggactgt cttttagcca tgcttactgg atccccagga gaggaaaact    28140
atttggatat aaaaaattat ttcagctgat ttggacaaga ttatcgcttt cttttcccac    28200
caactccccc catctccccc acccctgcca actcttcacc tcatctcacg agactggaga    28260
gctcctggag tgatcttgtc ccaccttccc cagggcttcc ccacctcatc tacctgctga    28320
atgggtaggt aaaaaatctc taaacttaca gattcacagc accaacatga ggttgcatgg    28380
gggcaggcca tgatgagaga agaagaaggg tttggggacc catattctgg cagttttttct    28440 accatcaccc caaactacaa gcaacagctc ttggctgtac aaatgagagt gtctatgttg    28500
aacataaata tgcaatcatt aaagatgtgt cagtttggag agaaagggac tttagaggag    28560
gctgtgtctc aaactctttt cctatctcac ccatcttcca ctctccctct cccagtctct    28620
gccctcccca acactttctc ccatctttat ctcctctcat acaacactga tgaattctat    28680
cagccatgac agtcttgtcc tgctgcactt taaaatggca gatcttaaat catctttcca    28740
gtttcttcca taattgacat agtcaagttt tctgcttcat cttgagtcga gcttgagcat    28800
ttgctaagat ataatcaatt ttcctttagct ttaaatgttt gtggccatag agttacttat    28860
aatgttctca tagaacaatt tcagtctctc ctgtatgcat ggttttatcc ccttctcatt    28920
tctactctta cataattttg ttatctcttt tctttaatca ggtttgcaag gagttcatta    28980
attttactga cttttttcaaa gaagcgattt tggatttatt tgtcctttct acttgttttg    29040
gtttgttttc tattgattta ttttttcctgt tttcttaagg tttaaatgtt attttctaat    29100
gttttaaaat tgatgtagaa ttccttcatt ttaggtcttt ctaacaacaa agccatttac    29160
agctattaat tttctcctga gtacagcttt agctggatac tataggtttt agaataaagg    29220
agtctacatt tatcattttt aaaatagttt gtaatttaa ttttattcc tctttggttg    29280 tttgaggatt atttaataat gggtttctta atttctagca tttaggaatc ttttgatttt    29340
tttaactttg tatatctagt tttattggat tatgagcaga aaacatggcc tgtaaaaatc    29400
```

-continued

```
tttattttaa aattgtgtga attttcttc attgtcaagt acctgattga ttttggacat    29460
ataaaattaa attttacttt gaaagaaata catattaaat tgatttgtta attgtattat    29520
tcaatttctc tatgttctta tttttttgta tatgggtct taattctgaa aagggtttgt     29580
taaaaatcaa ctataattgt actgtttcat taatctttgc atttctaaaa catttacctc    29640
atataattag ttaccacatt gtttgatgcc tattaattta tgacaatctt tttcttcaaa    29700 aatttttgcct attattataa gttaccctct ttattctagt taatgctttt ttttttttt   29760 tttttttt tttgagatgg agtctcactc tatcgcccag gctggagtgc agtggcacca     29820
tgctgggctc actgcaagct ccgcctaccc gggttcacgc cattccttcc tgcctcagcc    29880
tccagattag ctgggactac aggcacccgc caccacgacc agctaatttt ttgtattttt    29940
ttgggtctca ctttgttgcc aaggctggtc tgggctcaag tgatcctccc accttggcct   30000
cccaaagtgc tggtattaca ggcatgagcc actgcatcca gccctaaatt ctttgaccaa    30060
ctactgtgac attgcaaatc caggaatatc aatgccttca ctggagggag gatctccatc    30120
ctcaacgcct gtcacatcct tctcccccag agtccccagc caacacagg aaactaggaa     30180 acttcttcag tccccaatgc ttttgtttcc aggtgggcgt gccaccaggc acctgggcct   30240
tctgccttgc caccatcatc ttcctgctcc tgacgacaaa caacccagcc atcttcagac    30300
tcccactcag caaagtcacc taccccgagg ccaaccgcat ctactacctg acagtgaaaa    30360
gcggtgaaga agagaaggcc cccagcggtg aatagccatg ttcggggaag aaacgctctt    30420
tgcctgacct gatgtcctct ccctgtgttc tctgctctgg ttcaatcagt tgcagcactc    30480
accttctttg cctctccttg cacctgtgta gaaccaagca cacctgtaac tttcttcccc    30540
tgaagctgat tttcattctc tgccagaatc tccataacta tctattgtgc gacattaagg   30600
gatgttggta ttacagtaaa atttccggag ttagcaataa ggtgtgtgtc ttaaatgttg    30660
ttgacttaaa acaaaaacag tagtctttg gaaaggtaat taacaggtga tcttcttggc     30720
atcttaaact aaataataga tgctataaaa ttaaacttgt tgagtggttc ctaggcagac    30780
acagagtagg ggggtaagtc aggggacaca ggctaggaag ggaaggctct ctagtggctg    30840
agctagagac taatgaccac aaagagagga atttcacact gatgggattt taaagtcaaa    30900
acagggacga ttggggcagg gaattatcta ataaggagt cttaaccatt cagtggtctt     30960 tgtaagggc aaggcgatat tccatagcag ggaggaatta ataaattaga atcctatata     31020
tgactttatt atgaggata agcatttctt aatttagggc aaaccagcat ctctttaaaa     31080 ttaattttt aaattttaag ttctgggata catgtgcaaa catgccggt                  31129
```

<210> SEQ ID NO 4
<211> LENGTH: 452
<212> TYPE: PRT
<213> ORGANISM: Rattus norvegicus

<400> SEQUENCE: 4

```
Met Ser Asp Asn Asn Arg Ser Pro Leu Leu Pro Glu Pro Leu Ser Ser
 1               5                  10                  15

Arg Tyr Lys Leu Tyr Glu Ser Glu Leu Ser Ser Pro Thr Trp Pro Ser
            20                  25                  30

Ser Ser Gln Asp Thr His Pro Ala Leu Pro Leu Leu Glu Met Pro Glu
        35                  40                  45

Glu Lys Asp Leu Arg Ser Ser Asp Glu Asp Ser His Ile Val Lys Ile
    50                  55                  60
```

-continued

| | | | | | | | | | | | | | | |
|---|---|---|---|---|---|---|---|---|---|---|---|---|---|---|
| Glu | Lys | Pro | Asn | Glu | Arg | Ser | Lys | Arg | Arg | Glu | Ser | Glu | Leu | Pro | Arg |
| 65 | | | | 70 | | | | | 75 | | | | | 80 |

Arg Ala Ser Ala Gly Arg Gly Gly Phe Ser Leu Phe Gln Ala Val Ser
            85                  90                  95

Tyr Leu Thr Gly Asp Met Lys Glu Cys Lys Asn Trp Leu Lys Asp Lys
            100                 105                 110

Pro Leu Val Leu Gln Phe Leu Asp Trp Val Leu Arg Gly Ala Ala Gln
            115                 120                 125

Val Met Phe Val Asn Asn Pro Leu Ser Gly Leu Ile Phe Ile Gly
130             135                 140

Leu Leu Ile Gln Asn Pro Trp Trp Thr Ile Ala Gly Ala Leu Gly Thr
145             150                 155                 160

Val Val Ser Thr Leu Ala Ala Leu Ala Leu Ser Gln Asp Arg Ser Ala
            165                 170                 175

Ile Ala Ser Gly Leu His Gly Tyr Asn Gly Met Leu Val Gly Leu Leu
            180                 185                 190

Val Ala Val Phe Ser Glu Lys Leu Asp Tyr Tyr Trp Trp Leu Leu Phe
            195                 200                 205

Pro Val Thr Phe Ala Ser Met Ala Cys Pro Val Ile Ser Ser Ala Leu
            210                 215                 220

Ser Thr Val Phe Ala Lys Trp Asp Leu Pro Val Phe Thr Leu Pro Phe
225             230                 235                 240

Asn Ile Ala Leu Thr Leu Tyr Leu Ala Ala Thr Gly His Tyr Asn Leu
            245                 250                 255

Phe Phe Pro Thr Thr Leu Val Lys Pro Ala Ser Ser Ala Pro Asn Ile
            260                 265                 270

Thr Trp Ser Glu Ile Glu Met Pro Leu Leu Gln Thr Ile Pro Val
            275                 280                 285

Gly Val Gly Gln Val Tyr Gly Cys Asp Asn Pro Trp Thr Gly Val
290             295                 300

Ile Leu Val Ala Leu Phe Ile Ser Ser Pro Leu Ile Cys Leu His Ala
305             310                 315                 320

Ala Ile Gly Ser Ile Val Gly Leu Leu Ala Ala Leu Thr Val Ala Thr
            325                 330                 335

Pro Phe Glu Thr Ile Tyr Thr Gly Leu Trp Ser Tyr Asn Cys Val Leu
            340                 345                 350

Ser Cys Val Ala Ile Gly Gly Met Phe Tyr Val Leu Thr Trp Gln Thr
            355                 360                 365

His Leu Leu Ala Leu Val Cys Ala Leu Phe Cys Ala Tyr Thr Gly Ala
370             375                 380

Ala Leu Ser Asn Met Met Ala Val Val Gly Val Pro Pro Gly Thr Trp
385             390                 395                 400

Ala Phe Cys Leu Ser Thr Leu Thr Phe Leu Leu Leu Thr Ser Asn Asn
            405                 410                 415

Pro Gly Ile His Lys Leu Pro Leu Ser Lys Val Thr Tyr Pro Glu Ala
            420                 425                 430

Asn Arg Ile Tyr Phe Leu Thr Ala Lys Arg Ser Asp Glu Gln Lys Pro
            435                 440                 445

Pro Asn Gly Asp
    450

<210> SEQ ID NO 5
<211> LENGTH: 101
<212> TYPE: DNA

-continued

<213> ORGANISM: Homo sapiens

<400> SEQUENCE: 5
gccattggtg ctgcatgtct cgcccctac cccaaagcca aaattccccg ytgtaacaga    60
gtaaacattc ccgtggcaaa ggaacgctgt attccctaga g    101

<210> SEQ ID NO 6
<211> LENGTH: 101
<212> TYPE: DNA
<213> ORGANISM: Homo sapiens

<400> SEQUENCE: 6
ggaggaggag aggtaatagc ctagcgaaat ggaactaatg caaaattaga wagggactt    60 tatccccttt tgaagggaat cctgcaatcc ttgagcggtg t    101

<210> SEQ ID NO 7
<211> LENGTH: 101
<212> TYPE: DNA
<213> ORGANISM: Homo sapiens

<400> SEQUENCE: 7
catggagcac ggagcaatgg ggaaagctct aggtcatact gagaggagac ygcatgcagg    60
tccaaaacca cctctcaaat aaataaataa aaagatataa c    101

<210> SEQ ID NO 8
<211> LENGTH: 96
<212> TYPE: DNA
<213> ORGANISM: Homo sapiens
<220> FEATURE:
<221> NAME/KEY: variation
<222> LOCATION: 46
<223> OTHER INFORMATION: G may be either present or absent

<400> SEQUENCE: 8
accacagaca aagtgcataa ttttaattgt cgatcagcaa gacaagggtg tgtgtgtgtg    60
tgtttgtgtg tgtgtgtgtg tgtgttatca ggaaag    96

<210> SEQ ID NO 9
<211> LENGTH: 101
<212> TYPE: DNA
<213> ORGANISM: Homo sapiens

<400> SEQUENCE: 9
gggtcatttg gagatatgga ataaggagga ttcttttgtt ttttgtttgt ktgacacaga    60
gtcttgctct gtcgtccagg ctggagtgca gtggcgcaat c    101

<210> SEQ ID NO 10
<211> LENGTH: 101
<212> TYPE: DNA
<213> ORGANISM: Homo sapiens

<400> SEQUENCE: 10
tgcctcggcc tcccaaagtg ctgggattac aggcgtgagc caccatgccc rgccaggagg    60
attctttaaa ccaacaaaag acaacatttt ttttattgca a    101

<210> SEQ ID NO 11
<211> LENGTH: 101
<212> TYPE: DNA
<213> ORGANISM: Homo sapiens

<400> SEQUENCE: 11
ggaagaaagc agacagggtg tggattttat ggctgggaaa acaagccttt stcatcttgt      60
cacttctatt ttcttaatga agtaaagcca ggtggttggt g                          101

<210> SEQ ID NO 12
<211> LENGTH: 101
<212> TYPE: DNA
<213> ORGANISM: Homo sapiens

<400> SEQUENCE: 12
acatcttact ccttctgctg tatcattcct ctatctacat atatccataa rtgtataggg      60
atatttttcc agagcacttg aaacaacttt taaaaatatt t                          101

<210> SEQ ID NO 13
<211> LENGTH: 101
<212> TYPE: DNA
<213> ORGANISM: Homo sapiens

<400> SEQUENCE: 13
caccaagtcc cttgcgacat agcaaagggg ttttacatgc tggtgacagc rtgaagaccc      60
tcaggaaatg gaggataccc agaaaagtga cagtagcatg a                          101

<210> SEQ ID NO 14
<211> LENGTH: 101
<212> TYPE: DNA
<213> ORGANISM: Homo sapiens

<400> SEQUENCE: 14
ccaaagtatt ttaacaacag ataaccagaa ccagagaccc cactcattgc mctagaaaat      60
cccctcctgt cttcattaag ctctttgagg ctgtccaccc a                          101

<210> SEQ ID NO 15
<211> LENGTH: 101
<212> TYPE: DNA
<213> ORGANISM: Homo sapiens

<400> SEQUENCE: 15
cttccccagg gcttccccac ctcatctacc tgctgaatgg gtaggtaaaa ratctctaaa      60
cttacagatt cacagcacca acatgaggtt gcatgggggc a                          101

<210> SEQ ID NO 16
<211> LENGTH: 101
<212> TYPE: DNA
<213> ORGANISM: Homo sapiens

<400> SEQUENCE: 16
cagtttcttc cataattgac atagtcaagt tttctgcttc atcttgagtc ragcttgagc      60
atttgctaag atataatcaa ttttctttag ctttaaatgt t                          101

<210> SEQ ID NO 17
<211> LENGTH: 101
<212> TYPE: DNA
<213> ORGANISM: Homo sapiens

<400> SEQUENCE: 17
tttgttatct cttttctttta atcaggtttg caaggagttc attaatttta ytgactttt      60 caaagaagcg attttggatt tatttgtcct ttctacttgt t                          101

<210> SEQ ID NO 18

-continued

```
<211> LENGTH: 101
<212> TYPE: DNA
<213> ORGANISM: Homo sapiens

<400> SEQUENCE: 18
attttggaca tataaaatta aattttactt tgaaagaaat acatattaaa ytgatttgtt          60
aattgtatta ttcaatttct ctatgttctt attttttgt a                             101
```

ISOLATED HUMAN TRANSPORTER PROTEINS, NUCLEIC ACID MOLECULES, ENCODING HUMAN TRANSPORTER PROTEINS, AND USES THEREOF

FIELD OF THE INVENTION

The present invention is in the field of transporter proteins that are related to the urea transporter subfamily, recombinant DNA molecules, and protein production. The present invention specifically provides novel peptides and proteins that effect ligand transport and nucleic acid molecules encoding such peptide and protein molecules, all of which are useful in the development of human therapeutics and diagnostic compositions and methods.

BACKGROUND OF THE INVENTION

Transporters

Transporter proteins regulate many different functions of a cell, including cell proliferation, differentiation, and signaling processes, by regulating the flow of molecules such as ions and macromolecules, into and out of cells. Transporters are found in the plasma membranes of virtually every cell in eukaryotic organisms. Transporters mediate a variety of cellular functions including regulation of membrane potentials and absorption and secretion of molecules and ion across cell membranes. When present in intracellular membranes of the Golgi apparatus and endocytic vesicles, transporters, such as chloride channels, also regulate organelle pH. For a review, see Greger, R. (1988) Annu. Rev. Physiol. 50:111–122.

Transporters are generally classified by structure and the type of mode of action. In addition, transporters are sometimes classified by the molecule type that is transported, for example, sugar transporters, chlorine channels, potassium channels, etc. There may be many classes of channels for transporting a single type of molecule (a detailed review of channel types can be found at Alexander, S. P. H. and J. A. Peters: Receptor and transporter nomenclature supplement. Trends Pharmacol. Sci., Elsevier, pp. 65–68 (1997).

The following general classification scheme is known in the art and is followed in the present discoveries.

Channel-type transporters. Transmembrane channel proteins of this class are ubiquitously found in the membranes of all types of organisms from bacteria to higher eukaryotes. Transport systems of this type catalyze facilitated diffusion (by an energy-independent process) by passage through a transmembrane aqueous pore or channel without evidence for a carrier-mediated mechanism. These channel proteins usually consist largely of a-helical spanners, although b-strands may also be present and may even comprise the channel. However, outer membrane porin-type channel proteins are excluded from this class and are instead included in class 9.

Carrier-type transporters. Transport systems are included in this class if they utilize a carrier-mediated process to catalyze uniport (a single species is transported by facilitated diffusion), antiport (two or more species are transported in opposite directions in a tightly coupled process, not coupled to a direct form of energy other than chemiosmotic energy) and/or symport (two or more species are transported together in the same direction in a tightly coupled process, not coupled to a direct form of energy other than chemiosmotic energy).

Pyrophosphate bond hydrolysis-driven active transporters. Transport systems are included in this class if they hydrolyze pyrophosphate or the terminal pyrophosphate bond in ATP or another nucleoside triphosphate to drive the active uptake and/or extrusion of a solute or solutes. The transport protein may or may not be transiently phosphorylated, but the substrate is not phosphorylated.

PEP-dependent, phosphoryl transfer-driven group translocators. Transport systems of the bacterial phosphoenolpyruvate:sugar phosphotransferase system are included in this class. The product of the reaction, derived from extracellular sugar, is a cytoplasmic sugar-phosphate.

Decarboxylation-driven active transporters. Transport systems that drive solute (e.g., ion) uptake or extrusion by decarboxylation of a cytoplasmic substrate are included in this class.

Oxidoreduction-driven active transporters. Transport systems that drive transport of a solute (e.g., an ion) energized by the flow of electrons from a reduced substrate to an oxidized substrate are included in this class.

Light-driven active transporters. Transport systems that utilize light energy to drive transport of a solute (e.g., an ion) are included in this class.

Mechanically-driven active transporters. Transport systems are included in this class if they drive movement of a cell or organelle by allowing the flow of ions (or other solutes) through the membrane down their electrochemical gradients.

Outer-membrane porins (of b-structure). These proteins form transmembrane pores or channels that usually allow the energy independent passage of solutes across a membrane. The transmembrane portions of these proteins consist exclusively of b-strands that form a b-barrel. These porin-type proteins are found in the outer membranes of Gram-negative bacteria, mitochondria and eukaryotic plastids.

Methyltransferase-driven active transporters. A single characterized protein currently falls into this category, the Na+-transporting methyltetrahydromethanopterin:coenzyme M methyltransferase.

Non-ribosome-synthesized channel-forming peptides or peptide-like molecules. These molecules, usually chains of L- and D-amino acids as well as other small molecular building blocks such as lactate, form oligomeric transmembrane ion channels. Voltage may induce channel formation by promoting assembly of the transmembrane channel. These peptides are often made by bacteria and fungi as agents of biological warfare.

Non-Proteinaceous Transport Complexes. Ion conducting substances in biological membranes that do not consist of or are not derived from proteins or peptides fall into this category.

Functionally characterized transporters for which sequence data are lacking. Transporters of particular physiological significance will be included in this category even though a family assignment cannot be made.

Putative transporters in which no family member is an established transporter. Putative transport protein families are grouped under this number and will either be classified elsewhere when the transport function of a member becomes established, or will be eliminated from the TC classification system if the proposed transport function is disproven. These families include a member or members for which a transport function has been suggested, but evidence for such a function is not yet compelling.

Auxiliary transport proteins. Proteins that in some way facilitate transport across one or more biological membranes but do not themselves participate directly in transport are included in this class. These proteins always function in conjunction with one or more transport proteins. They may provide a function connected with energy coupling to transport, play a structural role in complex formation or serve a regulatory function.

Transporters of unknown classification. Transport protein families of unknown classification are grouped under this number and will be classified elsewhere when the transport process and energy coupling mechanism are characterized. These families include at least one member for which a transport function has been established, but either the mode of transport or the energy coupling mechanism is not known.

Urea Transporters

The protein provided by the present invention is highly homologous to the family of urea transporters (UTs). UTs are transmembrane proteins that carry urea across cellular membranes. UTs may be expressed in such tissues as the outer and inner medulla of the kidney, erythropoietic tissue, testis and hepatocytes.

The primary function of UTs is production of concentrated urea, which is critical for retention of water. UT-A1 is a facilitated urea transporter; however, active urea transporters are found in the inner medullary collecting duct (IMCD). UTs in hepatocytes contribute to uremia-induced uptake and conversion of urea.

UT-mediated urea uptake is inhibited by phloretin and increased by forskolin. Vasopressin and possibly other neurohypophysal hormones, such as isotocin and mesotocin, regulate UTs. Inhibition of urea uptake induces UT-A1 expression. Hyperosmolarity and dehydration increases expression of another urea transporter, UT-A2, suggesting that this protein may play a role in hypertension. In addition to UT-A1 and UT-A2, two additional functional UT isoforms are UT-A3 and UT-A4.

Urea transporters can be used to estimate the effect of various drugs on urea uptake in kidneys and liver. For example, changes in mRNA concentrations before and after administration of a drug may indicate drug efficiency. Specific drugs can be developed to modify activity of urea transporters to alleviate uremia and similar conditions.

For a review of urea transporters, see Karakashian et al., *J Am Soc Nephrol* 1999 February 10(2): 230–7; Sands, *Mt Sinai J Med* 2000 March; 67(2): 112–9; and Leroy et al., *Biochem Biophys Res Commun* 2000 May 10; 271(2): 368–73.

Ion channels

An important type of transporter is the ion channel. Ion channels regulate many different cell proliferation, differentiation, and signaling processes by regulating the flow of ions into and out of cells. Ion channels are found in the plasma membranes of virtually every cell in eukaryotic organisms. Ion channels mediate a variety of cellular functions including regulation of membrane potentials and absorption and secretion of ion across epithelial membranes. When present in intracellular membranes of the Golgi apparatus and endocytic vesicles, ion channels, such as chloride channels, also regulate organelle pH. For a review, see Greger, R. (1988) Annu. Rev. Physiol. 50:111–122.

Ion channels are generally classified by structure and the type of mode of action. For example, extracellular ligand gated channels (ELGs) are comprised of five polypeptide subunits, with each subunit having 4 membrane spanning domains, and are activated by the binding of an extracellular ligand to the channel. In addition, channels are sometimes classified by the ion type that is transported, for example, chlorine channels, potassium channels, etc. There may be many classes of channels for transporting a single type of ion (a detailed review of channel types can be found at Alexander, S. P. H. and J. A. Peters (1997). Receptor and ion channel nomenclature supplement. Trends Pharmacol. Sci., Elsevier, pp. 65–68 and http://www-biology.ucsd.edu/~msaier/transport/toc.html.

There are many types of ion channels based on structure. For example, many ion channels fall within one of the following groups: extracellular ligand-gated channels (ELG), intracellular ligand-gated channels (ILG), inward rectifying channels (INR), intercellular (gap junction) channels, and voltage gated channels (VIC). There are additionally recognized other channel families based on ion-type transported, cellular location and drug sensitivity. Detailed information on each of these, their activity, ligand type, ion type, disease association, drugability, and other information pertinent to the present invention, is well known in the art.

Extracellular ligand-gated channels, ELGs, are generally comprised of five polypeptide subunits, Unwin, N. (1993), Cell 72: 31–41; Unwin, N. (1995), Nature 373: 37–43; Hucho, F., et al., (1996) J. Neurochem. 66: 1781–1792; Hucho, F., et al., (1996) Eur. J. Biochem. 239: 539–557; Alexander, S. P. H. and J. A. Peters (1997), Trends Pharmacol. Sci., Elsevier, pp. 4–6; 36–40; 42–44; and Xue, H. (1998) J. Mol. Evol. 47: 323–333. Each subunit has 4 membrane spanning regions: this serves as a means of identifying other members of the ELG family of proteins. ELG bind a ligand and in response modulate the flow of ions. Examples of ELG include most members of the neurotransmitter-receptor family of proteins, e.g., GABAI receptors. Other members of this family of ion channels include glycine receptors, ryandyne receptors, and ligand gated calcium channels.

The Voltage-gated Ion Channel (VIC) Superfamily

Proteins of the VIC family are ion-selective channel proteins found in a wide range of bacteria, archaea and eukaryotes Hille, B. (1992), Chapter 9: Structure of channel proteins; Chapter 20: Evolution and diversity. In: Ionic Channels of Excitable Membranes, 2nd Ed., Sinaur Assoc. Inc., Pubs., Sunderland, Mass.; Sigworth, F. J. (1993), Quart. Rev. Biophys. 27: 1–40; Salkoff, L. and T. Jegla (1995), Neuron 15: 489–492; Alexander, S. P. H. et al., (1997), Trends Pharmacol. Sci., Elsevier, pp. 76–84; Jan, L. Y. et al., (1997), Annu. Rev. Neurosci. 20: 91–123; Doyle, D. A, et al., (1998) Science 280: 69–77; Terlau, H. and W. Stühmer (1998), Naturwissenschaften 85: 437–444. They are often homo- or heterooligomeric structures with several dissimilar subunits (e.g., a1-a2-d-b $Ca^{2+}$ channels, $ab_1b_2$ $Na^+$ channels or $(a)_4$-b $K^+$ channels), but the channel and the primary receptor is usually associated with the a (or a1) subunit. Functionally characterized members are specific for $K^+$, $Na^+$ or $Ca^{2+}$. The $K^+$ channels usually consist of homotetrameric structures with each a-subunit possessing six transmembrane spanners (TMSs). The a1 and a subunits of the $Ca^{2+}$ and $Na^+$ channels, respectively, are about four times as large and possess 4 units, each with 6 TMSs separated by a hydrophilic loop, for a total of 24 TMSs. These large channel proteins form heterotetra-unit structures equivalent to the homotetramenic structures of most $K^+$ channels. All four units of the $Ca^{2+}$ and $Na^+$ channels are homologous to the single unit in the homotetrameric $K^+$ channels. Ion flux via the eukaryotic channels is generally controlled by the transmembrane electrical potential (hence the designation, voltage-sensitive) although some are controlled by ligand or receptor binding.

Several putative $K^+$-selective channel proteins of the VIC family have been identified in prokaryotes. The structure of one of them, the KcsA $K^+$ channel of *Streptomyces lividans*, has been solved to 3.2 Å resolution. The protein possesses four identical subunits, each with two transmembrane helices, arranged in the shape of an inverted teepee or cone. The cone cradles the "selectivity filter" P domain in its outer end. The narrow selectivity filter is only 12 Å long, whereas the remainder of the channel is wider and lined with hydrophobic residues. A large water-filled cavity and helix dipoles stabilize $K^+$ in the pore. The selectivity filter has two bound $K^+$ ions about 7.5 Å apart from each other. Ion conduction is proposed to result from a balance of electrostatic attractive and repulsive forces.

In eukaryotes, each VIC family channel type has several subtypes based on pharmacological and electrophysiological data. Thus, there are five types of $Ca^{2+}$ channels (L, N, P, Q and T). There are at least ten types of $K^+$ channels, each responding in different ways to different stimuli: voltage-sensitive [Ka, Kv, Kvr, Kvs and Ksr], $Ca^{2+}$-sensitive [$BK_{Ca}$, $IK_{Ca}$ and $SK_{Ca}$] and receptor-coupled [$K_M$ and $K_{ACh}$]. There are at least six types of $Na^+$ channels (I, II, III, $\mu$1, H1 and PN3). Tetrameric channels from both prokaryotic and eukaryotic organisms are known in which each a-subunit possesses 2 TMSs rather than 6, and these two TMSs are homologous to TMSs 5 and 6 of the six TMS unit found in the voltage-sensitive channel proteins. KcsA of *S. lividans* is an example of such a 2 TMS channel protein. These channels may include the $K_{Na}$ ($Na^+$-activated) and $K_{Vol}$ (cell volume-sensitive) $K^+$ channels, as well as distantly related channels such as the Tok1 $K^+$ channel of yeast, the TWIK-1 inward rectifier $K^+$ channel of the mouse and the TREK-1 $K^+$ channel of the mouse. Because of insufficient sequence similarity with proteins of the VIC family, inward rectifier $K^+$ IRK channels (ATP-regulated; G-protein-activated) which possess a P domain and two flanking TMSs are placed in a distinct family. However, substantial sequence similarity in the P region suggests that they are homologous. The b, g and d subunits of VIC family members, when present, frequently play regulatory roles in channel activation/deactivation.

The Epithelial $Na^+$ Channel (ENaC) Family

The ENaC family consists of over twenty-four sequenced proteins (Canessa, C. M., et al., (1994), Nature 367: 463–467, Le, T. and M. H. Saier, Jr. (1996), Mol. Membr. Biol. 13: 149–157; Garty, H. and L. G. Palmer (1997), Physiol. Rev. 77: 359–396; Waldmann, R., et al., (1997), Nature 386: 173–177; Darboux, I., et al., (1998), J. Biol. Chem. 273: 9424–9429; Firsov, D., et al., (1998), EMBO J. 17: 344–352; Horisberger, J.-D. (1998). Curr. Opin. Struc. Biol. 10: 443–449). All are from animals with no recognizable homologues in other eukaryotes or bacteria. The vertebrate ENaC proteins from epithelial cells cluster tightly together on the phylogenetic tree: voltage-insensitive ENaC homologues are also found in the brain. Eleven sequenced *C. elegans* proteins, including the degenerins, are distantly related to the vertebrate proteins as well as to each other. At least some of these proteins form part of a mechanotransducing complex for touch sensitivity. The homologous *Helix aspersa* (FMRF-amide)-activated $Na^+$ channel is the first peptide neurotransmitter-gated ionotropic receptor to be sequenced.

Protein members of this family all exhibit the same apparent topology, each with N- and C-termini on the inside of the cell, two amphipathic transmembrane spanning segments, and a large extracellular loop. The extracellular domains contain numerous highly conserved cysteine residues. They are proposed to serve a receptor function.

Mammalian ENaC is important for the maintenance of $Na^+$ balance and the regulation of blood pressure. Three homologous ENaC subunits, alpha, beta, and gamma, have been shown to assemble to form the highly $Na^+$-selective channel. The stoichiometry of the three subunits is $alpha_2$, beta1, gamma1 in a heterotetrameric architecture.

The Glutamate-gated Ion Channel (GIC) Family of Neurotransmitter Receptors

Members of the GIC family are heteropentameric complexes in which each of the 5 subunits is of 800–1000 amino acyl residues in length (Nakanishi, N., et al, (1990), Neuron 5: 569–581; Unwin, N. (1993), Cell 72: 31–41; Alexander, S. P. H. and J. A. Peters (1997) Trends Pharmacol. Sci., Elsevier, pp. 36–40). These subunits may span the membrane three or five times as putative a-helices with the N-termini (the glutamate-binding domains) localized extracellularly and the C-termini localized cytoplasmically. They may be distantly related to the ligand-gated ion channels, and if so, they may possess substantial b-structure in their transmembrane regions. However, homology between these two families cannot be established on the basis of sequence comparisons alone. The subunits fall into six subfamilies: a, b, g, d, e and z.

The GIC channels are divided into three types: (1) a-amino-3-hydroxy-5-methyl-4-isoxazole propionate (AMPA)-, (2) kainate- and (3) N-methyl-D-aspartate (NMDA)-selective glutamate receptors. Subunits of the AMPA and kainate classes exhibit 35–40% identity with each other while subunits of the NMDA receptors exhibit 22–24% identity with the former subunits. They possess large N-terminal, extracellular glutamate-binding domains that are homologous to the periplasmic glutamine and glutamate receptors of ABC-type uptake permeases of Gram-negative bacteria. All known members of the GIC family are from animals. The different channel (receptor) types exhibit distinct ion selectivities and conductance properties. The NMDA-selective large conductance channels are highly permeable to monovalent cations and $Ca^{2+}$. The AMPA- and kainate-selective ion channels are permeable primarily to monovalent cations with only low permeability to $Ca^{2+}$.

The Chloride Channel (ClC) Family

The ClC family is a large family consisting of dozens of sequenced proteins derived from Gram-negative and Gram-positive bacteria, cyanobacteria, archaea, yeast, plants and animals (Steinmeyer, K., et al., (1991), Nature 354: 301–304; Uchida, S., et al., (1993), J. Biol. Chem. 268: 3821–3824; Huang, M.-E., et al., (1994), J. Mol. Biol. 242: 595–598; Kawasaki, M., et al, (1994), Neuron 12: 597–604; Fisher, W. E., et al., (1995), Genomics. 29:598–606; and Foskett, J. K. (1998), Annu. Rev. Physiol. 60: 689–717). These proteins are essentially ubiquitous, although they are not encoded within genomes of *Haemophilus influenzae*, *Mycoplasma genitalium*, and *Mycoplasma pneumoniae*. Sequenced proteins vary in size from 395 amino acyl residues (*M. jannaschii*) to 988 residues (man). Several organisms contain multiple ClC family paralogues. For example, *Synechocystis* has two paralogues, one of 451 residues in length and the other of 899 residues. *Arabidopsis thaliana* has at least four sequenced paralogues, (775–792 residues), humans also have at least five paralogues (820–988 residues), and *C. elegans* also has at least five (810–950 residues). There are nine known members in mammals, and mutations in three of the corresponding genes cause human diseases. *E. coli*, *Methanococcus jannaschii* and *Saccharomyces cerevisiae* only have one ClC family member each. With the exception of the larger Synechocystis paralogue, all bacterial proteins are small (395–492 residues) while all eukaryotic proteins are larger (687–988 residues). These proteins exhibit 10–12 putative transmembrane a-helical spanners (TMSs) and appear to be present in the membrane as homodimers. While one member of the family, Torpedo ClC-O, has been reported to have two channels, one per subunit, others are believed to have just one.

All functionally characterized members of the ClC family transport chloride, some in a voltage-regulated process. These channels serve a variety of physiological functions (cell volume regulation; membrane potential stabilization; signal transduction; transepithelial transport, etc.). Different homologues in humans exhibit differing anion selectivities, i.e., ClC4 and ClC5 share a $NO_3^->Cl^->Br^->I^-$ conductance sequence, while ClC3 has an $I^->Cl^-$ selectivity. The ClC4 and ClC5 channels and others exhibit outward rectifying currents with currents only at voltages more positive than +20 mV.

Animal Inward Rectifier K$^+$ Channel (IRK-C) Family

IRK channels possess the "minimal channel-forming structure" with only a P domain, characteristic of the channel proteins of the VIC family, and two flanking transmembrane spanners (Shuck, M. E., et al., (1994), J. Biol. Chem. 269: 24261–24270; Ashen, M. D., et al., (1995), Am. J. Physiol. 268: H506–H511; Salkoff, L. and T. Jegla (1995), Neuron 15: 489–492; Aguilar-Bryan, L., et al., (1998), Physiol. Rev. 78: 227–245; Ruknudin, A., et al., (1998), J. Biol. Chem. 273: 14165–14171). They may exist in the membrane as homo- or heterooligomers. They have a greater tendency to let K$^+$ flow into the cell than out. Voltage-dependence may be regulated by external K$^+$, by internal Mg$^{2+}$, by internal ATP and/or by G-proteins. The P domains of IRK channels exhibit limited sequence similarity to those of the VIC family, but this sequence similarity is insufficient to establish homology. Inward rectifiers play a role in setting cellular membrane potentials, and the closing of these channels upon depolarization permits the occurrence of long duration action potentials with a plateau phase. Inward rectifiers lack the intrinsic voltage sensing helices found in VIC family channels. In a few cases, those of Kir1.1a and Kir6.2, for example, direct interaction with a member of the ABC superfamily has been proposed to confer unique functional and regulatory properties to the heteromeric complex, including sensitivity to ATP. The SURI sulfonylurea receptor (spQ09428) is the ABC protein that regulates the Kir6.2 channel in response to ATP, and CFTR may regulate Kir1.1a. Mutations in SURI are the cause of familial persistent hyperinsulinemic hypoglycemia in infancy (PHHI), an autosomal recessive disorder characterized by unregulated insulin secretion in the pancreas.

ATP-gated Cation Channel (ACC) Family

Members of the ACC family (also called P2X receptors) respond to ATP, a functional neurotransmitter released by exocytosis from many types of neurons (North, R. A. (1996), Curr. Opin. Cell Biol. 8: 474–483; Soto, F., M. Garcia-Guzman and W. Stühmer (1997), J. Membr. Biol. 160: 91–100). They have been placed into seven groups (P2X$_1$–P2X$_7$) based on their pharmacological properties. These channels, which function at neuron-neuron and neuron-smooth muscle junctions, may play roles in the control of blood pressure and pain sensation. They may also function in lymphocyte and platelet physiology. They are found only in animals.

The proteins of the ACC family are quite similar in sequence (>35% identity), but they possess 380–1000 amino acyl residues per subunit with variability in length localized primarily to the C-terminal domains. They possess two transmembrane spanners, one about 30–50 residues from their N-termini, the other near residues 320–340. The extracellular receptor domains between these two spanners (of about 270 residues) are well conserved with numerous conserved glycyl and cysteyl residues. The hydrophilic C-termini vary in length from 25 to 240 residues. They resemble the topologically similar epithelial Na$^+$ channel (ENaC) proteins in possessing (a) N- and C-termini localized intracellularly, (b) two putative transmembrane spanners, (c) a large extracellular loop domain, and (d) many conserved extracellular cysteyl residues. ACC family members are, however, not demonstrably homologous with them. ACC channels are probably hetero- or homomultimers and transport small monovalent cations (Me$^+$). Some also transport Ca$^{2+}$; a few also transport small metabolites.

The Ryanodine-Inositol 1,4,5-triphosphate Receptor Ca$^{2+}$ Channel (RIR-CaC) Family Ryanodine (Ry)-sensitive and inositol 1,4,5-triphosphate (IP3)-sensitive Ca$^{2+}$-release channels function in the release of Ca$^{2+}$ from intracellular storage sites in animal cells and thereby regulate various Ca$^{2+}$-dependent physiological processes (Hasan, G. et al., (1992) Development 116: 967–975; Michikawa, T., et al., (1994), J. Biol. Chem. 269: 9184–9189; Tunwell, R. E. A., (1996), Biochem. J. 318: 477–487; Lee, A. G. (1996) *Biomembranes*, Vol. 6, Transmembrane Receptors and Channels (A. G. Lee, ed.), JAI Press, Denver, Colo., pp 291–326; Mikoshiba, K., et al., (1996) J. Biochem. Biomem. 6: 273–289). Ry receptors occur primarily in muscle cell sarcoplasmic reticular (SR) membranes, and IP3 receptors occur primarily in brain cell endoplasmic reticular (ER) membranes where they effect release of Ca$^{2+}$ into the cytoplasm upon activation (opening) of the channel.

The Ry receptors are activated as a result of the activity of dihydropyridine-sensitive Ca$^{2+}$ channels. The latter are members of the voltage-sensitive ion channel (VIC) family. Dihydropyridine-sensitive channels are present in the T-tubular systems of muscle tissues.

Ry receptors are homotetrameric complexes with each subunit exhibiting a molecular size of over 500,000 daltons (about 5,000 amino acyl residues). They possess C-terminal domains with six putative transmembrane a-helical spanners (TMSs). Putative pore-forming sequences occur between the fifth and sixth TMSs as suggested for members of the VIC family. The large N-terminal hydrophilic domains and the small C-terminal hydrophilic domains are localized to the cytoplasm. Low resolution 3-dimensional structural data are available. Mammals possess at least three isoforms that probably arose by gene duplication and divergence before divergence of the mammalian species. Homologues are present in humans and *Caenorabditis elegans*.

IP$_3$ receptors resemble Ry receptors in many respects. (1) They are homotetrameric complexes with each subunit exhibiting a molecular size of over 300,000 daltons (about 2,700 amino acyl residues). (2) They possess C-terminal channel domains that are homologous to those of the Ry receptors. (3) The channel domains possess six putative TMSs and a putative channel lining region between TMSs 5 and 6. (4) Both the large N-terminal domains and the smaller C-terminal tails face the cytoplasm. (5) They possess covalently linked carbohydrate on extracytoplasmic loops of the channel domains. (6) They have three currently recognized isoforms (types 1, 2, and 3) in mammals which are subject to differential regulation and have different tissue distributions.

IP$_3$ receptors possess three domains: N-terminal IP$_3$-binding domains, central coupling or regulatory domains and C-terminal channel domains. Channels are activated by IP$_3$ binding, and like the Ry receptors, the activities of the IP$_3$ receptor channels are regulated by phosphorylation of the regulatory domains, catalyzed by various protein kinases. They predominate in the endoplasmic reticular membranes of various cell types in the brain but have also been found in the plasma membranes of some nerve cells derived from a variety of tissues.

The channel domains of the Ry and $IP_3$ receptors comprise a coherent family that in spite of apparent structural similarities, do not show appreciable sequence similarity of the proteins of the VIC family. The Ry receptors and the $IP_3$ receptors cluster separately on the RIR-CaC family tree. They both have homologues in *Drosophila*. Based on the phylogenetic tree for the family, the family probably evolved in the following sequence: (1) A gene duplication event occurred that gave rise to Ry and $IP_3$ receptors in invertebrates. (2) Vertebrates evolved from invertebrates. (3) The three isoforms of each receptor arose as a result of two distinct gene duplication events. (4) These isoforms were transmitted to mammals before divergence of the mammalian species.

The Organellar Chloride Channel (O-ClC) Family

Proteins of the O-ClC family are voltage-sensitive chloride channels found in intracellular membranes but not the plasma membranes of animal cells (Landry, D, et al., (1993), J. Biol. Chem. 268: 14948–14955; Valenzuela, Set al., (1997), J. Biol. Chem. 272: 12575–12582; and Duncan, R. R., et al., (1997), J. Biol. Chem. 272: 23880–23886).

They are found in human nuclear membranes, and the bovine protein targets to the microsomes, but not the plasma membrane, when expressed in *Xenopus laevis* oocytes. These proteins are thought to function in the regulation of the membrane potential and in transepithelial ion absorption and secretion in the kidney. They possess two putative transmembrane a-helical spanners (TMSs) with cytoplasmic N- and C-termini and a large luminal loop that may be glycosylated. The bovine protein is 437 amino acyl residues in length and has the two putative TMSs at positions 223–239 and 367–385. The human nuclear protein is much smaller (241 residues). A *C. elegans* homologue is 260 residues long.

Transporter proteins, particularly members of the urea subfamily, are a major target for drug action and development. Accordingly, it is valuable to the field of pharmaceutical development to identify and characterize previously unknown transport proteins. The present invention advances the state of the art by providing previously unidentified human transport proteins.

SUMMARY OF THE INVENTION

The present invention is based in part on the identification of amino acid sequences of human transporter peptides and proteins that are related to the urea transporter subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate transporter activity in cells and tissues that express the transporter. Experimental data as provided in FIG. 1 indicates expression in the kidney, thyroid, testis, placenta, small intestine, pancreas, fetal brain, and heart.

DESCRIPTION OF THE FIGURE SHEETS

FIG. 1 (FIG. 1A–FIG. 1B) provides the nucleotide sequence of a cDNA molecule or transcript sequence that encodes the transporter protein of the present invention. In addition structure and functional information is provided, such as ATG start, stop and tissue distribution, where available, that allows one to readily determine specific uses of inventions based on this molecular sequence. Experimental data as provided in FIG. 1 indicates expression in the kidney, thyroid, testis, placenta, small intestine, pancreas, fetal brain, and heart.

FIG. 2 (FIG. 2A–FIG. 2B) provides the predicted amino acid sequence of the transporter of the present invention. In addition structure and functional information such as protein family, function, and modification sites is provided where available, allowing one to readily determine specific uses of inventions based on this molecular sequence.

FIG. 3 (FIG. 3A–FIG. 3M) provides genomic sequences that span the gene encoding the transporter protein of the present invention. In addition structure and functional information, such as intron/exon structure, promoter location, etc., is provided where available, allowing one to readily determine specific uses of inventions based on this molecular sequence. As illustrated in FIG. 3, identified SNP variations include C8221T, T11751A, C11944T, G17269T, G17548A, C19904G, A24723G, G27527A, A28024C, A28335G, G28789A, C28987T, T29500C, and a G indel at 16706.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a transporter protein or part of a transporter protein and are related to the urea transporter subfamily. Utilizing these sequences, additional genomic sequences were assembled and transcript and/or cDNA sequences were isolated and characterized. Based on this analysis, the present invention provides amino acid sequences of human transporter peptides and proteins that are related to the urea transporter subfamily, nucleic acid sequences in the form of transcript sequences, cDNA sequences and/or genomic sequences that encode these transporter peptides and proteins, nucleic acid variation (allelic information), tissue distribution of expression, and information about the closest art known protein/peptide/domain that has structural or sequence homology to the transporter of the present invention.

In addition to being previously unknown, the peptides that are provided in the present invention are selected based on their ability to be used for the development of commercially important products and services. Specifically, the present peptides are selected based on homology and/or structural relatedness to known transporter proteins of the urea transporter subfamily and the expression pattern observed Experimental data as provided in FIG. 1 indicates expression in the kidney, thyroid, testis, placenta, small intestine, pancreas, fetal brain, and heart. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known urea family or subfamily of transporter proteins.

Specific Embodiments

Peptide Molecules

The present invention provides nucleic acid sequences that encode protein molecules that have been identified as being members of the transporter family of proteins and are related to the urea transporter subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the transporter peptides of the present invention, transporter peptides, or peptides/proteins of the present invention.

The present invention provides isolated peptide and protein molecules that consist of, consist essentially of, or comprising the amino acid sequences of the transporter peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the transporter peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated transporter peptide can be purified from cells that naturally express it, purified from cells that have been altered to express it (recombinant), or synthesized using known protein synthesis methods. Experimental data as provided in FIG. 1 indicates expression in the kidney, thyroid, testis, placenta, small intestine, pancreas, fetal brain, and heart. For example, a nucleic acid molecule encoding the transporter peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the transporter peptides of the present invention are the naturally occurring mature proteins. A brief description of how various types of these proteins can be made/isolated is provided below.

The transporter peptides of the present invention can be attached to heterologous sequences to form chimeric or fusion proteins. Such chimeric and fusion proteins comprise a transporter peptide operatively linked to a heterologous protein having an amino acid sequence not substantially homologous to the transporter peptide. "Operatively linked" indicates that the transporter peptide and the heterologous protein are fused in-frame. The heterologous protein can be fused to the N-terminus or C-terminus of the transporter peptide.

In some uses, the fusion protein does not affect the activity of the transporter peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant transporter peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A transporter peptide-encoding nucleic acid can be cloned into such an expression vector such that the fusion moiety is linked in-frame to the transporter peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the transporter peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the transporter peptides of the present invention as well as being encoded by the same genetic locus as the transporter peptide provided herein. As indicated by the data presented in FIG. 3, the map position was determined to be on chromosome 18 by a BLAST homology search against HTG (High Throughput Genomic Sequences division of GenBank).

Allelic variants of a transporter peptide can readily be identified as being a human protein having a high degree (significant) of sequence homology/identity to at least a portion of the transporter peptide as well as being encoded by the same genetic locus as the transporter peptide provided herein. Genetic locus can readily be determined based on the genomic information provided in FIG. 3, such as the genomic sequence mapped to the reference human. As indicated by the data presented in FIG. 3, the map position was determined to be on chromosome 18 by a BLAST homology search against HTG. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a transporter peptide encoding nucleic acid molecule under stringent conditions as more fully described below.

FIG. 3 provides information for SNPs identified in the gene encoding the urea transporter proteins of the present invention. The following variations were seen: C8221T, T11751A, C11944T, G17269T, G17548A, C19904G, A24723G, G27527A, A28024C, A28335G, G28789A, C28987T, T29500C, and a G indel at 16706. The variations in the amino acid sequence caused by these SNPs can readily be determined using the universal genetic code and the protein sequence provided in FIG. 2 as a reference.

Paralogs of a transporter peptide can readily be identified as having some degree of significant sequence homology/identity to at least a portion of the transporter peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a transporter peptide encoding nucleic acid molecule under moderate to stringent conditions as more fully described below.

Orthologs of a transporter peptide can readily be identified as having some degree of significant sequence homology/identity to at least a portion of the transporter peptide as well as being encoded by a gene from another organism. Preferred orthologs will be isolated from mammals, preferably primates, for the development of human therapeutic targets and agents. Such orthologs will be encoded by a nucleic acid sequence that will hybridize to a transporter peptide encoding nucleic acid molecule under moderate to stringent conditions, as more fully described below, depending on the degree of relatedness of the two organisms yielding the proteins.

Non-naturally occurring variants of the transporter peptides of the present invention can readily be generated using recombinant techniques. Such variants include, but are not limited to deletions, additions and substitutions in the amino acid sequence of the transporter peptide. For example, one class of substitutions are conserved amino acid substitution. Such substitutions are those that substitute a given amino acid in a transporter peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant transporter peptides can be fully functional or can lack function in one or more activities, e.g. ability to bind ligand, ability to transport ligand, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as transporter activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the transporter peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a transporter peptide. Such fragments can be chosen based on the ability to retain one or more of the biological activities of the transporter peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the transporter peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in transporter peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the transporter peptides of the present invention also encompass derivatives or analogs in which a substituted amino acid residue is not one encoded by the genetic code, in which a substituent group is included, in which the mature transporter peptide is fused with another compound, such as a compound to increase the half-life of the transporter peptide (for example, polyethylene glycol), or in which the additional amino acids are fused to the mature transporter peptide, such as a leader or secretory sequence or a sequence for purification of the mature transporter peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a transporter-effector protein interaction or transporter-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, transporters isolated from humans and their human/mammalian orthologs serve as targets for identifying agents for use in mammalian therapeutic applications, e.g. a human drug, particularly in modulating a biological or pathological response in a cell or tissue that expresses the transporter. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart. A large percentage of pharmaceutical agents are being developed that modulate the activity of transporter proteins, particularly members of the urea subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the kidney, thyroid, testis, placenta, small intestine, pancreas, fetal brain, and heart. Such uses can readily be determined using the information provided herein, that known in the art and routine experimentation.

The proteins of the present invention (including variants and fragments that may have been disclosed prior to the present invention) are useful for biological assays related to transporters that are related to members of the urea subfamily. Such assays involve any of the known transporter functions or activities or properties useful for diagnosis and treatment of transporter-related conditions that are specific for the subfamily of transporters that the one of the present invention belongs to, particularly in cells and tissues that express the transporter. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart.

The proteins of the present invention are also useful in drug screening assays, in cell-based or cell-free systems ((Hodgson, Bio/technology, 1992, September 10(9);973–80). Cell-based systems can be native, i.e., cells that normally express the transporter, as a biopsy or expanded in cell culture. Experimental data as provided in FIG. 1 indicates expression in the kidney, thyroid, testis, placenta, small intestine, pancreas, fetal brain, and heart. In an alternate embodiment, cell-based assays involve recombinant host cells expressing the transporter protein.

The polypeptides can be used to identify compounds that modulate transporter activity of the protein in its natural state or an altered form that causes a specific disease or pathology associated with the transporter. Both the transporters of the present invention and appropriate variants and fragments can be used in high-throughput screens to assay candidate compounds for the ability to bind to the transporter. These compounds can be further screened against a functional transporter to determine the effect of the compound on the transporter activity. Further, these compounds can be tested in animal or invertebrate systems to determine activity/effectiveness. Compounds can be identified that activate (agonist) or inactivate (antagonist) the transporter to a desired degree.

Further, the proteins of the present invention can be used to screen a compound for the ability to stimulate or inhibit interaction between the transporter protein and a molecule that normally interacts with the transporter protein, e.g. a substrate or a component of the signal pathway that the transporter protein normally interacts (for example, another transporter). Such assays typically include the steps of combining the transporter protein with a candidate compound under conditions that allow the transporter protein, or fragment, to interact with the target molecule, and to detect the formation of a complex between the protein and the target or to detect the biochemical consequence of the interaction with the transporter protein and the target, such as any of the associated effects of signal transduction such as changes in membrane potential, protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant transporters or appropriate fragments containing mutations that affect transporter function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) transporter activity. The assays typically involve an assay of events in the signal transduction pathway that indicate transporter activity. Thus, the transport of a ligand, change in cell membrane potential, activation of a protein, a change in the expression of genes that are up- or down-regulated in response to the transporter protein dependent signal cascade can be assayed.

Any of the biological or biochemical functions mediated by the transporter can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the transporter can be assayed. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart.

Binding and/or activating compounds can also be screened by using chimeric transporter proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a ligand-binding region can be used that interacts with a different ligand then that which is recognized by the native transporter. Accordingly, a different set of signal transduction components is available as an end-point assay for activation. This allows for assays to be performed in other than the specific host cell from which the transporter is derived.

The proteins of the present invention are also useful in competition binding assays in methods designed to discover compounds that interact with the transporter (e.g. binding partners and/or ligands). Thus, a compound is exposed to a transporter polypeptide under conditions that allow the compound to bind or to otherwise interact with the polypeptide. Soluble transporter polypeptide is also added to the mixture. If the test compound interacts with the soluble transporter polypeptide, it decreases the amount of complex formed or activity from the transporter target. This type of assay is particularly useful in cases in which compounds are sought that interact with specific regions of the transporter. Thus, the soluble polypeptide that competes with the target transporter region is designed to contain peptide sequences corresponding to the region of interest.

To perform cell free drug screening assays, it is sometimes desirable to immobilize either the transporter protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of transporter-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a transporter-binding protein and a candidate compound are incubated in the transporter protein-presenting wells and the amount of complex trapped in the well can be quantitated. Methods for detecting such complexes, in addition to those described above for the GST-immobilized complexes, include immunodetection of complexes using antibodies reactive with the transporter protein target molecule, or which are reactive with transporter protein and compete with the target molecule, as well as enzyme-linked assays which rely on detecting an enzymatic activity associated with the target molecule.

Agents that modulate one of the transporters of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of transporter protein activity identified according to these drug screening assays can be used to treat a subject with a disorder mediated by the transporter pathway, by treating cells or tissues that express the transporter. Experimental data as provided in FIG. 1 indicates expression in the kidney, thyroid, testis, placenta, small intestine, pancreas, fetal brain, and heart. These methods of treatment include the steps of administering a modulator of transporter activity in a pharmaceutical composition to a subject in need of such treatment, the modulator being identified as described herein.

In yet another aspect of the invention, the transporter proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the transporter and are involved in transporter activity. Such transporter-binding proteins are also likely to be involved in the propagation of signals by the transporter proteins or transporter targets as, for example, downstream elements of a transporter-mediated signaling pathway. Alternatively, such transporter-binding proteins are likely to be transporter inhibitors.

The two-hybrid system is based on the modular nature of most transcription factors, which consist of separable DNA-binding and activation domains. Briefly, the assay utilizes two different DNA constructs. In one construct, the gene that codes for a transporter protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a transporter-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the transporter protein.

This invention further pertains to novel agents identified by the above-described screening assays. Accordingly, it is within the scope of this invention to further use an agent identified as described herein in an appropriate animal model. For example, an agent identified as described herein (e.g., a transporter-modulating agent, an antisense transporter nucleic acid molecule, a transporter-specific antibody, or a transporter-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The transporter proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the kidney, thyroid, testis, placenta, small intestine, pancreas, fetal brain, and heart. The method involves contacting a biological sample with a compound capable of interacting with the transporter protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered transporter activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the transporter protein in which one or more of the transporter functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and transporter activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the kidney, thyroid, testis, placenta, small intestine, pancreas, fetal brain, and heart. Accordingly, methods for treatment include the use of the transporter protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the transporter proteins. Antibodies can be prepared from any region of the peptide as described herein. However, preferred regions will include those involved in function/activity and/or transporter/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the kidney, thyroid, testis, placenta, small intestine, pancreas, fetal brain, and heart. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the kidney, thyroid, testis, placenta, small intestine, pancreas, fetal brain, and heart. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the kidney, thyroid, testis, placenta, small intestine, pancreas, fetal brain, and heart. Thus, where a specific protein has been correlated with expression in a specific tissue, antibodies that are specific for this protein can be used to identify a tissue type.

The antibodies are also useful for inhibiting protein function, for example, blocking the binding of the transporter peptide to a binding partner such as a ligand or protein binding partner. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a transporter peptide or protein of the present invention (cDNA, transcript and genomic sequence). Such nucleic acid molecules will consist of, consist essentially of, or comprise a nucleotide sequence that encodes one of the transporter peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the transporter peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the transporter proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 18 by a BLAST homology search against HTG.

FIG. 3 provides information for SNPs identified in the gene encoding the urea transporter proteins of the present invention. The following variations were seen: C8221T, T11751A, C11944T, G17269T, G17548A, C19904G, A24723G, G27527A, A28024C, A28335G, G28789A, C28987T, T29500C, and a G indel at 16706. The variations in the amino acid sequence caused by these SNPs can readily be determined using the universal genetic code and the protein sequence provided in FIG. 2 as a reference.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6× sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, identified SNP variations include C8221T, T11751A, C11944T, G17269T, G17548A, C19904G, A24723G, G27527A, A28024C, A28335G, G28789A, C28987T, T29500C, and a G indel at 16706.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 18 by a BLAST homology search against HTG.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart.

Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in transporter protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a transporter protein, such as by measuring a level of a transporter-encoding nucleic acid in a sample of cells from a subject e.g., mRNA or genomic DNA, or determining if a transporter gene has been mutated. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart.

Nucleic acid expression assays are useful for drug screening to identify compounds that modulate transporter nucleic acid expression.

The invention thus provides a method for identifying a compound that can be used to treat a disorder associated with nucleic acid expression of the transporter gene, particularly biological and pathological processes that are mediated by the transporter in cells and tissues that express it. Experimental data as provided in FIG. 1 indicates expression in the kidney, thyroid, testis, placenta, small intestine, pancreas, fetal brain, and heart. The method typically includes assaying the ability of the compound to modulate the expression of the transporter nucleic acid and thus identifying a compound that can be used to treat a disorder characterized by undesired transporter nucleic acid expression. The assays can be performed in cell-based and cell-free systems. Cell-based assays include cells naturally expressing the transporter nucleic acid or recombinant cells genetically engineered to express specific nucleic acid sequences.

The assay for transporter nucleic acid expression can involve direct assay of nucleic acid levels, such as mRNA levels, or on collateral compounds involved in the signal pathway. Further, the expression of genes that are up- or down-regulated in response to the transporter protein signal pathway can also be assayed. In this embodiment the regulatory regions of these genes can be operably linked to a reporter gene such as luciferase.

Thus, modulators of transporter gene expression can be identified in a method wherein a cell is contacted with a candidate compound and the expression of mRNA determined. The level of expression of transporter mRNA in the presence of the candidate compound is compared to the level of expression of transporter mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate transporter nucleic acid expression in cells and tissues that express the transporter. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart. Modulation includes both up-regulation (i.e. activation or agonization) or down-regulation (suppression or antagonization) or nucleic acid expression.

Alternatively, a modulator for transporter nucleic acid expression can be a small molecule or drug identified using the screening assays described herein as long as the drug or small molecule inhibits the transporter nucleic acid expression in the cells and tissues that express the protein. Experimental data as provided in FIG. 1 indicates expression in the kidney, thyroid, testis, placenta, small intestine, pancreas, fetal brain, and heart.

The nucleic acid molecules are also useful for monitoring the effectiveness of modulating compounds on the expression or activity of the transporter gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in transporter nucleic acid expression, and particularly in qualitative changes that lead to pathology. The nucleic acid molecules can be used to detect mutations in transporter genes and gene expression products such as mRNA. The nucleic acid molecules can be used as hybridization probes to detect naturally occurring genetic mutations in the transporter gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the transporter gene associated with a dysfunction provides a diagnostic tool for an active disease or susceptibility to disease when the disease results from overexpression, underexpression, or altered expression of a transporter protein.

Individuals carrying mutations in the transporter gene can be detected at the nucleic acid level by a variety of techniques. FIG. 3 provides information for SNPs identified in the gene encoding the urea transporter proteins of the present invention. The following variations were seen: C8221T, T11751A, C11944T, G17269T, G17548A, C19904G, A24723G, G27527A, A28024C, A28335G, G28789A, C28987T, T29500C, and a G indel at 16706. The variations in the amino acid sequence caused by these SNPs can readily be determined using the universal genetic code and the protein sequence provided in FIG. 2 as a reference. As indicated by the data presented in FIG. 3, the map position was determined to be on chromosome 18 by a BLAST homology search against HTG. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241: 1077–1080 (1988); and Nakazawa et al., *PNAS* 91:360–364 (1994)), the latter of which can be particularly useful for detecting point mutations in the gene (see Abravaya et al., *Nucleic Acids Res*. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a transporter gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant transporter gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr*. 36:127–162 (1996); and Griffin et al., *Appl. Biochem. Biotechnol*. 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol*. 217:286–295 (1992)), electrophoretic mobility of mutant and wild type nucleic acid is compared (Orita et al., *PNAS* 86:2766 (1989); Cotton et al., *Mutat. Res*. 285:125–144 (1993); and Hayashi et al., *Genet. Anal. Tech. Appl*. 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the transporter gene in an individual in order to select an appropriate compound or dosage regimen for treatment. FIG. 3 provides information for SNPs identified in the gene encoding the urea transporter proteins of the present invention. The following variations were seen: C8221T, T11751A, C11944T, G17269T, G17548A, C19904G, A24723G, G27527A, A28024C, A28335G, G28789A, C28987T, T29500C, and a G indel at 16706. The variations in the amino acid sequence caused by these SNPs can readily be determined using the universal genetic code and the protein sequence provided in FIG. 2 as a reference.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control transporter gene expression in cells, tissues, and organisms. A DNA antisense nucleic acid molecule is designed to be complementary to a region of the gene involved in transcription, preventing transcription and hence production of transporter protein. An antisense RNA or DNA nucleic acid molecule would hybridize to the mRNA and thus block translation of mRNA into transporter protein.

Alternatively, a class of antisense molecules can be used to inactivate mRNA in order to decrease expression of transporter nucleic acid. Accordingly, these molecules can treat a disorder characterized by abnormal or undesired transporter nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the transporter protein, such as ligand binding.

The nucleic acid molecules also provide vectors for gene therapy in patients containing cells that are aberrant in transporter gene expression. Thus, recombinant cells, which include the patient's cells that have been engineered ex vivo and returned to the patient, are introduced into an individual where the cells produce the desired transporter protein to treat the individual.

The invention also encompasses kits for detecting the presence of a transporter nucleic acid in a biological sample. Experimental data as provided in FIG. 1 indicates that urea transporter proteins of the present invention are expressed in the kidney, thyroid, testis, placenta, small intestine, pancreas, fetal brain, and heart. Specifically, a virtual northern blot shows expression in the kidney and PCR-based tissue screening panels indicate expression in humans in the kidney, thyroid, testis, placenta, small intestine, pancreas, fetal brain, and heart. For example, the kit can comprise reagents such as a labeled or labelable nucleic acid or agent capable of detecting transporter nucleic acid in a biological sample; means for determining the amount of transporter nucleic acid in the sample; and means for comparing the amount of transporter nucleic acid in the sample with a standard. The compound or agent can be packaged in a suitable container. The kit can further comprise instructions for using the kit to detect transporter protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the transporter proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the transporter gene of the present invention. FIG. 3 provides information for SNPs identified in the gene encoding the urea transporter proteins of the present invention. The following variations were seen: C8221T, T11751A, C11944T, G17269T, G17548A, C19904G, A24723G, G27527A, A28024C, A28335G, G28789A, C28987T, T29500C, and a G indel at 16706. The variations in the amino acid sequence caused by these SNPs can readily be determined using the universal genetic code and the protein sequence provided in FIG. 2 as a reference.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified transporter gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterotransporter. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185,Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J*. 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufinan et al, *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., *Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as transporters, appropriate secretion signals are incorporated into the vector. The signal sequence can be endogenous to the peptides or heterologous to these peptides.

Where the peptide is not secreted into the medium, which is typically the case with transporters, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a transporter protein or peptide that can be further purified to produce desired amounts of transporter protein or fragments. Thus, host cells containing expression vectors are useful for peptide production.

Host cells are also useful for conducting cell-based assays involving the transporter protein or transporter protein fragments, such as those described above as well as other formats known in the art. Thus, a recombinant host cell expressing a native transporter protein is useful for assaying compounds that stimulate or inhibit transporter protein function.

Host cells are also useful for identifying transporter protein mutants in which these functions are affected. If the mutants naturally occur and give rise to a pathology, host cells containing the mutations are useful to assay compounds that have a desired effect on the mutant transporter protein (for example, stimulating or inhibiting function) which may not be indicated by their effect on the native transporter protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a transporter protein and identifying and evaluating modulators of transporter protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the transporter protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the transporter protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, transporter protein activation, and signal transduction, may not be evident from in vitro cell-free or cell-based assays. Accordingly, it is useful to provide non-human transgenic animals to assay in vivo transporter protein function, including ligand interaction, the effect of specific mutant transporter proteins on transporter protein function and ligand interaction, and the effect of chimeric transporter proteins. It is also possible to assess the effect of null mutations, that is mutations that substantially or completely eliminate one or more transporter protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a protein comprising the amino acid sequence of SEQ ID NO:2;
   (b) a nucleotide sequence consisting of the nucleic acid sequence of SEQ ID No: 1;
   (c) a nucleotide sequence consisting of the nucleic acid sequence of SEQ ID No: 3; and
   (d) a nucleotide sequence that is completely complementary to a nucleotide sequence of (a)–(c).

2. A nucleic acid vector comprising a nucleic acid molecule of claim 1.

3. An isolated host cell comprising the nucleic acid vector of claim 2.

4. A process for producing a polypeptide comprising the amino acid sequence of SEQ ID NO: 2, comprising culturing the host cell of claim 3 under conditions sufficient for the production of said polypeptide, and recovering the peptide from the host cell culture.

5. An isolated polynucleotide consisting of the nucleotide sequence set forth in SEQ ID NO: 1.

6. An isolated polynucleotide consisting of the nucleotide sequence set forth in SEQ ID NO: 3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO: 2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of
    (a) a nucleotide sequence that encodes a protein comprising the amino acid sequence of SEQ ID NO:2;
    (b) a nucleotide sequence consisting of the nucleic acid sequence of SEQ ID No: 1; or
    (c) a nucleotide sequence consisting of the nucleic acid sequence of SEQ ID No: 3.

* * * * *